US011898209B2

(12) United States Patent
Haber et al.

(10) Patent No.: US 11,898,209 B2
(45) Date of Patent: Feb. 13, 2024

(54) DIGITAL ANALYSIS OF CIRCULATING TUMOR CELLS IN BLOOD SAMPLES

(71) Applicant: The General Hospital Corporation, Boston, MA (US)

(72) Inventors: Daniel A. Haber, Chestnut Hill, MA (US); Ravi Kapur, Sharon, MA (US); Mehmet Toner, Charlestown, MA (US); Shyamala Maheswaran, Lexington, MA (US); Xin Hong, Medford, MA (US); David Tomoaki Miyamoto, Wellesley, MA (US); Tanya Todorova, Malden, MA (US); Sarah Javaid, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 162 days.

(21) Appl. No.: 17/065,889

(22) Filed: Oct. 8, 2020

(65) Prior Publication Data

US 2021/0189501 A1   Jun. 24, 2021

Related U.S. Application Data

(63) Continuation of application No. 15/560,324, filed as application No. PCT/US2016/024367 on Mar. 25, 2016, now abandoned.

(60) Provisional application No. 62/253,619, filed on Nov. 10, 2015, provisional application No. 62/219,339, filed on Sep. 16, 2015, provisional application No. 62/137,891, filed on Mar. 25, 2015.

(51) Int. Cl.
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2600/118* (2013.01); *C12Q 2600/158* (2013.01); *C12Q 2600/16* (2013.01)

(58) Field of Classification Search
CPC ............ C12Q 1/6886; C12Q 2600/118; C12Q 2600/158; C12Q 2600/16
See application file for complete search history.

(56) References Cited

U.S. PATENT DOCUMENTS

| | | | |
|---|---|---|---|
| 6,767,512 B1 | 7/2004 | Lurz et al. | |
| 7,074,367 B2 | 7/2006 | Lurz et al. | |
| 8,535,889 B2 | 9/2013 | Larson et al. | |
| 8,841,071 B2 | 9/2014 | Link | |
| 9,068,181 B2 | 6/2015 | Edd et al. | |
| 9,074,242 B2 | 7/2015 | Larson et al. | |
| 2002/0136728 A1* | 9/2002 | King | A61P 35/00 435/6.16 |
| 2003/0064385 A1 | 4/2003 | Dressman et al. | |
| 2003/0073623 A1 | 4/2003 | Drmanac et al. | |
| 2003/0143539 A1 | 7/2003 | Bertucci et al. | |
| 2006/0275794 A1 | 12/2006 | Carrino et al. | |
| 2007/0021597 A1* | 1/2007 | Edwards | C12N 15/1089 435/6.12 |
| 2007/0083334 A1 | 4/2007 | Mintz et al. | |
| 2008/0050393 A1 | 2/2008 | Tang et al. | |
| 2009/0118175 A1 | 5/2009 | Macina | |
| 2009/0275486 A1* | 11/2009 | Kurn | C12N 15/1006 536/25.4 |
| 2011/0059556 A1* | 3/2011 | Strey | G01N 33/54326 422/503 |
| 2011/0166030 A1 | 7/2011 | Wang et al. | |
| 2012/0010086 A1* | 1/2012 | Froehlich | C12N 15/1096 506/26 |
| 2012/0015835 A1 | 1/2012 | Fuchs et al. | |
| 2012/0252015 A1* | 10/2012 | Hindson | C12Q 1/6883 435/6.12 |
| 2013/0065786 A1 | 3/2013 | Dartmann et al. | |
| 2013/0189688 A1* | 7/2013 | Shoemaker | C12Q 1/6883 435/6.11 |
| 2014/0154681 A1 | 6/2014 | Wallden | |
| 2014/0303005 A1 | 10/2014 | Samuels et al. | |
| 2015/0168413 A1 | 6/2015 | Haber et al. | |
| 2015/0233927 A1 | 8/2015 | Giannakakou et al. | |
| 2015/0240314 A1 | 8/2015 | Danila et al. | |
| 2015/0301055 A1 | 10/2015 | Spetzler | |
| 2018/0057899 A1 | 3/2018 | Haber | |
| 2019/0391134 A1 | 12/2019 | Haber et al. | |

FOREIGN PATENT DOCUMENTS

| | | |
|---|---|---|
| AU | 2015268617 | 1/2016 |
| JP | 2005-512510 A | 5/2005 |
| JP | 2014-507160 A | 3/2014 |
| JP | 2014-532409 | 12/2014 |
| JP | 2016-528252 A | 9/2016 |
| WO | WO 2009/051734 | 4/2009 |

(Continued)

OTHER PUBLICATIONS

Smirnov et al. (Cancer research 65.12 (2005): 4993-4997) (Year: 2005).*
Hayes et al. (Clinical Cancer Research 12.14 (2006): 4218-4224.). (Year: 2006).*
Lowe et al. (Nucleic Acids Research, vol. 18, No. 7, p. 1757-1761,1990) (Year: 1990).*
Untergasser et al. (Nucleic acids research 35.suppl_2 (2007): W71-W74.) (Year: 2007).*
Rozen et al. (Bioinformatics methods and protocols. Humana Press, Totowa, NJ, 2000. 365-386.) (Year: 2000).*
Nolan et al. (Nature protocols 1.3 (2006): 1559) (Year: 2006).*
Extended European Search Report in European Appln. No. 21212237. 8, dated Mar. 23, 2022, 13 pages.

(Continued)

*Primary Examiner* — Sahana S Kaup
(74) *Attorney, Agent, or Firm* — Fish & Richardson P.C.

(57) ABSTRACT

This disclosure relates to new assay methods for analysis of circulating tumor cells (CTCs) in blood samples for detection, e.g., early detection, and/or monitoring of disease, e.g., cancer. The methods provide ultra-high sensitivity and specificity, and include the use of microfluidic isolation of CTCs and digital detection of RNA derived from the CTCs.

19 Claims, 22 Drawing Sheets

Specification includes a Sequence Listing.

(56) References Cited

FOREIGN PATENT DOCUMENTS

| WO | WO 2011/112903 | 9/2011 | | |
|----|----|----|----|----|
| WO | WO 2012/115885 | 8/2012 | | |
| WO | WO 2012/135397 | 10/2012 | | |
| WO | WO-2014028378 A2 | * | 2/2014 | .......... B01F 13/0062 |
| WO | WO 2014/028378 | 2/2015 | | |
| WO | WO 2015/023710 | 2/2015 | | |
| WO | WO 2015/058206 | 4/2015 | | |
| WO | WO 2015/136017 | 9/2015 | | |
| WO | WO 2015/177184 | 11/2015 | | |
| WO | WO 2016/094904 | 6/2016 | | |
| WO | WO 2016/145308 | 9/2016 | | |
| WO | WO 2016/154600 | 9/2016 | | |

OTHER PUBLICATIONS

Ma et al., "Droplet digital PCR based androgen receptor variant 7 (AR-V7) detection from prostate cancer patient blood biopsies," International Journal of Molecular Sciences, Aug. 2016, 17(8):1264, 11 pages.

Office Action in Canadian Appln. No. 2980562, dated Feb. 24, 2022, 4 pages.

Qu et al., "Association of AR-V7 and Prostate-Specific Antigen RNA Levels in Blood with Efficacy of Abiraterone Acetate and Enzalutamide Treatment in Men with Prostate Cancer," Clinical Cancer Research, Aug. 2016, 23(3):726-734.

Todenhofer Tilman et al., "AR-V7 transcripts in whole blood RNA of patients with metastatic castration resistant prostate cancer correlate with repose to abiraterone acetate," Journal of Urology, Jul. 2016, 197(1):135-142.

CN Office Action in Chinese Appln. No. 201680029396, dated Feb. 10, 2021, 13 pages (with English translation).

Stott et al., "Supplementary Materials for Isolation and Characterization of Circulating Tumor Cells from Patients with Localized and Metastatic Prostate Cancer," Sci. Transl. Med., 2010, 12 pages.

Wang et al., "Droplet Digital PCR for Absolute Quantification of EML4-ALK Gene Rearrangement in Lung Adenocarcinoma," J Molecular Diagnostics, Sep. 2015, 17(5):515-520.

AU Office Action in Australian Appln. No. 2016238253, dated May 27, 2021, 5 pages.

CN Office Action in Chinese Appln. No 201680029396, dated Jun. 9, 2021, 8 pages (with English translation).

Aceto et al., Circulating tumor cell clusters are oligoclonal precursors of breast cancer metastasis, Cell, 2014, 158:1110-1122.

Agresti et al., "Ultrahigh-Throughput Screening in Drop-Based Microfluidics for Directed Evolution," PNAS, 2010, 107:4004-9.

Baret, "Surfactants in droplet-based microfluidics," Lab on a Chip, 2012, 12: 422-433.

Barretina et al., The Cancer Cell Line Encyclopedia enables predictive modelling of anticancer drug sensitivity, Nature, 2012, 483:603-607.

Chiappini, "Circulating tumor cells measurements in hepatocellular carcinoma," International Journal of Hepatology, May 28, 2012, 2012, 16 pages.

CN Office Action in Chinese Appln. No. 201680029396, dated Jun. 28, 2020, 11 pages (with English language translation).

Droplet Digital PCR: QX100 System, Bio-Rad Laboratories, Inc., Apr. 2014, 8 pages.

Eastburn et al., "Identification and genetic analysis of cancer cells with PCR-activated cell sorting," Nucleic Acids Research, 2014, 42: e128.

EP European Search Report and Written Opinion in Application No. 16769818.2, dated Jul. 31, 2018, 10 pages.

EP Extended European Search Report in EP Appln. No. 17865612, dated May 27, 2020, 9 pages.

EP Office Action in Appln. No. 20160769818, dated Jun. 27, 2019, 7 pages.

EP Office Action in European Appln. No. 17865612.0, dated Jun. 11, 2019, 3 pages.

Holtze et al., "Biocompatible surfactants for water-in-fluorocarbon emulsions," Lab on a Chip, 2008, 8: 1632-1639.

IL Office Action in Appln. No. IL254639, dated Feb. 17, 2019, 7 pages.

IL Office Action in Appln. No. IL254639, dated May 19, 2020, 4 pages (with English abstract).

IN Office Action in Indian Appln. No. 201747037524, dated Jul. 24, 2020, 7 pages.

International Preliminary Report on Patentability in International Application No. PCT/US2016/024367, dated Aug. 22, 2016, 16 pages.

JP Office Action in Japanese Appln. No. 2017-549623, dated Jan. 7, 2020, 9 pages.

JP Office Action in Japanese Appln. No. 2017-549623, dated Sep. 29, 2020, 8 pages (with English translation).

Kim et al., "Identification of novel markers that outperform EpCAM in quantifying circulating tumor cells," Cellular Oncology, Aug. 1, 2014, 37(4):235-43.

Kim et al., "Identification of novel markers that outperform EpCAM in quantifying circulating tumor cells," Supp. Table 3, Cellular Oncology, Aug. 1, 2014, 37(4), 2 pages.

Lingeng et al., "Circulating tumor cell clusters-associated gene plakoglobin and breast cancer survival," Breast Cancer Research and Treatment, May 2015, 151:491-500.

Lowe et al., "A computer program for selection of oligonucleotide primers for polymerase chain reactions," Nucleic Acids Research, Apr. 11, 1990, 18(7):1757-61.

Man et al., "Newly identified biomarkers for detecting circulating tumor cells in lung adenocarcinoma," The Tohoku Journal of Experimental Medicine, 2014, 234(1):29-40.

Miyamoto et al., RNA-Seq of single prostate CTCs implicates noncanonical Wnt signaling in antiandrogen resistance, Science, 2015, 349:1351-1356.

Nolan et al., "Quantification of mRNA using real-time RT-PCR," Nature Protocols, 2006, 1(3):1559-1582.

Ozkumur et al., "Inertial Focusing for Tumor Antigen-Dependent and -Independent Sorting of Rare Circulating Tumor Cells," Science Translational Medicine, Apr. 2013, 5: 179ra47, 11 pages.

PCT International Preliminary Report on Patentability for International Appln. No. PCT/US2017/058855, dated Apr. 30, 2019, 11 pages.

PCT International Preliminary Report on Patentability in International Application No. PCT/US2016/024367, dated Sep. 26, 2017.

PCT International Search Report and Written Opinion in International Appln. No. PCT/US2017/058855, dated Apr. 26, 2018, 23 pages.

Plaks et al., "Circulating tumor cells," Science, Sep. 13, 2013, 341(6151):1186-8.

Pomerantz et al., "The androgen receptor cistrome is extensively reprogrammed in human prostate tumorigenesis," Nature Genetics, Nov. 2015, 47(11):1346-1351.

Ramsköld et al, "Full-length mRNA-Seq from single-cell levels of RNA and individual circulating tumor cells," Nature biotechnology, Aug. 2012, 30(8):777.

Ramsköld et al, "Full-length mRNA-Seq from single-cell levels of RNA and individual circulating tumor cells," Supp. Table 4, Nature biotechnology, Aug. 2012, 30(8), 3 pages.

Rozen et al., "Primer3 on the WWW for General Users and for Biologist Programmers," Bioinfornnatics Methods and Protocols. Humana Press, Totowa, NJ, 2000, 365-386.

Sequist et al., "The CTC-Chip: An Exciting New Tool to Detect Circulating Tumor Cells in Lung Cancer Patients," Journal of Thoracic Oncology, Mar. 2009, 4: 281-283.

Smirnov et al., "Global gene expression profiling of circulating tumor cells," Cancer Research, Jun. 15, 2005, 65(12):4993-4997.

Smirnov et al., "Global gene expression profiling of circulating tumor cells," Supp. Table 2, Cancer Research, Jun. 15, 2005, 65(12), 3 pages.

Stott et al., "Isolation and Characterization of Circulating Tumor Cells from Patients with Localized and Metastatic Prostate Cancer," Science Translational Medicine, Mar. 2010, 2: 111-120.

Taly et al., "Detecting biomarkers with microdroplet technology," Trends in Molecular Medicine, Jul. 2012, 18: 405-416.

(56) References Cited

OTHER PUBLICATIONS

Ting et al., Single-Cell RNA Sequencing Identifies Extracellular Matrix Gene Expression by Pancreatic Circulating Tumor Cells, Cell Rep, 2014, 8:1905-1918.
Untergasser et al., "Primer 3Plusan enhanced web interface to Primer3," Nucleic Acids Research, 2007, 35(2):W71-W74.
Wang et al., "Gene expression markers in circulating tumor cells may predict bone metastasis and response to hormonal treatment in breast cancer," Molecular and Clinical Oncology, Nov. 1, 2013;1(6):1031-8.
Yu et al., "Ex vivo culture of circulating breast tumor cells for individualized testing of drug susceptibility," Science, Jul. 2014, 345(6193):216-220.
JP Office Action in Japanese Appln. No. 2019-522657, dated Sep. 7, 2021, 8 pages (with English translation).
Pouladi, "Dissecting the Heterogeneity of Breast Tumor Subtypes," Thesis for the degree of Doctor of Philosophy in Genetics, Dartmouth College, Feb. 2014, 240 pages.
Office Action in Chinese Appln. No. 201680029396.X, dated Nov. 8, 2021, 13 pages (with English translation).
Notice of Acceptance in Australian Appln. No. 2016238253, dated Jun. 6, 2022, 4 pages.
Office Action in Japanese Appln. No. 2019-522657, dated May 10, 2022, 8 pages (with English translation).
Office Action in Chinese Appln. No. 201780075515.X, dated Nov. 3, 2022, 18 pages (with English translation).

\* cited by examiner

DIGITAL ANALYSIS OF CIRCULATING TUMOR CELLS IN BLOOD SAMPLES

CROSS-REFERENCE TO RELATED APPLICATIONS

This application is a continuation of U.S. application Ser. No. 15/560,324, filed on Sep. 21, 2017, which is a 371 U.S. National of PCT Application No. PCT/US2016/024367, filed on Mar. 25, 2016, which claims priority from U.S. Provisional Application Ser. No. 62/253,619, filed on Nov. 10, 2015, U.S. Provisional Application Ser. No. 62/219,339, filed on Sep. 16, 2015, and U.S. Provisional Application Ser. No. 62/137,891, filed on Mar. 25, 2015, the contents of which are incorporated herein by reference in their entireties.

TECHNICAL FIELD

This invention relates to blood sampling techniques, and more particularly to methods and systems for detecting and analyzing cells in blood samples. cl BACKGROUND The ability to detect the presence of rare circulating tumor cells (CTCs) using a simple blood test, or "liquid biopsy," has the potential to greatly enhance the monitoring of epithelial cancers, providing instant sampling of tumor cell numbers, genetic composition, and drug response parameters, without requiring invasive tumor biopsies. Thus, the detection of CTCs for early cancer detection has the potential to revolutionize the treatment of cancer, enabling the diagnosis of invasive cancer at a stage before it has metastasized, when curative treatment is expected.

However, CTCs are very rare, and identifying, visualizing, and scoring these tumor cells admixed with normal blood components remains a significant challenge, even after partial purification with known microfluidic devices or similar technologies. For example, per milliliter of whole blood, there are only 1-10 CTCs amongst more than 5 billion red blood cells (RBCs) and more than 5 million white blood cells (WBCs)(Plaks et al., "Cancer Circulating Tumor Cells," Science, 341:1186; 2013). In addition, antibody staining of tumor cells is highly variable, due to high heterogeneity among cancer cells, even within an individual patient, as well as the poor physical condition of many tumor cells that circulate in the bloodstream, many of which have begun to undergo programmed cell death or anoikis. In addition, accurate scoring of antibody-stained tumor cells requires differentiation from large numbers of contaminating white blood cells, some of which bind to antibody reagents non-specifically. As such, only a subset of candidate tumor cells can be robustly identified by antibody staining, and as many as half of patients tested have no detectable cells, despite having widely metastatic cancer.

Thus, current protocols for imaging CTCs are seeking higher and higher levels of purity in the isolation of CTCs, especially from other nucleated blood cells, such as white blood cells (WBCs).

SUMMARY

The present disclosure relates to methods, uses, and systems to obtain the highest possible sensitivity of data relating to rare CTCs in standard blood samples, while avoiding the need for extremely high levels of purity of the CTCs. In particular, the new methods do not need the CTCs to be completely isolated from contaminating WBCs, and instead can reliably detect as few as one CTC in products containing, e.g., up to 10,000 WBCs or more. The new assay methods and systems combine (1) an isolation system that can consistently obtain CTCs as intact, whole cells (with high quality ribonucleic acid (RNA)) from blood with (2) a droplet-based digital polymerase chain reaction (PCR) assay focused on ribonucleic acid RNA markers of specific cancer lineages for each tumor type that are absent in blood of healthy patients.

When combined as described herein, these two concepts provide a CTC digital droplet PCR assay method ("CTC ddPCR") or simply stated a "digital-CTC" assay ("d-CTC"). In some embodiments, the isolation system is a microfluidic system, such as a negative depletion microfluidic system (e.g., a so-called "CTC-Chip," that uses negative depletion of hematopoietic cells, e.g., red blood cells (RBCs), WBCs, and platelets, to reveal untagged non-hematopoietic cells such as CTCs in a blood sample).

In general, the disclosure relates to methods for early detection of cancer with ultra-high sensitivity and specificity, wherein the methods include the use of microfluidic isolation of circulating tumor cells (CTCs) and digital detection of RNA derived from the CTCs. In some embodiments, the CTC-derived RNA can be converted into cDNA and encapsulated into individual droplets for amplification in the presence of reporter groups that are configured to bind specifically to cDNA from CTCs and not to cDNA from other cells. The droplets positive for reporter groups can be counted to assess the presence of disease, e.g., various types of cancer.

In another aspect, the disclosure relates to methods of analyzing circulating tumor cells (CTCs) in a blood sample. The methods include or consist of isolating from the blood sample a product comprising CTCs and other cells present in blood; isolating ribonucleic acid (RNA) molecules from the product; generating cDNA molecules in solution from the isolated RNA; encapsulating cDNA molecules in individual droplets; amplifying cDNA molecules within each of the droplets in the presence of reporter groups configured to bind specifically to cDNA from CTCs and not to cDNA from other cells; detecting droplets that contain the reporter groups as an indicator of the presence of cDNA molecules from CTCs in the droplets; and analyzing CTCs in the detected droplets.

The methods described herein can further include reducing a volume of the product before isolating RNA and/or removing contaminants from the cDNA-containing solution before encapsulating the cDNA molecules.

In various implementations of the new methods, generating cDNA molecules from the isolated RNA can include conducting reverse transcription (RT) polymerase chain reaction (PCR) of the isolated RNA molecules and/or amplifying cDNA molecules within each of the droplets can include conducting PCR in each droplet. In the new methods, encapsulating individual cDNA molecules and PCR reagents in individual droplets can include forming at least 1000 droplets of a non-aqueous liquid, such as one or more fluorocarbons, hydrofluorocarbons, mineral oils, silicone oils, and hydrocarbon oils and/or one or more surfactants. Each droplet can contain, on average, one target cDNA molecule obtained from a CTC. In some embodiments, the reporter groups can be or include a fluorescent label.

The new methods can include removing contaminants from the cDNA-containing solution by use of Solid Phase Reversible Immobilization (SPRI), e.g., immobilizing cDNA in the solution, e.g., with magnetic beads that are configured to specifically bind to the cDNA; removing contaminants from the solution; and eluting purified cDNA.

In various implementations, the methods described herein include using probes and primers in amplifying the cDNA molecules within each of the droplets that correspond to one or more genes selected from the list of cancer-selective genes in Table 1 herein. For example, the selected genes can include prostate cancer-selective genes, e.g., any one or more of AGR2, FOLH1, HOXDB13, KLK2, KLK3, SCHLAP1/SET4, SCHLAP1/SET5, AMACR, AR variants, UGT2B15/SET1, UGT2B15/SET5, and STEAP2 (as can be easily determined from Table 1). In another example, any one or more of ALDH1A3, CDH11, EGFR, FAT1, MET, PKP3, RND3, S100A2, and STEAP2 are selective for pancreatic cancer. Similar lists can be generated for the other types of cancers listed in Table 1.

In other examples, the selected genes include any one or more of the breast cancer-selective genes listed in Table 1. In other examples, the selected genes include genes selective for one or more of lung, liver, prostate, pancreatic, and melanoma cancer. For example, a multiplexed assay can include 2, 3, 4, 5, 6, 7, 8, 9, 10, 11, 12 or even all of the selected genes that are listed in Table 1 as being selective for a particular type of cancer, e.g., breast cancer, lung cancer, prostate cancer, pancreatic cancer, liver cancer, and melanoma. Typically a group of primers and probes for 5 to 12 cancer-selective genes from Table 1 are used for a particular type of cancer. Other specific combinations of selected genes (markers for those genes) are described in the Examples below.

The methods can also include using one or more genes selective for two or more, three or more, four or more, or five or more different types of cancer. For example, the genes can be selective for breast cancer and lung cancer; breast cancer, lung cancer, and liver cancer; breast cancer, lung cancer, and pancreatic cancer; breast cancer, lung cancer, and prostate cancer; breast cancer, liver cancer, and melanoma; breast cancer, lung cancer, and melanoma; breast cancer, lung cancer, liver cancer, and prostate cancer; breast cancer, lung cancer, liver cancer, and melanoma; breast cancer, lung cancer, liver cancer, and pancreatic cancer; breast cancer, lung cancer, prostate cancer, and pancreatic cancer; breast cancer, lung cancer, liver cancer, melanoma, and pancreatic cancer; or breast cancer, lung cancer, liver cancer, melanoma, pancreatic cancer, and prostate cancer.

In the methods described herein, the CTCs can arise from metastatic or primary/localized cancers. In the new methods, the step of analyzing the CTCs in the detected droplets cam include monitoring CTCs from a blood sample from a patient, e.g., with a known cancer, e.g., over time, and testing and/or imaging the CTCs (e.g., using standard techniques) to provide a prognosis for the patient. In other embodiments, the step of analyzing the CTCs in the detected droplets can include testing and/or imaging the CTCs (e.g., using standard techniques) from a blood sample from a patient to provide an indication of a response by the CTCs to a therapeutic intervention.

In other embodiments, the step of analyzing the CTCs in the detected droplets includes determining a number or level of CTCs per unit volume of a blood sample from a patient to provide a measure of tumor burden in the patient. The methods can then further include using the measure of tumor burden in the patient to select a therapy or can further include determining the measure of tumor burden in the patient at a second time point to monitor the tumor burden over time, e.g., in response to a therapeutic intervention, e.g., for dynamic monitoring of tumor burden.

The methods and assays described herein can be used to amplify and detect CTCs in a wide variety of diagnostic, prognostic, and theranostic methods.

As used herein, the phrase "circulating tumor cells" (CTCs) refers to cancer cells derived from solid tumors (non-hematogenous cancers) that are present in very rare numbers in the blood stream of patients (e.g., about 1 CTC in about 10,000,000 WBCs in whole blood). CTCs can arise from both metastatic as well as primary/localized cancers.

As used herein, a "product" means a group of isolated rare cells and other contaminating blood cells, e.g., red blood cells, white blood cells (e.g., leukocytes), e.g., in some sort of liquid, e.g., a buffer, such as a pluronic buffer, that arise from processing in the methods described herein, e.g., using the systems described herein. A typical product may contain only about one to ten CTCs admixed with 500 to 2,500 or more WBCs, e.g., one to ten CTCs in a mixture of 1000 to 2000 WBCs. However, the limit of detection of the present methods can be about 1 CTC in 10,000 WBC. Thus, while the present methods can achieve a level of purity of about 1 CTC in 500 WBCs, the present methods do not require highly purified CTCs, as is required in some known methods of CTC analysis.

As used herein a Solid Phase Reversible Immobilization (SPRI) cleanup is a technique using coated magnetic beads to perform size selection on cDNA created from Reverse Transcription (RT)-PCR of a product. In the new assay methods described herein this accomplishes the two-fold purpose of (a) selecting only the cDNA of the correct size, and (b) removing harsh lysis detergents incompatible with the stability of the droplets.

The polymerase chain reaction (PCR) is a process of amplification of known DNA fragments by serial annealing and re-annealing of small oligonucleotide primers, resulting in a detectable molecular signal.

Reverse Transcription (RT)-PCR refers to the use of reverse transcription to generate a complementary c-DNA molecule from an RNA template, thereby enabling the DNA polymerase chain reaction to operate on RNA. An important aspect of the new methods disclosed herein is the availability of high quality RNA from whole cell CTCs that are not lysed or treated in such a way that might destroy or degrade the RNA.

As used herein, "positive droplets" are lipid-encapsulated molecules in which a PCR reaction performed with tagged primers allows visualization of the PCR amplified product. Thus, a droplet that contained a single template cDNA molecule of a particular targeted gene can become visible using fluorescence microscopy, while an "empty" or "negative" droplet is one that contains no targeted cDNA.

The new methods and systems provide numerous advantages and benefits. For example, the current methods and systems provide results that are far more accurate and robust than either of the prior known systems when used alone. By breaking down the signal from a single CTC into hundreds or thousands of brightly fluorescent droplets, each derived from a single cDNA molecule, the new digital-CTC assays enable dramatic signal amplification. Given the strict criteria in selecting and optimizing the biomarker genes described herein, the background signal from normal blood cells is negligible in d-CTC. Thus, d-CTC enables greatly amplified signal from patients with advanced cancer (nearly 100% of patients with prostate, lung, breast, and liver cancers). Not only is the fraction of patients with a positive score significantly increased, but the high level of signal enables dynamic measurements as tumor load declines following cancer therapy. In addition, the signal amplification permits detection of CTC-derived signatures even in patients with a very low tumor burden (something that is not readily accomplished with CTC cell imaging), thus enabling significantly earlier detection of cancer.

In sum, this novel microfluidics platform provides a streamlined, ultrahigh-throughput, rapid (e.g., 3 hours per run), and extremely high sensitivity method of enriching, detecting, and analyzing CTCs in patient blood samples. The platform provides rich, clinically actionable information, and with further optimization may enable early detection of cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 19A is a bar graph that shows the level of amplicon amplification efficiency for different target regions that is consistent among the three replicates (WTA1, WTA2, WTA3). FIG. 19B is a graph that shows that using 18 cycles of SMARTer pre-amplification provides an increase in signal of approximately four orders of magnitude ($10^8$ vs $10^4$) compared to a non-pre-amplified sample.

FIGS. 20A to 20C show the total droplet numbers in 21 hepatocellular carcinoma (HCC) patients (FIG. 20A), 13 chronic liver disease (CLD) patients (FIG. 20B, no significant detectable droplets) and 15 healthy donors (HDs) (FIG. 20C, no significant detectable droplets).

FIG. 21A shows the assay results for the 8 metastatic lung cancer patients and 8 healthy donors (all negative). FIG. 21B shows that all of the droplet counts per ml of blood in the cancer patients (8 of 8) were higher than in all healthy donors giving a detection rate of 100% in this assay.

FIG. 23A is a bar graphs that shows the results for samples from 10 metastatic breast cancer patients and 7 healthy donors processed though the CTC-Chip as described herein. FIG. 23B shows that five of the ten cancer patient samples were above the healthy donor background level giving a detection rate of 5 in 10, or 50%.

DETAILED DESCRIPTION

Figures 1A, 1B, 1C:
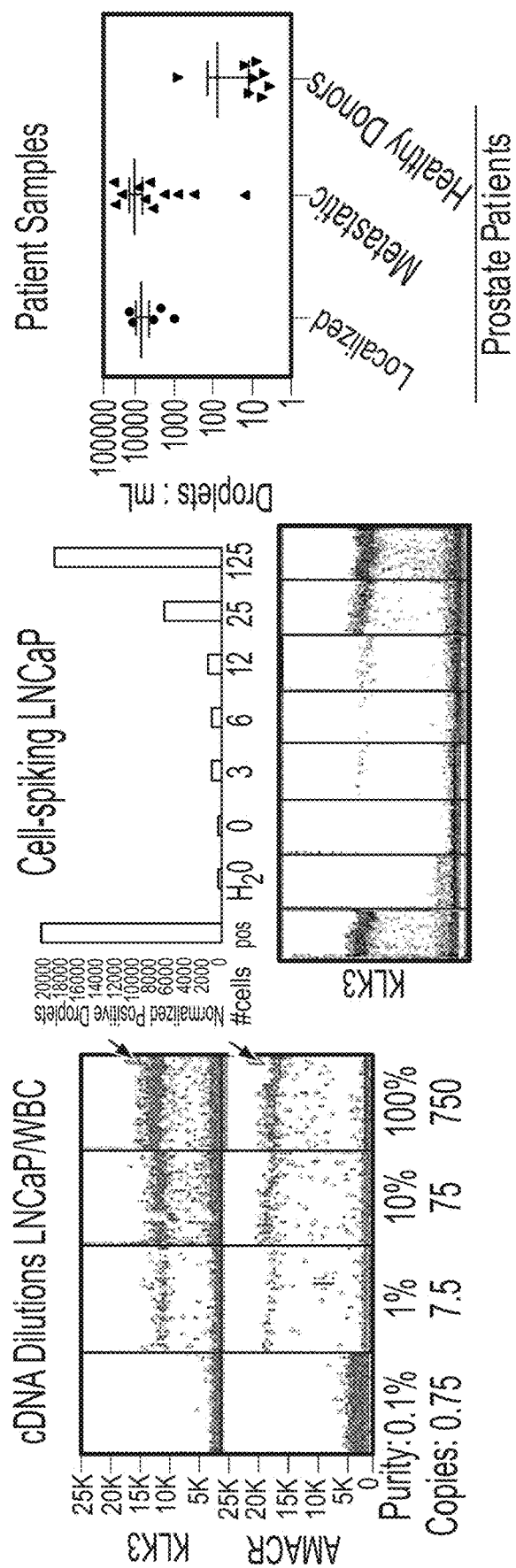
FIG. 1A is a graph showing cDNA dilutions prepared from total RNA of LNCaP prostate cancer cells, mixed with leukocytes and analyzed by droplet PCR using two different prostate primer sets. The results represent several purities and show good response of positive droplet number across this range.
FIG. 1B is a graph of manually isolated LNCaP cells spiked into healthy donor (HD) blood samples, run through the CTC-iChip, and subjected to droplet RT-PCR (KLK3 primer set). The results show excellent sensitivity down to low numbers of target cells.
FIG. 1C is a graph that shows the analysis of blood samples from healthy controls, patients with localized (resectable) prostate cancer and metastatic prostate cancer, processed through the CTC-iChip, subjected to RT-PCR and droplet analysis using three prostate-specific and one epithelial-specific biomarkers (KLK3, AMACR, FOLH1, EpCAM). The results are shown for the total number of droplets/ml for all four markers combined.

The present disclosure relates to methods and systems to obtain information from rare cancer cells in blood samples. These methods and systems combine the power of isolation techniques such as ultrahigh-throughput microfluidic techniques, for example, negative depletion techniques, e.g., those using negative depletion of hematopoietic cells to isolate untagged CTCs in a blood sample, with analysis techniques, such as droplet-based digital polymerase chain reaction (PCR) assays focused on ribonucleic acid (RNA) markers of specific cancer lineages. This strategy can also be applied to other CTC isolation technologies that provide partially purification of cells (e.g., filtration, positive tumor cell selection), although the quality of the RNA and hence the sensitivity of the assay will be inferior to the microfluidic technologies. Similarly, other digital PCR technologies applied to RNA are capable of detecting lineage-specific primers, although the sensitivity of the droplet-based assay is likely to be the highest.

The new methods described herein can be used not only for early detection of cancers based on the presence of the CTCs in the blood, but also for tumor burden quantification as well as to monitor CTCs from a particular tumor over time, e.g., to determine any potential changes in specific tumor marker genes present in the CTCs as well changes in the tumor as the result of specific therapies, e.g., in the context of a clinical trial or a particular therapy.

General Concepts of the Assay Methods

The isolation techniques are used to enrich CTCs from a blood sample, e.g., using ultrahigh-throughput microfluidic such as the so-called "CTC-iChip" described in, for example, International PCT Application WO 2015/058206 and in Ozkumur et al., "Inertial Focusing for Tumor Antigen-Dependent and -Independent Sorting of Rare Circulating Tumor Cells," *Sci. Transl. Med.,* 5:179ra47 (2013). The CTC-iChip uses a CTC antigen-independent approach in which WBCs in the blood sample are labeled with magnetic beads, and the sample is then processed through two enrichment stages. The first stage uses deterministic lateral displacement to remove small and flexible cells/particles (RBCs, platelets, unbound magnetic beads, and plasma) while retaining larger cells (CTCs and WBCs). The second stage moves all cells into a narrow fluid stream using inertial focusing and then uses a magnetic field to pull bead-labeled WBCs out of the focused stream, leaving highly enriched CTCs. The CTC-iChip product from 10 ml of whole blood typically contains <500,000 RBCs, <5,000 WBCs, and a variable number of CTCs.

Some analysis techniques further enrich and analyze the isolated CTCs, e.g., as obtained from the CTC-iChip, e.g., using droplet microfluidics. Some basic information on droplet microfluidics is described generally in Jeremy et al., "Ultrahigh-Throughput Screening in Drop-Based Microfluidics for Directed Evolution," Proc. Natl. Acad. Sci. USA, 107:4004 (2010).

As used herein, the droplet microfluidic techniques can, in certain implementations, include encapsulation of single cells, RT-PCR reagents, and lysis buffer into droplets of typically non-aqueous liquids (e.g., fluorocarbons, hydrofluorocarbons, mineral oil, silicone oil, and hydrocarbon oil; surfactants can also be include in the non-aqueous liquid, e.g., Span80, Monolein/oleic acid, Tween20/80, SDS, n-butanol, ABIL EM90, and phospholipids), in the size range of, e.g., about 0.5 pL to 15 nL in volume and, e.g., 10 to 300 μm, e.g., 20 to 100 μm, e.g., 30 to 50 μm, e.g., 35 μm in diameter. As used in the new methods described in the present disclosure, these techniques further include amplification of cancer-specific transcripts within the droplets to produce a fluorescent signal, and sorting of amplification-positive drops. This approach results in isolation of pure CTCs that can be sequenced and analyzed for the purposes of diagnosis and individualized drug therapy. Due to the high heterogeneity of CTCs, it is useful to use multiplexed amplification to detect as many CTCs as possible. Thus, instead of using one pair of primers in the PCR mixture, one can increase the probability of detecting and sorting CTCs using a combination of tumor specific primers. For additional information on the use of PCR for sorting cancer cells, see, e.g., Eastburn et al., "Identification and genetic analysis of cancer cells with PCR-activated cell sorting," Nucleic Acids Research, 2014, Vol. 42, No. 16 e128.

In the new assay methods CTCs are lysed to release RNA molecules, which are representative of the genes expressed in a cancer cell. Most are "lineage" specific, rather than cancer specific, for example any prostate cell (whether cancerous or not) expresses these markers. However, normal blood cells do not, and the fact that the signal is derived from a cell circulating in the bloodstream defines it as an abnormal signal. By converting the RNA to a cDNA, we can now PCR amplify this lineage signal. We use droplet digital PCR, which is extraordinarily sensitive, allowing to convert the signal from a single cancer cell (i.e., one signal in an imaging assay) into thousands of positive immunofluorescent droplets. The combination of multiple, highly curated gene transcripts ensures high sensitivity and specificity for cancer, and also allows for functional insights (as in the status of hormone responsive pathways in prostate and breast cancers).

As noted, the new assay methods focus on the detection and analysis of high quality RNA rather than DNA. While there has been considerable work on DNA mutation detection in plasma and in CTCs, the present methods rely on RNA markers for the following reasons:

1. DNA mutations are not tumor specific, and the discovery that a healthy individual has some unidentified cancer cells in the blood is a very difficult clinical situation. In contrast, by selecting tumor-specific RNAs (e.g., prostate vs lung), the new methods can identify the source of cancer cells in the blood.

2. DNA mutations are very heterogeneous and besides a few recurrent mutations shared by many cancers, most blood-based mutation detection strategies require pre-existing knowledge of the mutations present in the primary tumor (i.e. not appropriate for screening for unknown cancers). In contrast, all tumor cells derived from specific organs express common lineage markers at the RNA level. Thus, a single cocktail of markers is used in the new methods for each individual type of cancer.

3. Low levels of CTCs are shed by invasive cancers before metastases are established (i.e., it is not too late for blood-based detection), but the presence of tumor cells in the blood connotes vascular invasion (i.e., invasive rather than indolent cancer). That is not the case for plasma DNA or plasma protein markers, which are leaked from dying cells in the primary tumor, and do not necessarily indicate vascular invasion. For example, serum PSA protein in the blood is shed by both benign prostate cells as well as primary prostate cancers. On the other hand, CTCs expressing PSA are shed only by invasive prostate cancers.

4. The analysis of RNA using the novel digital scoring technologies described herein is extraordinarily sensitive. However, free RNA is degraded in the bloodstream, and the use of isolation systems as described herein, such as microfluidic negative depletion systems (e.g., the CTC-Chip system) is unique in that the untagged tumor cells have high quality RNA which is extractable.

The choice of cDNA as a target molecule over DNA was made to not only to boost the signal originating from each tumor cell, but also to specifically target only tumor cell transcripts to the exclusion of white blood cell (WBC) transcripts. The boost in signal is a significant advantage, as it avoids the need for the isolation of CTCs to very high levels of purity. That is, it enables robust and repeatable results with products that contain one or more "isolated" CTCs that are still surrounded by hundreds or thousands of contaminating WBCs, e.g., leukocytes, in the same product. Nevertheless, the strategy of targeting cDNA made from RNA as used in the new methods allows the new assay methods to be exquisitely tailored for maximum specificity with minimal levels of CTC purity compared to prior approaches.

The CTC-iChip technology is highly efficient at isolating non-hematopoietic cells by microfluidic depletion of antibody tagged leukocytes. This feature of the CTC-iChip provides intact tumor-derived RNA (at levels far above those obtained using other technologies), and it is independent of tumor cell surface epitopes (which are highly heterogeneous among cancers and among epithelial vs mesenchymal cell subtypes within an individual cancer). Furthermore, even pre-apoptotic cancer cells whose antibody staining and selection is suboptimal for imaging analysis can provide a source of tumor-specific RNA that can be scored using the methods described herein. For all these reasons, an isolation technology or system that provides high quality RNA from intact CTCs with at least some reduction in the WBCs found in the sample along with the rare CTCs, such as a microfluidic negative depletion system, e.g., the CTC-iChip, is an important first step isolation before the tumor-specific digital readout is applied to the product.

The droplet-based digital detection of extremely rare molecules within a heterogeneous mixture was originally developed for PCR amplification of individual DNA molecules that are below detection levels when present within a heterogeneous mixture, but which are readily identified when sequestered within a lipid droplet before being subjected to PCR. The basic technology for droplet-based digital PCR ("Droplet Digital PCR (ddPCR)") has been commercialized by RainDance and Bio-Rad, which provide equipment for lipid encapsulation of target molecules followed by PCR analysis. Important scientific advances that made this possible include work in the laboratory of David Weitz at Harvard and Bert Vogelstein at Johns Hopkins. For example, see U.S. Pat. Nos. 6,767,512; 7,074,367; 8,535,889; 8,841,071; 9,074,242; and U.S. Published Application No. 2014/0303005. See also U.S. Pat. No. 9,068,181.

However, droplet digital PCR itself is not biologically significant unless coupled to a biological source of material, which is key to the new methods described herein. For instance detection of lineage-specific RNAs (the central focus of our detection strategy) does not distinguish between normal prostate epithelial cells and cancerous prostate cells. As such, detection of prostate-derived transcripts in the blood is not meaningful: they are present within debris from normal prostate cells or exosomes. It is only when coupled with the isolation of whole CTCs (i.e., intact CTCs in the blood) that the ddPCR assay achieves both extraordinary sensitivity and specificity. Hence these two technologies are ideally suited for each other, because the isolation systems provide high quality RNA, and the droplet-based digital PCR assays are focused on RNA markers in the new methods.

One additional aspect is important to the overall success of the new assay methods. As noted, the new assay methods described herein use cDNA made from total RNA, but key to this use is the identification of appropriate biomarkers that are tumor lineage-specific for each type cancer, yet are so unique as to be completely absent in normal blood cells (even with ddPCR sensitivity). The selection, testing, and validation of the multiple target RNA biomarkers for each type of cancer described herein enable the success of the new assay methods.

Assay Method Steps

The new assay methods start with the isolation of partially pure CTCs using an isolation system, such as a microfluidic negative depletion system, up to and including the analysis of data from a droplet digital PCR instrument. There are eight main assay steps, some of which are optional, though generally provide better results:

1. isolating from the blood sample a product including CTCs and other cells present in blood; e.g. from a patient or a subject;

2. reducing a volume of the rare cell-containing product (optional);

3. isolating ribonucleic acid (RNA) molecules from the product, e.g., by cell lysis, and generating cDNA molecules in solution from the isolated RNA; e.g., by RT-PCR of RNA released from cells contained in the product;

4. cleanup of cDNA synthesized during the RT-PCR step (optional);

5. pre-amplifying the cDNA using gene-specific targeted preamplification probes, e.g., using the Fluidigm BioMark™ Nested PCR approach, or non-specific whole-transcriptome amplification, e.g., using the Clontech SMARTer™ approach (optional);

6. encapsulating cDNA molecules in individual droplets, e.g., along with PCR reagents;

7. amplifying cDNA molecules within each of the droplets in the presence of reporter groups configured to bind specifically to cDNA from CTCs and not to cDNA from other cells, e.g., using PCR;

8. detecting droplets that contain the reporter groups (e.g., "positive" droplets) as an indicator of the presence of cDNA molecules from CTCs in the droplets; and 9. analyzing CTCs in the detected droplets, e.g., to determine the presence of a particular disease in a patient or subject.

As described in further detail below, one of the important features of the new d-CTC assay methods is the careful selection of a number of target gene biomarkers (and corresponding primers) that deliver excellent sensitivity, while simultaneously maintaining nearly perfect specificity. A unique list of target gene biomarkers described herein (Table 1, below) was determined using bioinformatics analyses of publicly available datasets and proprietary RNAseq CTC data. Great care was taken to select markers that are not expressed in any subpopulations of leukocytes, but are expressed at a high enough frequency and intensity in CTCs to provide a reliable signal in a reasonably wide array of different and distinct patients. A specific set of markers was selected for each cancer type (e.g. prostate cancer, breast cancer, melanoma, lung cancer, pancreatic cancer, among others.)

The separate steps of the assay methods will now be described in more detail.

1. CTC Isolation

Patient blood is run through the CTC-iChip, e.g., version 1.3M or 1.4.5T and a sample is collected in a 15 mL conical tube on ice. CTC-iChips were designed and fabricated as previously described (Ozkumur et al., "Inertial Focusing for Tumor Antigen-Dependent and -Independent Sorting of Rare Circulating Tumor Cells," Science Translational Medicine, 5(179):179ra47 (DOI: 10.1126/scitranslmed.3005616) (2013)).

The blood samples (~20 mls per cancer patient) are collected in EDTA tubes using approved protocols. These samples are then incubated with biotinylated antibodies against CD45 (R&D Systems) and CD66b (AbD Serotec, biotinylated in house) and followed by incubation with Dynabeads® MyOne® Streptavidin T1 (Invitrogen) to achieve magnetic labeling of white blood cells (Ozkumur et al., 2013).

The sample is then processed through the CTC-iChip, which separates the blood components (red and white blood cells and platelets) as well as unconjugated beads away from the CTCs. The CTCs are collected in solution while the red blood cells, platelets, unconjugated beads and the tagged white blood cells are collected in a waste chamber. The process is automated and 10 ml of blood is processed in 1 hour.

2. Volume Reduction and Storage of the Rare Cell-Containing Product

To fully lyse all cells isolated in the product, it is preferable to reduce the product volume from a typical starting point of several milliliters to a final volume of about 100 µl. This can be achieved, for example, by centrifuging the product, and resuspending in pluronic buffer in preparation for cell lysis and generation of cDNA. At this point samples can be processed for long-term storage by adding RNAlater™ (ThermoFisher), followed by flash-freezing in liquid nitrogen and storage at −80C.

3. Isolating RNA and Generation of cDNA from Cells in the Product

The RNA isolation step is important to the process to fully release all RNA molecules from cells in preparation for RT-PCR. A one-step, in-tube reaction can be used to minimize the risk of cell and RNA loss likely to be incurred during standard transfer steps. For example, one can use the Invitrogen SuperScript III® First-Strand Synthesis Supermix® for qRT-PCR kit, by adding the RT-PCR mastermix directly to the pelleted product, pipetting to lyse fully, and performing the reaction according to the kit protocol targeting a 1:1 RNA:cDNA ratio. Once cDNA has been synthesized, RNase H is applied to the reaction to remove any remaining RNA. Alternatively, if one wants to perform whole transcriptome pre-amplification of the sample in a later step, cDNA can be synthesized using the SMARTer™ Ultra Low Input RNA Kit protocol, which uses proprietary oligonucleotides and reverse transcriptase enzyme.

4. Cleanup of cDNA Synthesized During RT-PCR

Another useful, yet optional, step in the process involves the removal of lysis reagents from the cDNA-containing solution. The presence of harsh detergents can lead to the destabilization of the droplets used in the ddPCR method, once the cDNA-containing solution is transferred to the ddPCR instrument. Detergent removal can be accomplished, e.g., through the use of Solid Phase Reversible Immobilization (SPRI). This technique uses coated magnetic beads to first bind cDNA of a specific size range, then allows removal of detergent-containing supernatant, and finally elution of pure cDNA for input into the ddPCR instrument. In addition to the cleanup of the RT-PCR, the SPRI process also accomplishes a size selection of cDNA, which reduces the number of non-target cDNA molecules that enter the ddPCR phase of the process, which in turn reduces background and noise.

5. Pre-Amplification

Pre-amplification of the cDNA is an optional step that increases the number of template molecules that can be detected in the droplet PCR step thus improving signal-to-noise ratio and boosting the confidence in a positive readout. It can be a very powerful approach for the detection of markers that are expressed at low levels in CTCs, and for analyzing samples that contain very small numbers of possibly apoptotic CTCs, such as in the context of early detection of pre-metastatic disease. These two approaches have been modified to be applied in the workflow of d-CTC assay. Specific Targeted Amplification (STA), based on the Fluidigm BioMark™ Nested PCR protocol, relies on the use of primers specifically designed to amplify the region targeted by the probes used in the droplet PCR step (see Table 2). These primers were carefully designed and tested in conjunction with their respective fluorescent probes to ensure efficient and specific amplification without increase in noise in healthy controls. Alternatively, whole transcriptome amplification, based on the SMARTer™ Ultra Low Input RNA Kit protocol, relies on the amplification of every transcript in the product, including both those found in WBCs and those found in CTCs, using random primers.

6. Encapsulation of cDNA Plus PCR Reagents in Droplets

Once cDNA has been synthesized and purified of contaminating detergents, the entire aggregate of cDNA molecules in solution plus qPCR reagents is divided into many tiny compartmentalized reactions, for example, by a droplet making instrument, e.g., a droplet generator such as the Biorad Automated Droplet Generator, which generates 20,000 droplets per sample. Each reaction consists of an extremely small droplet of non-aqueous fluid, e.g., oil (PCR stable, e.g., proprietary formulation from vendor), which contains Taqman-type PCR reagents with gene-specific primers and an oligonucleotide probe, and a small amount of sample. Once droplet generation is complete, the sample consists of an emulsion containing a vast number of individual PCR-ready reactions.

For this step, one can use the PCR probes and related primers for any one or two or more different target genes listed in Table 1 below for overall determination of tumor load, e.g., to determine tumor progression or response to therapy, in single or multiplex reactions. Thus, although in some cases a single set of PCR primers and probes for a particular gene from Table 1 can be included in each droplet, it is also possible to multiplex PCR primers and probes for two or more different genes in each droplet using different fluorescent probes for each primer/probe set, to maximize the detection of tumor cells, given the heterogeneity of gene expression in CTCs. It is also possible to multiplex PCR primers and probes for multiple genes targeting different cancer types in each droplet, thus enabling the broad yet specific detection of multiple tumor types in a single assay.

7. PCR of Droplet Encapsulated cDNA Molecules

Standard PCR cycling is performed on the entire emulsion sample using qPCR cycling conditions. The reaction is carried to 45 cycles to ensure that the vast majority of individual droplet-PCR volumes are brought to endpoint. This is important because, although the reaction is performed with Taqman-type qPCR reagents and cycled under qPCR conditions, the fluorescent intensity of the sample will not be measured during the PCR cycling, but rather in the next step.

8. Detection of Positive Droplets

Since each individual partitioned PCR is brought fully to endpoint before any measurement of fluorescence is performed, each individual droplet will be either a fully fluorescent droplet or will contain virtually no fluorescence at all. This enables the simple enumeration of all positive (fluorescent) and negative (non-fluorescent) droplets.

9. Analysis

Because the upstream RT-PCR targeted a 1:1 RNA:cDNA ratio, each positive droplet should represent a single originating RNA transcript. This interpretation depends on the number of individual droplets far exceeding the number of target cDNA molecules. In the new process, at one extreme we consider the possibility of a single CTC being isolated and lysed, releasing some number of RNA transcripts which are then reverse-transcribed 1:1 into cDNA, partitioned, PCR-amplified, and enumerated.

We estimate that in the case of a moderately expressed gene, such as the KLK3 gene in prostate cancer cells, each cell contains approximately 80-120 copies of KLK3 mRNA. The Biorad QX200 ddPCR System generates 20,000 droplets, which ensures that for small numbers of isolated CTCs and moderately-expressed target genes there will never be more than one target cDNA molecule per droplet. On the other hand, in cases where the numbers of CTCs reach dozens or hundreds, for moderately-expressing genes there will likely be multiple copies of target cDNA per droplet. In such cases, approximate numbers of originating transcript can be estimated using Poisson statistics.

Novel Gene Panels to Enable Lineage-Specific Identification of CTCs

As discussed above, the identification of gene transcripts that are highly specific for cancer cells within the context of surrounding normal blood cells is central to the new methods. While many genes are known to be more highly expressed in cancer cells, the vast majority of these genes also typically have at least limited expression in normal tissues, including blood. Given the extraordinary sensitivity required for this assay, complete absence of signal in normal blood cells is essential for high confidence identification of tumor cells in the bloodstream.

Candidate tumor-specific transcripts used to detect CTCs in blood are first selected by analyzing publicly available gene expression data sets derived from breast, prostate, lung, pancreas, and liver cancers and melanoma, as well as our lab-generated single cell RNASeq data from CTCs isolated from breast, prostate and pancreatic cancer patients and mouse models of these cancers. Transcripts whose expression is restricted to tumors and absent or undetectable in blood components are chosen for further downstream analysis. Demonstrating and validating total absence of expression (with the highest level of sensitivity, i.e., Digital PCR assays) in normal blood cells is important. In general, we found that only ~10% of candidate genes predicted based on computational models or RNA Seq data are truly negative in human blood samples.

In particular, candidate tumor-specific mRNA transcripts for the detection of CTCs were initially identified through the analysis of gene expression data sets (microarray and RNA-Seq) derived previously for human breast, prostate, lung, pancreas, hepatocellular, and melanoma cancers. Specific publically available data sets used for this analysis include The Cancer Genome Atlas (TCGA) (The Cancer Genome Atlas, available online at tcga-data.nci.nih.gov/tcga/tcgaHome2.jsp) and the Cancer Cell Line Encyclopedia (CCLE) (available online at broadinstitute.org/ccle/home; see also, Barretina et al., The Cancer Cell Line Encyclopedia enables predictive modelling of anticancer drug sensitivity, *Nature* 483:603-607 (2012)). In addition, single-cell RNA-seq gene expression data from CTCs isolated from human patients with breast, prostate, and pancreatic cancers were analyzed (GEO accession numbers GSE51827, GSE60407, and GSE67980) (Aceto et al., Circulating tumor cell clusters are oligoclonal precursors of breast cancer metastasis, *Cell,* 158:1110-1122 (2014); Ting et al., Single-Cell RNA Sequencing Identifies Extracellular Matrix Gene Expression by Pancreatic Circulating Tumor Cells, *Cell Rep,* 8:1905-1918 (2014); and Miyamoto et al., RNA-Seq of single prostate CTCs implicates noncanonical Wnt signaling in antiandrogen resistance, *Science* 349:1351-1356 (2015). Tumor specific transcripts identified through these databases were then compared to human leukocyte RNA-Seq gene expression data (GEO accession numbers GSE30811, GSE24759, GSE51808, GSE48060, GSE54514, and GSE67980). Transcripts that displayed significant differential expression, with high expression in tumors and low or undetectable expression in leukocytes, were then selected for further downstream analysis. Moreover, a literature search was performed to select additional candidate tumor-specific transcripts. Between 50 and 100 candidate genes were selected for each type of human cancer.

For each candidate gene within each specific cancer type, two to four sets of PCR primers were designed to span regions across the target transcript. Primers are synthesized by IDT (Integrated DNA Technologies), probes are labeled with FAM or HEX, ZEN, and IABkFQ to create a probe targeting the middle of the amplicon. Unique features of our PCR primer design methodology necessary for the successful application of digital PCR-based mRNA transcript detection in human CTCs include the following: 1) the specific targeting of the 3' end of each mRNA transcript, given the proclivity of cellular mRNA transcripts to degrade from the 5'-end, particularly in unfixed, fragile cells such as CTCs; 2)

the design of primers to generate amplicons that span introns in order to exclude the unintentional amplification of contaminating genomic DNA, for example from excess contaminating leukocytes in the enriched CTC mixture; and 3) the design of primers to inclusively amplify multiple splice variants of a given gene, given the uncertainty in some cases regarding the clinical relevance of specific splice variants.

The specificity of the primers was first tested by qRT-PCR using cDNA derived from cancer cell lines (representing breast, prostate, lung, pancreas, and liver cancers and melanoma). For each type of human cancer, 2 to 5 established cancer cell lines were cultured and used for initial testing to evaluate PCR primer performance and assess for expression of the target transcript in the specified cancer. To provide an initial test of specificity, the same primers were used to evaluate expression of the target transcript in leukocytes from healthy individuals who do not have a diagnosis of cancer. Leukocytes from a minimum of five different healthy individuals were tested in this phase of testing (mixture of male and female individuals—this was dependent on the type of cancer; i.e. candidate prostate cancer and breast cancer genes required the use of male or female healthy donors only, respectively).

Leukocytes from healthy individuals were isolated from whole blood using Cell Preparation Tubes with Sodium Heparin (CPT) (Becton, Dickinson, and Co., NJ) following product insert instructions. RNA extraction and first-strand cDNA synthesis was performed for cancer cell lines and isolated leukocytes using standard methods. The specificity of expression of each gene (using 2 to 4 distinct sets of primers for each gene) was tested using qRT-PCR (cell line cDNA as positive controls, leukocyte cDNA from healthy donors as negative controls, and water as an additional negative control). Transcripts present in cancer cell lines, but absent in leukocytes based on qRT-PCR testing were then selected for further validation by droplet digital PCR. The selection criteria to pass this stage of testing were highly stringent, and required qRT-PCR signal to be present in at least one cancer cell line and absent in all healthy donor leukocyte samples tested.

Target transcripts and specific primer pairs that passed the qRT-PCR stage of testing were further validated using droplet digital PCR. For this stage of testing, the CTC-iChip (see, e.g., Ozkumur et al., "Inertial focusing for tumor antigen-dependent and -independent sorting of rare circulating tumor cells," Sci Transl Med, 5, 179ra147 (2013) was used to process whole blood samples donated by healthy individuals. The CTC-iChip performs negative depletion of red blood cells, platelets, and leukocytes from whole blood, and generates a sample product that is enriched for cells in the blood that do not express leukocyte markers, including CTCs (which should not be present in healthy individuals). For each blood sample, the product from the CTC-iChip was supplemented with an RNA stabilization solution (RNAlater®, Life Technologies) and processed for RNA extraction and cDNA synthesis using standard methods. Droplet digital PCR (Biorad, CA) was then used to quantitate the number of transcripts present in each sample based on the specific primer pairs being tested. Samples assessed by droplet digital PCR during this phase of testing included cDNA from cancer cell lines, leukocyte cDNA from healthy donors processed through the CTC-iChip (at least four healthy individuals per primer pair being tested), and water as a negative control.

Criteria for passing droplet digital PCR testing were stringent, and included: 1) the presence of transcript signal in cancer cell lines (at least one cell line with >10 positive droplets); 2) excellent signal-to-noise ratio represented by separation of signal between positive and negative (empty) droplets; 3) minimal or absent droplet signal in healthy donors (<3 droplets per healthy donor); and 4) absent droplet signal in water (0 positive droplets).

Primers that amplified transcripts specifically in cell lines and not in leukocytes in the above droplet digital PCR testing were then subjected to detailed testing of sensitivity of signal. Using single cell micromanipulation, precise numbers of cancer cells (1, 5, 10, 25, and 50 cells) were spiked into whole blood donated by healthy individuals, and then processed through the CTC-iChip. Each sample was then processed as above for testing with droplet digital PCR, and evaluated for sensitivity to ensure the signal was sufficient for the desired clinical application.

The above stringent procedure of evaluating candidate genes and primers using qRT-PCR and droplet digital PCR resulted in a final primer list consisting of approximately 10% of the initial list of 50-100 candidate genes for each type of cancer (total of approximately 400 initial candidate genes). These primers are then further evaluated for signal in patient CTCs using blood samples donated by cancer patients undergoing cancer treatment at the MGH Cancer Center, collected under an IRB-approved clinical protocol. Key to this portion of the evaluation is a comparison with blood collected from healthy individuals without a diagnosis of cancer. The following Table 1 lists the primers and probes for that have been developed thus far using these methods for the specific detection of CTCs from patients with prostate, breast, hepatocellular, pancreatic, lung, and melanoma cancers using droplet digital PCR.

While a single gene for each cancer type could be used, the presence of multiple genes within each panel is useful both for sensitivity (CTCs are heterogeneous even within individual patients in their expression patterns) and specificity (detection of multiple gene signals confers added confidence that this represents a true cancer cell signature).

The gene list provided below in Table 1 includes transcripts that are unique to specific types of cancer (e.g., highly specific markers of prostate or breast or liver cancers), as well as genes that are shared by several cancer types, e.g., all epithelial cancer types (and thus may serve as pan-cancer markers), and genes that are induced in certain conditions (e.g., active androgen signaling in prostate cancer or active estrogen signaling in breast cancer). Thus, each type of cancer was assigned a specific panel of genes that is designed for optimal sensitivity, specificity, and clinically actionable information for the given cancer type.

In addition, primers described in Table 2 are designed to pre-amplify some of the genes listed in Table 1, while maintaining their high specificity. If STA is a method of choice, these nested primers become additional components of each cancer panel.

Gene Lists for Different Types of Cancers

The following Table 1 provides a list of names of genes (with (Genbank ID) and Sequence Identification numbers (SEQ ID NO)), along with cancer types for which they are selective (Br: breast, Lu: lung, Li: liver, Pr: prostate, Panc: pancreatic, Mel: melanoma). In addition, optimized primer sets are listed for each gene (primers 1 and 2), along with the composition of the fluorescent primer probes (e.g., 6-FAM™ (blue fluorescent label) or HEX™ (green fluorescent label) for tagged probes, and ZEN-31ABkFQ quencher) for optimal visualization of the digital PCR product.

TABLE 1

| Gene | Disease Group | Seq ID | Primer 2 | Seq ID | Primer 1 | Seq ID | Probe |
|---|---|---|---|---|---|---|---|
| AGR2 (10551) | Br, Lu, Li, Pr | 1 | CTG ACA GTT AGA GCC GAT ATC AC | 2 | CAA TTC AGT CTT CAG CAA CTT GAG | 3 | /56-FAM/ATG CTT ACG /ZEN/AAC CTG CAG ATA CAG CTC /3IABkFQ/ |
| ALDH1 A3 (220) | Br, Lu, Panc | 4 | GGT GGC TTT AAA ATG TCA GGA A | 5 | TGT CGC CAA GTT TGA TGG T | 6 | /56-FAM/TTT TCA CTT /ZEN/CTG TGT ATT CGG CCA AAG C/3IABkFQ/ |
| CADPS2 (93664) | Br, Li, Lu, Mel | 7 | CTC TGC ATT TTT GGA CAT AGG AG | 8 | GCC TTG CAC TTC CAT TAT GAC | 9 | /56-FAM/TCC GAC GTG /ZEN/GTA CTG TCA TT ACC T/3IABkFQ/ |
| CDH11 (1009) | Br, Lu, Panc | 10 | GAG GCC TAC ATT CTG AAC GC | 11 | GTG GTT CTT TCT TTT GCC TTC TC | 12 | /56-FAM/CAT CCT CGC /ZEN/CTG CAT CGT CAT TCT /3IABkFQ/ |
| CDH3 (1001) | Br, Li, Mel | 13 | GTT TCA TCC TCC CTG TGC TG | 14 | GCT CCT TGA TCT TCC GCT TC | 15 | /56-FAM/CTG CTG GTG /ZEN/CTG CTT TTG TTG GT/3IABkFQ/ |
| COL8A1 (1295) | Br, Lu | 16 | GAT GCC CCA CTT GCA GTA | 17 | CCT CGT AAA CTG GCT AAT GGT | 18 | /56-FAM/AGT ATC CAC /ZEN/ACC TAC CCC AAT ATA TGA AGG AAA /3IABkFQ/ |
| EGFR (1956) | Br, Lu, Li, Panc | 19 | CTG CTG CCA CAA CCA GT | 20 | TTC ACA TCC ATC TGG TAC GTG | 21 | /56-FAM/CTG CCT GGT /ZEN/CTG CCG CAA AT C/3IABkFQ/ |
| FAT1 (2195) | Br, Lu, Li, Mel, Pr, Panc | 22 | GAT CCT TAT GCC ATC ACC GT | 23 | ATC AGC AGA GTC AAT CAG TGA G | 24 | /56-FAM/TCT TGT CAG /ZEN/CAG CGT TCC CGG /3IABkFQ/ |
| FAT2 (2196) | Br, Lu | 25 | CCT GGA TGC TGA CAT TTC TGA | 26 | TCC TCC ACT CAT CTC CAA CT | 27 | /56-FAM/ACC TGC TAC /ZEN/ATC ACA GAG GGA GAC C/3IABkFQ/ |
| FOLH1 (2346) | Pr | 28 | CAA TGT GAT AGG TAC TCT CAG AGG | 29 | TGT TCC AAA GCT CCT CAC AA | 30 | /56-FAM/ATG AAC AAC /ZEN/AGC TGC TCC ACT CTG A/3IABkFQ |
| HOXB13 (261729) | Br, Lu, Pr | 31 | CAG CCA GAT GTG TTG CCA | 32 | CTG TAC GGA ATG CGT TTC TTG | 33 | /56-FAM/CAG CAT TTG /ZEN/CAG ACT CCA GCG G/3IABkFQ/ |
| KLK2 (3817) | Pr | 34 | GCT GTG TAC AGT CAT GGA TGG | 35 | GTC TTC AGG CTC AAA CAG GT | 36 | /56-FAM/TGG CTA TTC /ZEN/TTC TTT AGG CAA TGG GCA /3IABkFQ/ |
| KLK3 (354) | Pr | 37 | GTG TGC TGG ACG CTG GA | 38 | GTG ATA CCT TGA AGC ACA CCA TTAC | 39 | /56-FAM/AAA GCA CCT /ZEN/GCT CGG GTG ATT CT/3IABkFQ/ |
| LSAMP (4045) | Mel | 40 | CAC ATT TGA GTG AAG CTT GTC G | 41 | GCG GAT GTC AAA CAA GTC AAG | 42 | /56-FAM/TCC AAG AGC /ZEN/AAT GAA GCC ACC ACA /3IABkFQ/ |
| MAGE A6-RM1 (4105) | Mel | 43 | GAA GGA GAA GAT CTG CCA GTG | 44 | GCT GAC TCC TCT GCT CAA G | 45 | /56-FAM/TTG CCC TGA /ZEN/CCA GAG TCA TCA TGC /3IABkFQ/ |

TABLE 1-continued

| Gene | Disease Group | Seq ID | Primer 2 | Seq ID | Primer 1 | Seq ID | Probe |
|---|---|---|---|---|---|---|---|
| MET (4233) | Br, Li, Lu, Panc | 46 | CCA GTA GCC TGA TTG TGCAT | 47 | TGT CAG TGA TTC TGT TCA AGG A | 48 | /56-FAM/AGT CAT AGG /ZEN/AAG AGG GCA TTT TGG TTG T/3IABkFQ/ |
| MLANA (2315) | Mel | 49 | ACT CTT ACA CCA CGG CTG A | 50 | CCA TCA AGG CTC TGT ATC CAT | 51 | /56-FAM/AAG ACT CCC /ZEN/AGG ATC ACT GTC AGG A/3IABkFQ/ |
| NPY1R (4886) | Br, Lu | 52 | GGA TCT GAG CAG GAG AAA TAC c | 53 | GAA TTC TTC ATT CCC TTG AAC TGA | 54 | /56-FAM/AGC AGG AGC /ZEN/GAA AAA GAC AAA TTC CAA AG/3IABkFQ/ |
| OCLN (100506658) | Br, Lu, u | 55 | AAG ATG GAC AGG TAT GAC AAG TC | 56 | ACT CTT TCC ACA TAG TCA GAT GG | 57 | /56-FAM/TGC AGA CAC /ZEN/ATT TTT AAC CCA CTC CTC G/3IABkFQ/ |
| PDZRN3 (23024) | Mel | 58 | TGT CCT GGC TGT TCA TTC TG | 59 | TGG ATC CCT ATC TCT TGC CA | 60 | /56-FAM/AGC TCC TCC /ZEN/CTG TCC ATC TCC T/3IABkFQ/ |
| PGR (5241) | Br | 61 | GGC AAT TGG TTT GAG GCA A | 62 | GGA CTG GAT AAA TGT ATT CAA GCA | 63 | /56-FAM/ACA AGA TCA /ZEN/TGC AAG TTA TCA AGA AGT TTT GTA AGT T/3IABkFQ/ |
| PKP3 (11187) | Br, Li, Lu, Panc | 64 | CTG GTG GAG GAG AAC GG | 65 | GGT CGC TGG ATG AAA GGT T | 66 | /56-FAM/AGT GTC CGC/ZEN/AGC AGC TCG AA/3IABkFQ/ |
| PMEL (6490) | Mel | 67 | CAG GCA TCG TCA GTT TCCT | 68 | ACA CAA TGG ATC TGG TGC TAA | 69 | /56-FAM/TTT GGC TGT /ZEN/GAT AGG TGC TTT GCT G/3IABkFQ/ |
| PPL (5493) | Br, Lu, Li | 70 | GAG GAG AGA ATC AAC AAA CTG c | 71 | AGG TTC AGG TAC TCC TTC CAG | 72 | /56-FAM/AGG AAC TCC /ZEN/ATT GAG GCG CAC AT/3IABkFQ/ |
| RXRG (6258) | Mel | 73 | ATA CTT CTG CTT GGT GTA GGC | 74 | AGC CAT TGT ACT CTT TAA CCC A | 75 | /56-FAM/CTC T GGT /ZEN/GGA GAC TCT GCG AGA/3IABkFQ/ |
| RND3 (390) | Br, Lu, Li, Mel, Panc | 76 | CCG AGA ATT ACG TTC CTA CAG TG | 77 | GCG GAC ATT GTC ATA GTA AGG A | 78 | /56-FAM/ACG GCC AGT /ZEN/TTT GAA ATC GAC ACA C/3IABkFQ/ |
| S100A2 (6273) | Br, Lu, Li, Panc | 79 | CTG CCT TGC TCT CCT TCC | 80 | CTT ACT CAG CTT GAA CTT GTC G | 81 | /56-FAM/ACC TGG TCT /ZEN/GCC ACA GAT CCA TG/3IABkFQ/ |
| SCGB2A1 (4246) | Br | 82 | ACT TCC TTG ATC CCT GCC A | 83 | GTC TTT TCA ACC ATG TCC TCC A | 84 | /56-FAM/CCATGA AGC /ZEN/TGC TGA TGG TCC TCA/3IABkFQ/ |
| SFRP1 (6422) | Mel | 85 | CAA TGC CAC CGA AGC CT | 86 | CTT TTA TTT TCA TCC TCA GTG CAA AC | 87 | /56-FAM/TGT GAC AAC /ZEN/GAG TTG AAA TCT GAG GCC /3IABkFQ/ |
| SOX10 (6663) | Mel | 88 | CTT GTC ACT TTC GTT CAG CAG | 89 | CTT CAT GGT GTG GGC TCA | 90 | /56-FAM/TTG TGC AGG /ZEN/TGC GGG TAC TGG/3IABkFQ/ |

TABLE 1-continued

| Gene | Disease Group | Seq ID | Primer 2 | Seq ID | Primer 1 | Seq ID | Probe |
|---|---|---|---|---|---|---|---|
| SCHLAP1/ SET4 (101669767) | Pr | 91 | TCC TTG GAT GAC TCT CCC TAC | 92 | AGA TAC CAC CTC CCT GAA GAA | 93 | /56-FAM/CCA ATG ATG /ZEN/AGG AGC GGG ATG GAG /3IABkFQ/ |
| SCHLAP1 SET S | Pr | 94 | AGA GGT TTA ATG GGC TCA CAG | 95 | CTC TGG TCT GTC GTC ATG TAA G | 96 | /56-FAM/ACA TGC CTT /ZEN/TCA CCT TCT CCA CCA /31ABkFQ/ |
| AMACR (23600) | Pr | 97 | CAC ACC ACC ATA CCT GGA TAAT | 97 | TCA CTT GAG GCC AAG AGT TC | 99 | /56-FAM/AGA AAC GGA /ZEN/GGT CCA GCC AAG TTC /3IABkFQ/ |
| Variant7/ SET1 (367) | Pr | 100 | CTT TCT TCA GGG TCT GGT CAT T | 101 | CTT GTC GTC TTC GGA AAT GTT ATG | 102 | /56-FAM/AAG CAG GGA /ZEN/TGA CTC TGG GAG AAA /31ABkFQ/ |
| AR Variant 7 SET 3 | Pr | 103 | GAG GCA AGT CAG CCT TTCT | 104 | TGT CCA TCT TGT CGT CTT CG | 105 | /56-FAM/TGA AGC AGG /ZEN/GAT GAC TCT GGG AGA /3IABkFQ/ |
| AR Variant 12 SET: | Pr | 106 | GCT CAC CAT GTG TGA CTT GA | 107 | TGG GAG AGA GAC AGC TTG TA | 108 | /56-FAM/TGA TTG CGA /ZEN/GAG AGC TGC ATC AGT /31ABkFQ/ |
| AR Variant 12 SET | Pr | 109 | GAA AGT CCA CGC TCA CCAT | 110 | GCA GCC TTG CTC TCT AGC | 111 | /56-FAM/TGA TTG CGA /ZEN/GAG AGC TGC ATC AGT /31ABkFQ/ |
| UGT2B 15 SET 1(7366) | Pr | 112 | CTC TGC ACA AAC TCT TCC ATT TC | 113 | TTT CCT CGC CCA TTC TTA cc | 114 | /56-FAM/TTG GCT GGT /ZEN/TTA CAG TGA AGT CCT CC/3IABkFQ/ |
| UGT2B 15 SET 5 | PR | 115 | GGA AGG AGG GAA CAG AAA TCC | 116 | GTG AGC TAC TGG CTG AAC TATT | 117 | /56-FAM/TGG CTA CAC /ZEN/ATT TGA GAA GAA TGG TGG A/31ABkFQ/ |
| AFP SET 1 (174) | Li | 118 | AGG AGA TGT GCT GGA TTG TC | 119 | TCT GCA TGA ATT ATA CAT TGA CCAC | 120 | /56-FAM/AAT GCT GCA /ZEN/AAC TGA CCA CGC TG/31ABkFQ/ |
| AFP SET 2 | Li | 121 | ACT GCA GAG ATA AGT TTA GCT GAC | 122 | TCA CCATIT TGC TTA CTT CCT TG | 123 | /56-FAM/TTG CCC AGT /ZEN/TTG TTC AAG AAG CCA /3IABkFQ/ |
| STEAP2 (261729) | Br, Lu, Pr, Panc | 124 | CAT GTT GCC TAC AGC CTC T | 125 | TCT CCA AAC TTC TTC CTC ATT cc | 126 | /56-FAM/ACA TGG CTT /ZEN/ATC AGC AGG TTC ATG CA/31ABkFQ/ |
| TEAD3 (7005) | Br, Lu, u | 127 | GAA GAT CAT CCT GTC AGA CGA G | 128 | CTT CCG AGC TAG AAC CTG TAT G | 129 | /56-FAM/AGC GTG CAA /ZEN/TCA ACT CAT TTC GGC /3 1ABkFQ/ |
| TFAP2C (7022) | Br, Lu, Mel | 130 | GAT CAG ACA GTC ATT CGC AAA G | 131 | GAC AAT CTT CCA GGG ACT GAG | 132 | /56-FAM/ACA GGG GAG /ZEN/GTT CAG AGG GTT CTT /3IABkFQ/ |
| TMPRSS 2 (7113) | Pr | 133 | CCC AAC CCA GGC ATG ATG | 134 | TCA ATG AGA AGC ACC TTG GC | 135 | /56-FAM/ACC CGG AAA /ZEN/TCC AGC AGA GCT /31ABkFQ/ |

TABLE 1-continued

| Gene | Disease Group | Seq ID | Primer 2 | Seq ID | Primer 1 | Seq ID | Probe |
|---|---|---|---|---|---|---|---|
| GPC3 (2719) | Li | 136 | TGC TGG AAT GGA CAA GAA CTC | 137 | GCT CAT GGA GAT TGA ACT GGT | 138 | /56-FAM/TCC TTG CTG /ZEN/CCT TTT GGC TGT ATC T/31ABkFQ/ |
| ALB (219) | u | 139 | CTT ACT GGC GTT TTC TCA TGC | 140 | CCA ACT CTT GTA GAG GTC TCA AG | 141 | /56-FAM/ACA TTT GCT /ZEN/GCC CAC TTT TCC TAG GT/31ABkFQ/ |
| G6PC SET 1 (2538) | Li | 142 | GGA CCA GGG AAA GAT AAA GCC | 143 | GCA AGG TAG ATT CGT GAC AGA | 144 | /56-FAM/ACA GCC CAG /ZEN/AAT CCC AAC CAC AAA /31ABkFQ/ |
| G6PC SET 2 | u | 145 | CAT TTT GTG GTT GGG ATT CTG G | 146 | GAT GCT GTG GAT GTG GCT | 147 | /56-FAM/CTG TCA CGA /ZEN/ATC TAC CTT GCT GCT CA/31ABKFQ/ |
| PRAME (23532) | Mel | 148 | GCC TTG CAC TTC CAT TAT GAC | 149 | CTC TGC ATT TTT GGA CAT AGG AG | 150 | /56-FAM/CAA GCG TTG /ZEN/GAG GTC CTG AGG C/31ABkFQ/ |
| AHSG (197) | Li | 151 | ATG TGG AGT TTA CAG TGT CTG G | 152 | AGC TTC TCA CTG AGT GTT GC | 153 | 56-FAM/CCA CAG AGG /ZEN/CAG CCA AGT GTA ACC /31ABkFQ/ |
| GPR143 (4935) | Mel | 154 | ACG GCT CCC ATC CTC CT | 155 | CCA CTA TGT CAC CAT GTA CCT G | 156 | /56-FAM/TTC GCC ACG /ZEN/AGA ACC AGC AGC /3IABkFQ/ |
| PTPRZ1 (5803) | Mel | 157 | TGC TCT GAC AAC CCT TAT GC | 158 | GGC TGA GGA TCA CTT TGT AGA | 159 | /56-FAM/AGG CCA GGA /ZEN/GTC TTT GCT GACATT/3IABkFQ/ |
| MUCL1 (118430) | Br | 160 | CAT CAG CAG GAC CAG TAG C | 161 | TGT CTG TGC TCC CTG ATCT | 162 | /56-FAM/ACT CCC AAG/ZEN/AGT ACC AGG ACT GCT /31ABkFQ/ |
| PIP (5304) | Br | 163 | TCA TTT GGA CGT ACT GAC TTG G | 164 | CTT GCT CCA GCT CCT GTTC | 165 | /SHEX/CCT GCT CCT /ZEN/GGT TCT GCC TG/31ABkFQ/ |
| PGR (5241) | Br | 166 | GGT GTT TGG TCT AGG ATG GAG | 167 | ACT GGG TTT GAC TTC GTA GC | 168 | /56-FAM/AGT GGG CAG /ZEN/ATG CTG TAT TTT GCA C/31ABkFQ/ |
| TFAP2C (7022) | Br, Lu | 169 | GTG ACT CTC CTG ACA TCC TTA G | 170 | CCA TCT CAT TTC GTC CTC CAA | 171 | /56-FAM/TTC GGC TTC /ZEN/ACA GAC ATA GGC AAA GT/3IABkFQ/ |
| SCGB2 A1 (4246) | Br | 172 | ACT CTG AAA AAC TTT GGA CTG ATG | 173 | TCT AGC AAT CAA CAG ATG AGT TCT | 174 | /56-FAM/TAG CCC TCT /ZEN/GAG CCA AAC GCC /3IABKFQ/ |
| FAT1 (2195) | Br, Lu, Pr | 175 | AGC TCC TTC CAG TCC GAAT | 176 | GTC TGC TCA TCA ATC ACC TCA | 177 | /56-FAM/ATC CCA GTG /ZEN/ATA CCC ATT GTC ATC GC/31ABkFQ/ |
| FAT2 (2196) | Br, Lu, Pr | 178 | GGA CAG AGA GAA CAA GGA TGA AC | 179 | TGT GGG AGA ATA TAG GTG GAT TG | 180 | /56-FAM/TGG AGG TGA /ZEN/CTG TGC TGG ACA ATG /31ABkFQ/ |

TABLE 1-continued

| Gene | Disease Group | Seq ID | Primer 2 | Seq ID | Primer 1 | Seq ID | Probe |
|---|---|---|---|---|---|---|---|
| RND3 (390) | Br, Lu | 181 | GCT TTG ACA TCA GTA GAC CAG AG | 182 | CTG TCC GCA GAT CAG ACT TG | 183 | /56-FAM/ACA GTG TCC /ZEN/TCA AAA GTG GAA AGG GTG A/3IABkFQ/ |
| SFTPB (6439) | Lu | 184 | CCT GGA AAA TGG CCT CCTT | 185 | CAT TGC CTA CAG GAA GTC TGG | 186 | /56-FAM/CCG ATG ACC /ZEN/TAT GCC AAG AGT GTG AG/3IABkFQ/ |
| SCGB3A2 (117156) | Lu | 187 | CCA GAG GTA AAG GTG CCA AC | 188 | TCC CAG ATA ACT GTC ATG AAG C | 189 | /56-FAM/AAG GCA GTA /ZEN/GCA GAG TAA CTA CAA AGG /3IABkFQ/ |
| SERPINA3 (12) | Br, Lu | 190 | CCT CAA ATA CAT CAA GCA CAG C | 191 | GGA AGC CTT CAC CAG CAA | 192 | /56-FAM/TAG CAG TCT /ZEN/CCC AGG TGG A/3IABkFQ/ |
| SFRP2 (6423) | Br, Lu | 193 | TTG CAG GCT TCA CAT ACC TT | 194 | GCC CGA CAT GCT TGA GT | 195 | /56-FAM/TTT CCC CAA /ZEN/GGA CAA CGA CCT TT/3IABkFQ/ |
| CRABP2 (1382) | Br, Lu | 196 | CTC TTG CAG CCA TTC CTC TT | 197 | CCC TTA CCC CAG TCA CTT CT | 198 | /S6-FAM/TTT CTT TGA/ZEN/CCT CTT CTC TCC TCC CCT /3IABkFQ/ |
| AQP4 (361) | Lu | 199 | TGG ACA GAA GAC ATA CTC ATA AAG G | 200 | GGT GCC AGC ATG AAT CCC | 201 | /56-FAM/CCG ATC CTT /ZEN/TGG ACC TGC AGT TAT CA/3IABkFQ/ |
| TMPRSS4 (56649) | Br, Lu | 202 | ATC TTC CCT CCA TTC TGC TTC | 203 | CAG TTC CCA CTC ACT TTC TCA G | 204 | /56-FAM/CTC ACT CCA /ZEN/GCC ACC CCA CTC/3IABkFQ/ |
| GREM1 (26585) | Lu | 205 | TTT TGC ACC AGT CTC GCT T | 206 | GCC GCA CTG ACA GTA TGA G | 207 | /56-FAM/CCT ACA CGG /ZEN/TGG GAG CCC TG/3IABkFQ/ |
| FOXF1 (2294) | Lu | 208 | CGA CTG CGA GTG ATA CCG CT | 209 | CTC TCC ACG CAC TCC CT | 210 | /56-FAM/CTG CAC CAG /ZEN/AAC AGC CAC AAC G/3IABkFQ/ |
| NKX2-1 (7080) | Lu | 211 | TGC CGC TCA TGT TCA TGC | 212 | CAG GAC ACC ATG AGG AAC AG | 213 | /56-FAM/CCC GCCATC/ZEN/TCC CGC TTCA/3IABkFQ/ |
| NKX2-1 (7080) | Lu | 214 | AAG ATG TCA GAC ACT GAG AAC G | 215 | CGA AGC CCG ATG TGG TC | 216 | /56-FAM/ATG TCG ATG /ZEN/AGT CCA AAG CAC ACG A/3IABkFQ/ |
| AFP (174) | Li | 217 | AGGAGATGTGCTGGATTGTC | 218 | TCTGCATGAATTATACATTGAC | 219 | /56-FAM/AAT GCT GCA /ZEN/AAC TGA CCA CGC TG/3IABkFQ/ |
| AHSG (197) | Li | 220 | ATGTGGAGTTTACAGTGTCTGG | 221 | AGCTTCTCACTGAGTGTTGC | 222 | /56-FAM/CCA CAG AGG /ZEN/CAG CCA AGT GTA ACC/3IABkFQ/ |
| ALB (213) | Li | 223 | GAG ATC TGC TTG AAT GTG CTG | 224 | CAA CAG AGG TTT TTC ACA GCAT | 225 | /56-FAM/AGA TAT ACT /ZEN/TGG CAA GGT CCG CCC /3IABkFQ/ |

TABLE 1-continued

| Gene | Disease Group | Seq ID | Primer 2 | Seq ID | Primer 1 | Seq ID | Probe |
|---|---|---|---|---|---|---|---|
| ALB (213) | Li | 226 | CAT GGT AGG CTG AGA TGC TTT | 227 | GAC GAT AAG GAG ACC TGC TTT G | 228 | /56-FAM/ACT TGT TGC /ZEN/TGC AAG TCA AGCTGC/3IABkFQ/ |
| ALB (213) | Li | 229 | GCG CAT TCT GGA ATT TGT ACT c | 230 | GCT ATG CCA AAG TGT TCG ATG | 231 | /56-FAM/ACC TCT TGT /ZEN/GGA AGA GCC TCA GAA /3IABkFQ/ |
| APOH (350) | Li | 232 | TGA TGG ATA TTC TCT GGA TGG C | 233 | CCT GAA TCT TTA CTC TCT CTC CTT G | 234 | /56-FAM/CCA GTT TCC /ZEN/CAG TTT GGT ACA TTC TAT TTC C/3IABkFQ/ |
| FABP1 (2168) | Li | 235 | GCA CTT CAA GTT CAC CAT CAC | 236 | ACC AGT TTA TTG TCA CCT TCC A | 237 | /56-FAM/AAC CAC TGT /ZEN/CTT GAC TTT CTC CCC TG/3IABKFQ/ |
| FGB (2244) | Li | 238 | ACA TCT ATT ATT GCT ACT ATT GTG TGT T | 239 | TGG GAG CCT CTT CTC TCT TC | 240 | /56-FAM/ACC CTC CTC /ZEN/ATT GTC GTT GAC ACC /3IABkFQ/ |
| FGG (2266) | Li | 241 | TTC ATT TGA TAA GCA CAC AGT CTG | 242 | ACC TTG AAC ATG GCA TAG TCT G | 243 | /56-FAM/TGC CAT TCC /ZEN/AGT CTT CCA GTT CCA C/3IABkFQ/ |
| GPC3 (2719) | Li | 244 | AATCAGC TCCGCTT CCTTG | 245 | TGCTTATC TCGTTGTC CTTCG | 246 | /56-FAM/TTC CAG GCG /ZEN/CAT CAT CCA CAT CC/3IABkFQ/ |
| RBP4 (5950) | Li | 247 | CAG AAG CGC AGA AGA TTG TAA G | 248 | TCT TTC TGA TCT GCC ATC GC | 249 | /56-FAM/AGG CTG ATC /ZEN/GTC CAC AAC GGT T/3IABkFQ/ |
| TF (7018) | Li | 250 | AGA AGC GAG TCC GAC TGT | 251 | CAC TGC ACA CCA TCT CAC A | 252 | /56-FAM/CCA GACACA/ZEN/GCC CCA GGA CG/3IABkFQ/ |

Note that PRAME is also named MAPE (Melanoma Antigen Preferentially Expressed In Tumors), OIP4 (Opa-Interacting Protein OIP4), and CT130 (Cancer/Testis Antigen 130).

The following Table 2 lists nested primers designed to specifically pre-amplify the regions targeted by primers listed in Table 1.

TABLE 2

| Primer name | Seq ID | Nested Forward | Seq ID | Nested Reverse |
|---|---|---|---|---|
| FAT1 | 253 | CAG ATG GAG GAG GAA GAT TCT G | 254 | GTA TAC TGC CTG GAG TTC TCT G |
| FAT2 | 255 | CTG GTT CAG GTC TCC ATT ACA G | 256 | GCT GTG ACT CTG AGC AAG TA |
| AGR2 | 257 | TGT CCT CCT CAA TCT GGT TTA TG | 258 | GAC AGA AGG GCT TGG AGA TTT |
| PKP3 | 259 | CGG TGG CGT TGT AGA AGA T | 260 | AGA AGA TCT CTG CCT CCG A |
| RND3 | 261 | CAA GAT AGT TGT GGT GGG AGA c | 262 | AGG GTC TCT GGT CTA CTG ATG |
| TFAP2C | 263 | TTTGGATTTACCGCTTGG G | 264 | GACTCCAGTGTGGGAGAG |

TABLE 2-continued

| Primer name | Seq ID | Nested Forward | Seq ID | Nested Reverse |
|---|---|---|---|---|
| S100A2 | 265 | GGG CCC ACA TAT AAA TCC TCA C | 266 | CTG CTG GTC ACT GTT CTC ATC |
| PRAME | 267 | CTTCGCGGTGTGGTGAA | 268 | GCTGTGTCTCCCGTCAAA |
| PIP | 269 | CTG GGA CAC ATT GCC TTC T | 270 | CCA CCA TGC ATT CTT TCA ATT CT |
| PGR | 271 | AAA CCC AGT TTG AGG AGA TGA G | 272 | CCC TGC CAA TAT CTT GGG TAA T |
| SCGB2A1 | 273 | ACA GCA ACT TCC TTG ATC CC | 274 | GCG GCA TCA CTG TCT ATG AA |
| MUCL1 | 275 | CCT TGC CTT CTC TTA GGC TTT | 276 | AGC AGT GGT TTC AGC ATC A |
| PGR | 277 | CAG ATA ACT CTC ATT CAG TAT TCT TGG | 278 | CTC TAA TGT AGC TTG ACC TCA TCT |
| TFAP2C | 279 | GAG AAG TTG GAC AAG ATT GGG | 280 | GCT GAG AAG TTC TGT GAA TTC TTT A |
| SCGB2A1 | 281 | GTT TCC TCA ACC AGT CAC ATA GA | 282 | AGT TGT CTA GCA GTT TCC ACA TA |
| FAT1 | 283 | GGG AAA GCC TGT CTG AAG TG | 284 | TCG TAG CCT CCA GGG TAA TAG |
| FAT2 | 285 | GTT ACA GGT CTC CTA TCT ACA GC | 286 | GCT CAG CCT CTC TGG AAG |
| RND3 | 287 | CTC TCT TAC CCT GAT TCG GAT G | 288 | GGC GTC TGC CTG TGA TT |
| SFTPB | 289 | CCT GAG TTC TGG TGC CAA CAA AG | 290 | GGG CAT GAG CAG CTT CAA |
| SCGB3A2 | 291 | CCA CTG GCT TGG TGG ATT T | 292 | TCA ACA GAA ATG CCC AGA GTT |
| SERPINA3 | 293 | CTT CTC CAG CTG GGC ATT | 294 | TGC TGT GGC AGC AGA TG |
| SFRP2 | 295 | CGG TCA TGT CCG CCT TC | 296 | GCG TTT CCA TTA TGT CGT TGT C |
| CRABP2 | 297 | CCC TCC TTC TAG GAT AGC G | 298 | AAC CCG GAA TGG GTG AT |
| AQP4 | 299 | AAACGGACTGATGTCACTGG | 300 | TGGACAGAAGACATACTCATAAAGG |
| TMPRSS4 | 301 | CCCACTGCTTCAGGAAACATA | 302 | GTCAGACATCTTCCCTCCATTC |
| GREM1 | 303 | GCCGCACTGACAGTATGA | 304 | CAGAAGGAGCAGGACTGAAA |
| FOXF1 | 305 | AGC GGC GCC TCT TAT ATC | 306 | GCG TTG AAA GAG AAG ACA AAC T |
| NKX2-1 | 307 | CTA CTG CAA CGG CAA CCT | 308 | GGG CCA TGT TCT TGC TCA |
| NKX2-1 | 309 | CAG ACT CGC TCG CTC ATT T | 310 | CCT CCA TGC CCA CTT TCT T |
| PIP | 311 | CCCAAGTCAGTACGTCCAAAT | 312 | GCCTAATTCCCGAATAACATCAA |
| AGR2 | 313 | GCT TTA AAG AAA GTG TTT GCT G | 314 | CTG TAT CTG CAG GTT CGT AAG |
| SOX10 | 315 | AAG TTC CCC GTG TGC ATC | 316 | CTC AGC CTC CTC GAT GAA |

TABLE 2-continued

| Primer name | Seq ID | Nested Forward | Seq ID | Nested Reverse |
|---|---|---|---|---|
| MAGEA6 | 317 | GTGAGGAGGCAAGGTTCTG | 318 | GGCTCCAGAGAGGGTAGTT |
| TFAP2C | 319 | TTTGGATTTACCGCTTGGG | 320 | GACTCCAGTGTGGGAGAG |
| PRAME | 321 | CTTCGCGGTGTGGTGAA | 322 | GCTGTGTCTCCCGTCAAA |
| GPR143 | 323 | ATC CTG CTG TAT CAC ATC ATG | 324 | CTG ACA GGT TTC AAA GAA CCT |
| PMEL | 325 | CCAGTGCCTTTGGTTGCT | 326 | CAAGAGCCAGATGGGCAAG |
| MLANA | 327 | TGCCAAGAGAAGATGCTCAC | 328 | CATTGAGTGCCAACATGAAGAC |
| PTPRZ1 | 329 | AAG AAG CTG CCA ATA GGG AT | 330 | TGT CCA GAG AGG TGG ATG |

Multiplex Digital Analysis of Gene Transcripts from CTC-Chip Products

To improve the detection of tumor-specific mRNA from minimal amounts of RNA derived from CTCs, we established a multiplex assay capable of testing many different gene transcripts from a minute amount of CTC-Chip product. This combines the higher sensitivity/specificity of using multiple independent genes, with the fact that the amount of input template is limited (and hence should not be diluted into multiple reactions). Our assay includes 4 genes per reaction, with each gene being resolved uniquely in 2-dimensional space by selecting different ratios of fluorescent conjugated primers. Thus, in a single reaction, we can independently measure 4 gene transcripts without having to dilute the template. For different cancers, we have gone as far as up to 4 different reactions (i.e., up to 20 different gene transcripts), and with application of nested RT-PCR digital assays, there is no limit to the number of reactions that can be performed.

This multiplex strategy achieves the ideal balance between analyzing multiple transcripts (and hence ensuring against heterogeneous variation in cancer cell expression patterns), but not diluting the input material by performing multiple independent PCR reactions. Depending on tumor types and the number of genes required for optimal signal, we have developed assays ranging from 2-4 multiplex reactions (each multiplex reaction testing for 4-genes). Thus, without undue dilution of input template, we can interrogate the product of a single CTC for expression of anywhere from 8 to 16 different genes. It is important to the assay to be able to add the signal from all of these genes (i.e. cumulative signal), while also having individual gene results (to optimize signal/noise at the individual gene level, and also gather information from specific signaling pathways that each gene interrogates—for example androgen signaling in prostate CTCs).

To display the results of the multiplex reaction in a single view (and hence differentiate amplification of each gene is isolation), we varied the concentrations of the two fluorescent probes (FAM (blue) and HEX (green)). By doing this, each individual gene amplification reaction has a unique combination of FAM/HEX signal that reflects the composition of the gene-specific primers, and hence identifies the gene-specific PCR product. In 2-dimensional space, we can illustrate the signal position of 4 different gene amplification products produced from a single multiplex reaction. As applied to digital PCR using droplets to encapsulate each PCR reaction, this method separates the targets into individual clusters by modifying the binary signal amplitude of positive droplets, which are displayed quantitatively. As predicted, this method allows both cumulative scoring of total signal for multiple genes (e.g., 16 markers in a total of 4 reactions), while also retaining the ability to quantify the signal from each individual gene target.

Specific results of testing are detailed in the examples below.

Applications of the d-CTC Assay Methods

The early detection of epithelial cancers at a time when they can be surgically resected or irradiated provides the best chance of cure, and the administration of adjuvant chemotherapy in the setting of minimal cancer dissemination is far more effective in achieving cure than the treatment of established metastatic disease. However, current efforts at early cancer detection suffer from lack of specificity. For instance widespread screening of men for prostate cancer, using serum PSA measurements is effective in uncovering early cancers, but it also identifies a much larger number of non-malignant prostate conditions (e.g., benign hypertrophy of the gland) or even cancers that are indolent and never destined to become invasive. As such, broad PSA screening is not recommended by public health organizations, because the number of complications (including deaths) from over-diagnosis match or even outweigh the calculated benefit in early cancer detection.

For other cancers, such as breast cancer, mammography is considered effective, but even then a large number of breast biopsies are performed to diagnose each true malignancy. For lung cancer, the recently recommended low dose CT scanning of individuals with a heavy cigarette smoking history is also likely to detect hundreds of innocent radiographic abnormalities for each true malignancy.

It is in this context that the addition of a blood-based ultra-sensitive readout for the presence of cancer cell-derived signatures would provide the required specificity. The d-CTC assays described herein can be used for both initial screening and as a confirmation of earlier screenings at a later time. For example, in some cases the assays can be used as a second-line test to validate a highly sensitive, but nonspecific screening test (e.g., PSA in prostate cancer). In other settings for which a cancer is highly lethal, but no screening approach currently exists (e.g., pancreatic cancer), routine periodic blood screening using the assays described herein may become the norm to monitor a patient's status or condition over time.

The new d-CTC readouts are also highly relevant to the serial monitoring of patients, e.g., seemingly healthy patients with a family history and/or genetic markers of a specific type of cancer, or patients with advanced or metastatic cancer. Imaging of CTCs is expensive and relatively insensitive, in that intact cells that stain appropriately for all required markers produce a single signal. The use of the new d-CTC assays described herein, in which each CTC (no matter how intact or pre-apoptotic) can give rise to hundreds of molecular signals, dramatically enhances the ability to detect and monitor CTCs in patients with known cancer, and to quantitatively monitor and analyze their response to therapeutic interventions. Beyond scoring for cell numbers through molecular markers, specific interrogation of mutations or cancer-associated rearrangements (e.g., EML4-ALK in lung cancer) can be achieved with comparable sensitivity.

In addition to providing a digital (quantitative) measure of CTCs present within a blood sample, the new d-CTC assay also allows analysis of specific signaling pathways that are unique to the tumor cells in the blood. For instance, a subset of prostate lineage-specific genes are driven by androgen signaling (such as PSA), while another subset are repressed by androgen signaling (such as PSMA). By analyzing these genes together, we can ascertain the status of androgen signaling within CTCs. Similarly, in breast cancer, expression of estrogen-responsive genes (such as progesterone receptor) provides a measure of the status of the estrogen-responsive pathway within CTCs. These measurements are particularly important in that therapeutic interventions in both prostate and breast cancers are derived to target the androgen and estrogen receptors, respectively. Thus, defining the total number of CTC signal in the blood, simultaneously with information about the effectiveness of the therapeutic agent in targeting and shutting off the critical pathway is important for therapeutic monitoring.

As discussed in the examples below, the new methods described herein are illustrated in prostate cancer, where the anti-androgenic agent abiratorone (e.g.,) ZYTIGA® is effective in suppressing cancer progression, particularly in tumors that are still dependent on the androgen pathway.

EXAMPLES

The invention is further described in the following examples, which do not limit the scope of the invention described in the claims.

Example 1

Preliminary Testing and Validation of the Digital CTC Assay

To test the feasibility of CTC-Chip-Droplet assay, we first selected several transcripts that are specifically expressed in prostate tumor cells, but are absent in contaminating leukocytes. These were the prostate lineage specific markers KLK3 (kallikrein-related peptidase; aka Prostate Specific Antigen, or PSA), FOLH1 (Folate Hydrolase; aka Prostate Specific Membrane Antigen, or PSMA) and AMACR (alpha-methylacyl-CoA racemase), as well as EpCAM (Epithelial Cell Adhesion Molecule). PCR conditions were optimized using intron-spanning primers and ZEN double-quenched FAM-labelled probes from Integrated DNA Technologies (Coralville, Iowa) following standard qPCR protocols. These conditions were first tested with encapsulated cDNA from admixtures of cancer cells and leukocytes in order to explore the dynamic range of the system. Next, using manual isolation techniques for individually selecting cells, 0, 3, 6, 12, 25, and 125 prostate cancer LNCaP cells were progressively spiked into individual 5 ml aliquots of HD blood, followed by CTC-iChip processing, RT-PCR and droplet encapsulation using the RainDrop system. We chose KLK3 as the target transcript for this experiment as it is predicted to be modestly abundant. Using an intensity threshold of 5,000, we found that as few as 3 cells worth of KLK3 transcript were readily detected at approximately 250 droplets.

Based on these preliminary data, we tested the CTC-Chip Droplet assay in patients with metastatic and localized prostate cancer versus healthy controls. Each sample was run through the iChip, then CTC-containing product was run through droplet RT-PCR using the four prostate markers mentioned above: KLK3, AMACR, FOLH1 and EpCAM. Patients with either local or metastatic prostate cancer produced significantly higher positive droplet counts as compared to HD controls.

FIG. 1A shows cDNA dilutions prepared from total RNA of LNCaP prostate cancer cells, mixed with leukocytes and analyzed by droplet PCR using two different prostate primer sets. The results represent several purities and show good response of positive droplet number across this range.

FIG. 1B shows manually isolated LNCaP cells spiked into HD blood samples, run through the iChip, and subjected to droplet RT-PCR (KLK3 primer set). The results show excellent sensitivity down to low numbers of target cells.

FIG. 1C shows the analysis of blood samples from healthy controls, patients with localized (resectable) prostate cancer and metastatic prostate cancer, processed through the CTC-iChip, subjected to RT-PCR and droplet analysis using three prostate-specific and one epithelial-specific biomarkers (KLK3, AMACR, FOLH1, EpCAM). The results are shown for the total number of droplets/ml for all four markers combined.

These results suggest that the application of a droplet-based PCR readout to the CTC-iChip greatly enhances its sensitivity in detecting virtually all CTCs present in a biological specimen. Taken together, the CTC-iChip and Droplet-PCR represent two powerful microfluidic technologies that are highly compatible with each other and can be integrated in-line to create a new and highly sensitive and accurate biological assay.

Example 2

Digital CTC Assay Protocol

This example provides a general digital CTC assay protocol that can be used for the methods described herein. Different aspects of this general protocol were used in some of the Examples described herein. For example, Approach 1 of Step 3 of the protocol described below (relating to RNA purification to cDNA synthesis), was used to generate data for FIGS. 15A to 15C. Approach 2 in Step 3 was used to generate data for FIGS. 19A to 24B.

1. Patient blood is run through I-Chip, version 1.3M or 1.4.5T. Sample is collected in a 15 mL conical tube on ice.

2. Sample is spun down at 4C. Supernatant is decanted and SUPERase™ In (DTT independent RNAse inhibitor)+ RNALater® Stabilization Solution (prevents RNA degradation by inhibiting RNAses) is added to the pellet. Sample is flash frozen and placed at −80 until further processing. Samples are stable at −80.

3. There are two different processing protocols for RNA purification to cDNA synthesis that were used in the examples described below.

Approach 1
a. Sample was thawed on ice.
b. Direct lysis of sample using detergents (NP40, Tween20).
c. Lysed sample was taken straight for cDNA synthesis (Superscript III).
d. After cDNA synthesis sample was purified via SPRI (Agencourt AMPure® XP beads) clean-up to clean up detergents and any nucleotides <100 bps.

Approach 2
a. Sample was thawed on ice.
b. Sample was processed on RNeasy Qiagen Micro Kit. Protocol has some slight variations compared to traditional Qiagen recommendations. Higher volumes of Buffer RLT (Lysis buffer) were used as well as higher ETOH concentrations. These modifications were made because of RNALater® addition to the sample.
c. After cDNA synthesis—sample was purified via SPRI (Agencourt AMPure XP beads) clean-up to clean up detergents and any nucleotides <100 bps.

4. cDNA (synthesized from Approach 1 or 2) can be processed in two different ways:
a. cDNA was used directly for ddPCR; or
b. cDNA was amplified used a Fluidigm BioMark™ Nested PCR approach (primers from genes used for nested PCR have been pre-validated). Amplified cDNA was diluted.

5. cDNA (from step 4a or 4b), Biorad Supermix™ for probes, primer or primers (for gene of interest; up to 4 different primers (FAM and HEX) can be multiplexed) were added in a total volume of 22 pl.

6. Droplets were generated (~15,000-18,000 droplets per well).

7. Droplet Sample were put in a PCR machine. The PCR conditions were different than Biorad recommendations. We used a step-down rather than a slow ramp to ensure that all droplets reach the same temperature. This is different than what both RainDance and Biorad uses. Better results (i.e., more signal and more separation between positive and negative droplets) can be obtained with the step-down rather than the gradient.

8. After the PCR, positive droplets were counted in a ddPCR machine.

9. Data is collected and analyzed using TIBCO® Spotfire® analysis software.

The reagents, reagent concentrations, and reaction volumes are provided below:

Reagents:
Biorad ddPCR™ Supermix for Probes (No dUTP)
IDT primers/probes (20× or 40×)
cDNA (ing/ul for cell lines)
Nuclease free water
Eppendorf semi-skirted 96 well plate (Only these plates work with the machine)
Testing Relevant Cell Lines
Per single reaction:

| ddPCR Supermix | 11.0 μl |
| Primer (20x) | 1.10 μl |

-continued

| cDNA (1 ng/ul) | 1.10 μl |
| Water | 8.80 μl |
| TOTAL | 22.0 μl per well |

A master-mix containing ddPCR supermix, cDNA, and water were aliquoted into wells and 1.1 μl of each the primer was added to each well and mixed well.

Patient Samples
Per single reaction for Individual Genes

| ddPCR Supermix | 11.0 μl |
| Primer (20x) | 1.1 μl |
| cDNA (patient) | Up to 9.9 μl (Balance with water if less) |
| TOTAL | 22.0 μl per well |

Per single multiplexed reaction for Multiple Genes

| ddPCR Supermix | 11.0 μl |
| Primer 1 (40x) | .55 μl |
| Primer 2 (40x) | .55 μl |
| Primer 3 (40x) | .55 μl |
| Primer 4 (40x) | .55 μl |
| cDNA (patient) | 8.8 μl |
| TOTAL | 22.0 μl per well |

When testing multiple patients against a gene-specific primer or multiplexing primers against multiple genes, a master-mix, which includes the ddPCR supermix and primers, was aliquoted into wells followed by addition of patient cDNA to each well and mixed well.

Example 3

Protocol for Gene Validation

The following protocol was used for selecting the specific marker genes listed in Table 1.
1. Transcripts that are unique to CTCs and not expressed in white blood cells (WBCs), leukocytes, etc. were mined bioinformatically—Primary tumor and CTC gene expression data was compared to WBC gene expression datasets to isolate transcripts that were present only in primary tumor and/or CTCs.
2. Transcripts that passed a threshold cutoff were validated by qPCR.
3. Primers were synthesized by IDT. Probes were labeled with FAM/ZEN/IBFQ.
4. qPCR validation required that every transcript be validated by at least two independent primer sets on two different cell lines, 5 healthy donors WBCs (isolated via CPT column) and water as a negative control. 50 cycles for qPCR were used to confirm that expression of a transcript was only present in cell lines and not in healthy donors.
5. Transcripts that passed qPCR validation were validated on ddPCR with cell lines and healthy donors passed through the CTC-iChip (with and without cell spiking).
6. Panels of transcripts were multiplexed (up to 4 different genes per reaction) depending on disease of interest.

Figure 2:
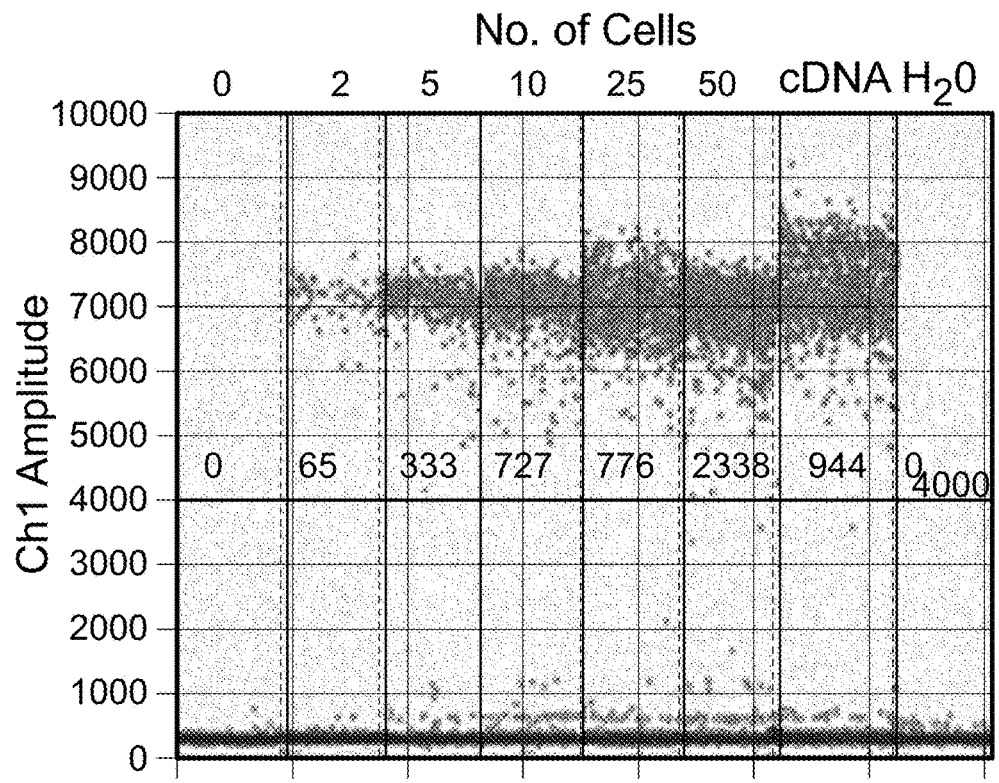
FIG. 2 is a signal intensity plot that shows KLK3 positive droplets derived from LNCAP prostate cancer cells spiked into blood and recovered using the CTC-iChip.

The validity of this strategy is shown below in a spiked cell experiment, in which a carefully measured number of tumor cells (from the LNCAP prostate cancer cell line) are individually micro-manipulated, added to control blood specimens, passed through the CTC-iChip and then analyzed by d-CTC assay as above. Increasing numbers of spiked cells show increasing numbers of digital signal as shown in FIG. 2, which illustrates the power of this protocol. FIG. 2 demonstrates the use of a single gene transcript (KLK3, also known as PSA, for prostate cancer) as a probe (in the assay, we use from 8-24 gene transcripts, thereby further increasing sensitivity). Here, we spike a calculated number of cancer cells (each cell is micro-manipulated, picked and introduced into 10 ml of control blood specimen). The blood is then processed through the CTC-Chip and subjected to digital readout as described above. No signal is observed in blood that has not been spiked with a single cancer cell. Introduction of 2 cells/10 ml of blood generates clear signal (65 positive droplets). In this case, the 10 CTC product was divided into 4 and run in quadruplicate, so the 64 droplets actually represent the digital signal derived from ¼ of a tumor cell.

Figure 3:
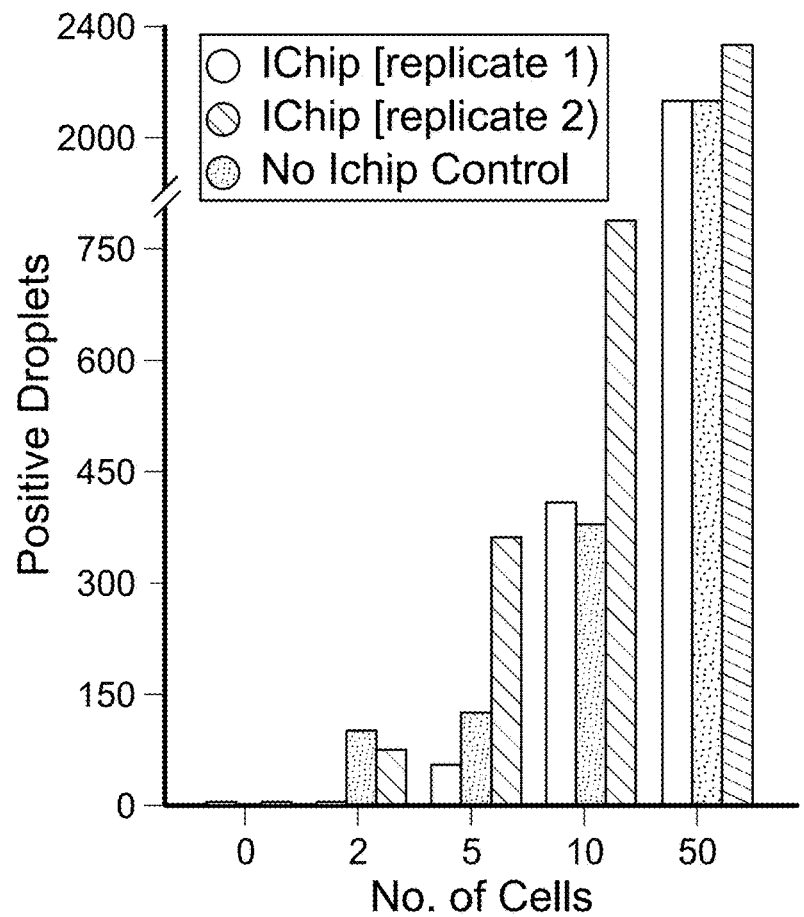
FIG. 3 is a bar graph that shows the minimal variation between experimental replicates and the retention of signal after sample processing through the CTC-iChip and shows increased detection sensitivity using the new assays described herein.

This assay is both highly sensitive and reproducible. As shown in FIG. 3, the digital signal in these spiked cell experiments shows high reproducibility (2 independent replicates shown here), and the same amount of signal is seen when cells are spiked into buffer (rather than blood) and directly analyzed (without CTC-Chip processing). Thus, there is virtually no loss of signal when a tumor cell is diluted into billions of normal blood cells and then "re-isolated" using the CTC-Chip prior to digital readout.

Example 4

Multiplex Digital Analysis of Gene Transcripts from CTC-Chip Product

We established a multiplex assay capable of testing many different gene transcripts from a minute amount of CTC-Chip product. This combined the higher sensitivity and specificity of using multiple independent genes, with the fact that the amount of input template is limited (and hence should not be diluted into multiple reactions). The new assays include multiple genes, e.g., 2, 3, 4, 6, 8, 10, or more genes per reaction, with each gene being resolved uniquely in 2-dimensional space by selecting different ratios of fluorescent conjugated primers. Thus, in a single reaction, one can independently measure 2, 3, 4, or more gene transcripts without having to dilute the template. For different cancers, one can run and analyze multiple different reactions (e.g., up to 20 different gene transcripts in four runs), and with application of nested RT-PCR digital assays, there is no limit to the number of reactions that can be performed.

To display the results of the multiplex reaction in a single view (and hence differentiate amplification of each gene is isolation), we varied the concentrations of the two fluorescent probes (FAM and HEX). By doing this, each individual gene amplification reaction has a unique combination of FAM/HEX signal that reflects the composition of the gene-specific primers, and hence identifies the gene-specific PCR product. In 2-dimensional space, we can illustrate the signal position of 4 different gene amplification products produced from a single multiplex reaction. As applied to digital PCR using droplets to encapsulate each PCR reaction, this method separates the targets into individual clusters by modifying the binary signal amplitude of positive droplets, which are displayed quantitatively. As predicted, this method allows both cumulative scoring of total signal for multiple genes (e.g., 16 markers in a total of 4 reactions), while also retaining the ability to quantify the signal from each individual gene target.

Probe 1: 100% FAM

Probe 2: 100% HEX

Probe 3: Mixture of FAM and HEX—sum up to 100%

Probe 4: Mixture of FAM and HEX—sum up to 100%

As shown in Tables 3 to 7, the following probe mixtures were used in the multiplex reactions:

TABLE 3

Multiplexing primers against 4 genes per reaction (Melanoma)
Reaction 1

| FAM | HEX | Primer | FAM int | HEX Int |
|---|---|---|---|---|
| 100% | 0 | Sox10 | 6000 | 0 |
| 70% | 30% | SFRP1 | 4000 | 2500 |
| 30% | 70% | RND3 | 4500 | 5500 |
| 0% | 100% | TFAP2C | 0 | 6000 |

Reaction 2

| FAM | HEX | Primer | FAM Int | HEX Int |
|---|---|---|---|---|
| 100% | 0 | PRAME | 11000 | 0 |
| 70% | 30% | MLANA | 8000 | 4000 |
| 30% | 70% | MAGEA6 | 5000 | 6000 |
| 0% | 100% | PMEL | 0 | 5500 |

Reaction 3

| FAM | HEX | Primer | FAM Int | HEX Int |
|---|---|---|---|---|
| 100% | 0 | PMEL | 7000 | 0 |
| 70% | 30% | MLANA | 6000 | 3000 |
| 30% | 70% | MAGEA6 | 4000 | 5000 |
| 0% | 100% | MET | 0 | 4500 |

TABLE 4

Multiplexing primers against 4 genes per reaction (Pan-Cancer/lineage)

| FAM | HEX | Primer | Exp. FAM Int | Exp. HEX Int |
|---|---|---|---|---|
| 100 | 0 | TFAP2C | 9000 | 0 |
| 60 | 40 | PGR | 5100 | 1800 |
| 35 | 65 | SCGB2A1 | 2205 | 7800 |
| 0 | 100 | CADPS2 | 0 | 5000 |

TABLE 5

Multiplexing primers against multiple genes per reaction (AR status in Prostate)
Multiplexing primers against 4 genes per reaction (Prostate)
Reaction 1

| FAM | HEX | Primer | Exp. FAM Int | Exp. HEX Int |
|---|---|---|---|---|
| 100 | 0 | TMPR2 | 5500 | 0 |
| 65 | 35 | FAT1 | 5525 | 1837.5 |
| 40 | 60 | KLK2 | 2440 | 2580 |
| 0 | 100 | STEAP2 | 0 | 4300 |

TABLE 5-continued

Reaction 2

| FAM | HEX | Primer | Exp. FAM Int | Exp. HEX Int |
|---|---|---|---|---|
| 100 | 0 | KLK3 | 6600 | 0 |
| 70 | 30 | HOXB13 | 4340 | 1320 |
| 50 | 50 | AGR2 | 4050 | 3050 |
| 0 | 100 | FOLH1 | 0 | 5200 |

TABLE 6

Multiplexing primers against 4 genes per reaction
Epithelial-Mesenchymal Transition (EMT)
Reaction 1

| FAM | HEX | Primer | Exp. FAM Int | Exp. HEX Int |
|---|---|---|---|---|
| 100 | 0 | PKP3 | 8000 | 0 |
| 75 | 25 | OCLN | 6000 | 1625 |
| 40 | 60 | CDH11 | 4000 | 3600 |
| 0 | 100 | 5100A2 | 0 | 5000 |

Reaction 2

| FAM | HEX | Primer | Exp. FAM Int | Exp. HEX Int |
|---|---|---|---|---|
| 100 | 0 | FAT1 | 8000 | 0 |
| 65 | 35 | FAT2 | 5200 | 1750 |
| 40 | 60 | COL8A1 | 3200 | 3900 |
| 0 | 100 | CDH3 | 0 | 6000 |

TABLE 7

Multiplexing primers against multiple genes per reaction

| Reaction | Gene-primer set | Avg intensity (FAM) | Avg intensity (HEX) | AR status |
|---|---|---|---|---|
| 1 | TMPRSS2 | 5500 | | ON |
| 1 | FAT1 | 8500 | 5250 | ? |
| 1 | KLK2 | 6100 | 4300 | ON |
| 1 | STEAP2 | 3350 | 4300 | ON |
| 2 | KLK3 | 6600 | | ON |
| 2 | FOLH1 | 6200 | 5200 | OFF |
| 2 | AGR2 | 8100 | 6100 | OFF |
| 2 | HOXB13 | 6500 | 4400 | OFF |

Validation and Testing

Figure 4:
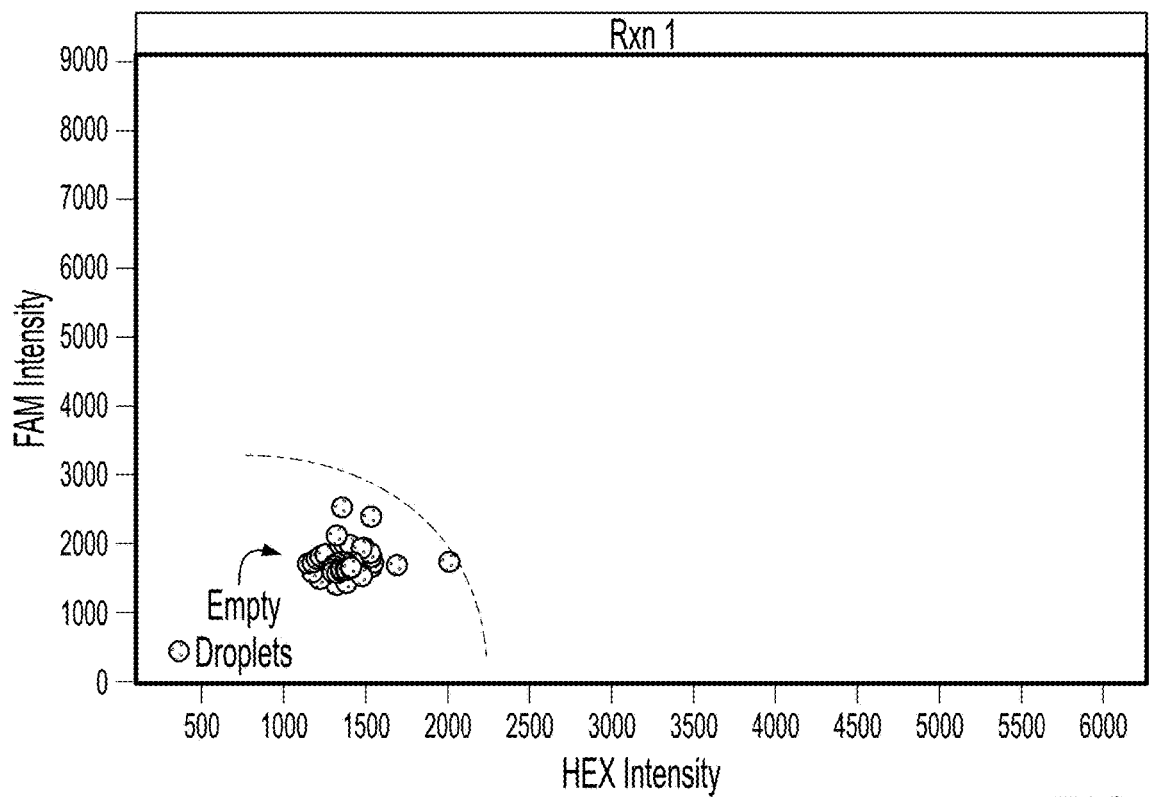
FIG. 4 is a signal intensity plot that shows the absence of four different cancer-specific marker-positive droplets in healthy donors using the new CTC digital droplet PCR assay methods described here ("CTC ddPCR" assay or simply "d-CTC" assay).

To validate and demonstrate the effectiveness of this multiplex strategy, we illustrated both the concept (using spiked cell experiments) and patient-derived samples. FIG. 4 shows the results of processing a normal control blood sample from a healthy donor (HD) through the CTC-Chip and subjected to d-CTC assay for 4 different gene transcripts, all of which are negative (i.e., blank droplets).

Figure 5:
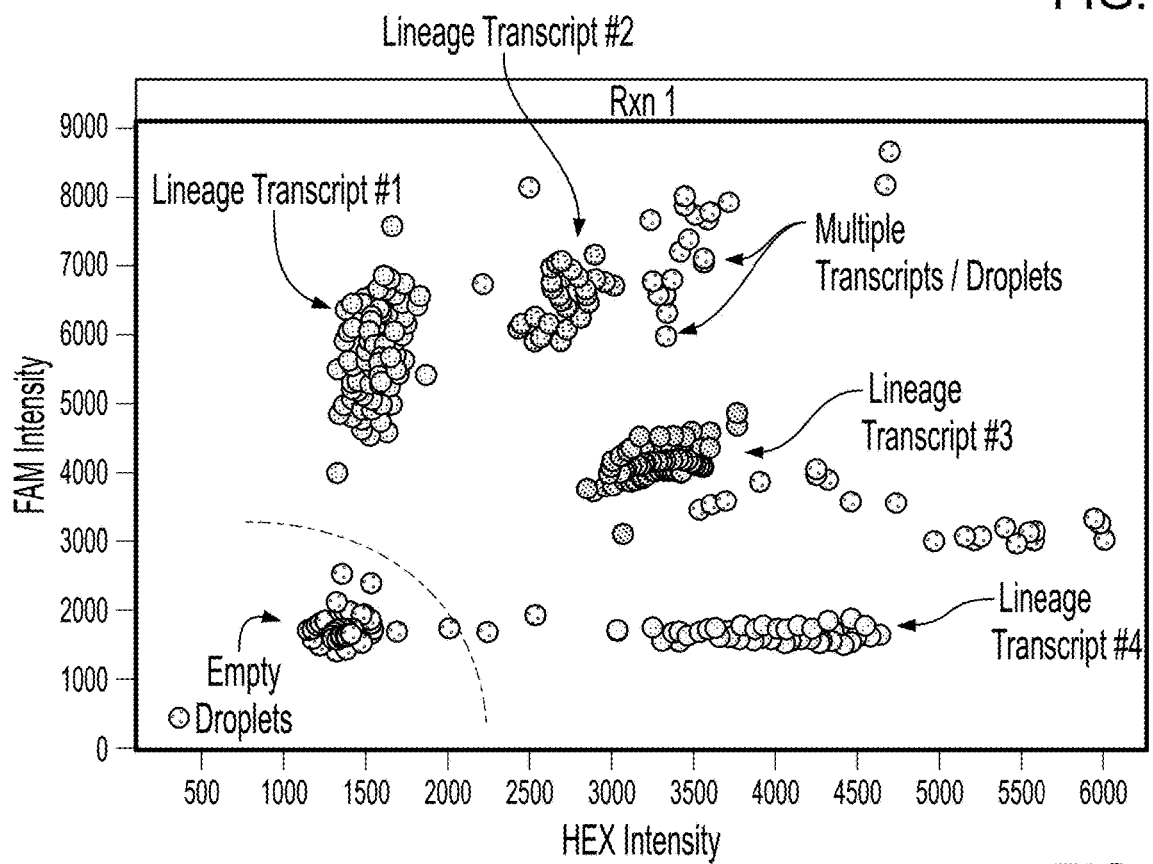
FIG. 5 is a signal intensity plot that shows a d-CTC assay multiplexed for four different lineage specific transcripts to detect prostate cancer cell lines spiked into blood.

On the other hand, FIG. 5 is a representation of data from spiked cell experiments, prostate cancer cell lines introduced into blood and processed through the CTC-Chip, followed by digital assay, showed positive signal (fluorescent droplets) for each of the 4 lineage transcripts. These appeared at separate locations within the 2-Dimensional plot, based on differential fluorescence of two probes (color coded in picture). As the sample is overloaded with tumor cells, some droplets contained signal from more than one gene transcript (multiple genes per droplet are shown in gray).

The strategy of representing four different genes within each reaction was applicable to multiple different cancers, with specific lineage markers substituted for each tumor type. For instance, in prostate cancer, we predicted (theoretical model) a multiplex reaction with four quadrants (one gene per quadrant) for each of 2 reactions (total of 8 gene markers). The spiked cell experiment (prostate cancer cells introduced into control blood and processed through the CTC-iChip) precisely recapitulated the predicted results.

Figure 6A:
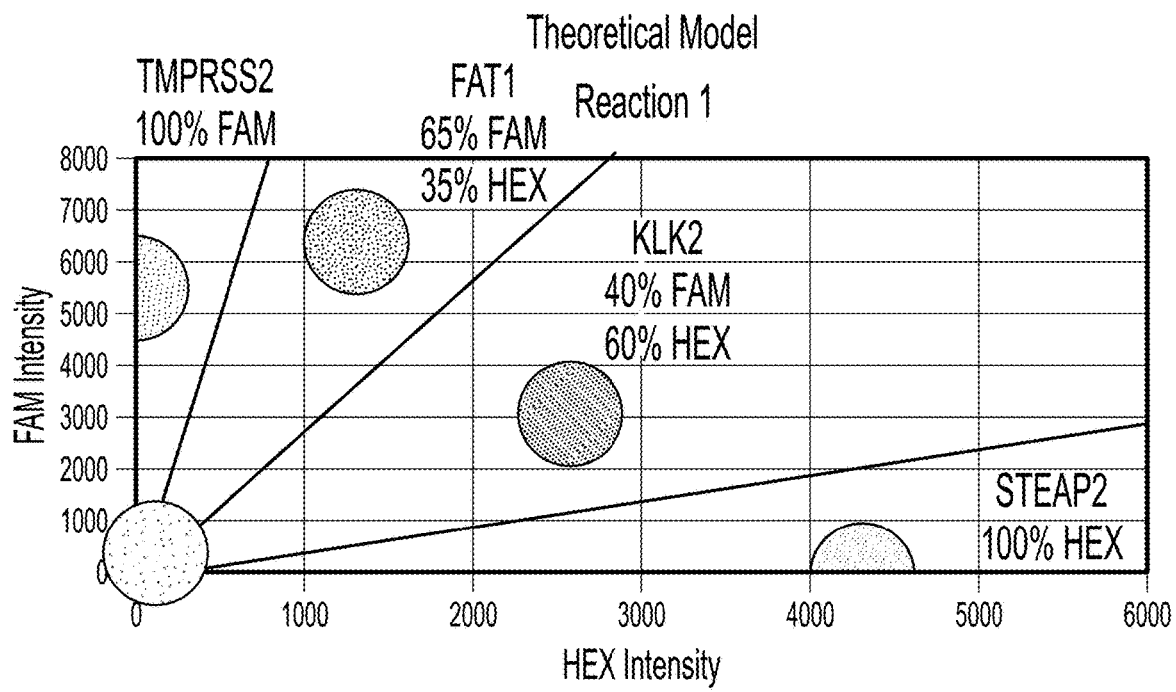
FIGS. 6A to 7B are signal intensity plots showing d-CTC assays multiplexed for four different prostate cancer-specific transcripts per reaction. Both the theoretical model (FIGS. 6A and 7A) and cancer cell line data (FIGS. 6B and 7B) shown for two such reactions, Reactions 1 and 2, demonstrate that the theoretical model accurately predicts the experimental data.
Figure 6B:
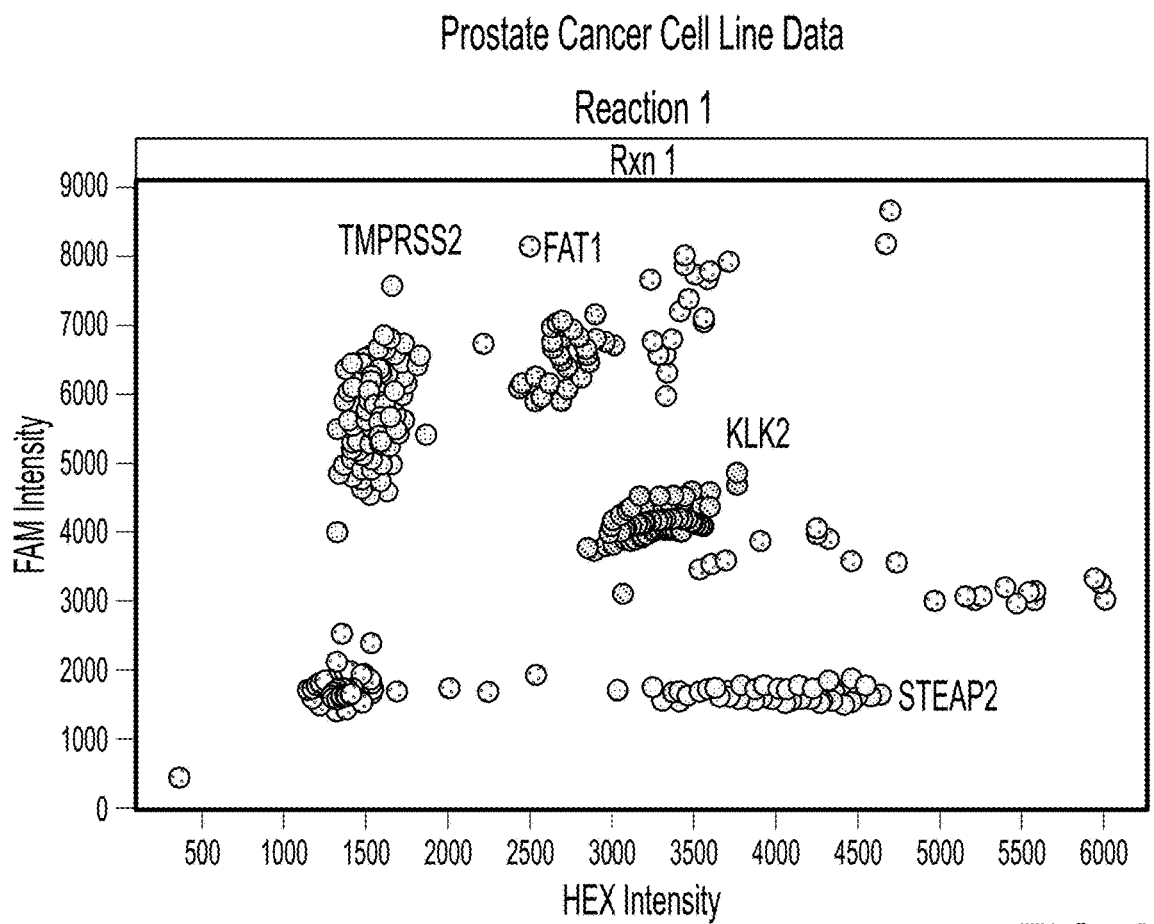
Figure 7A:
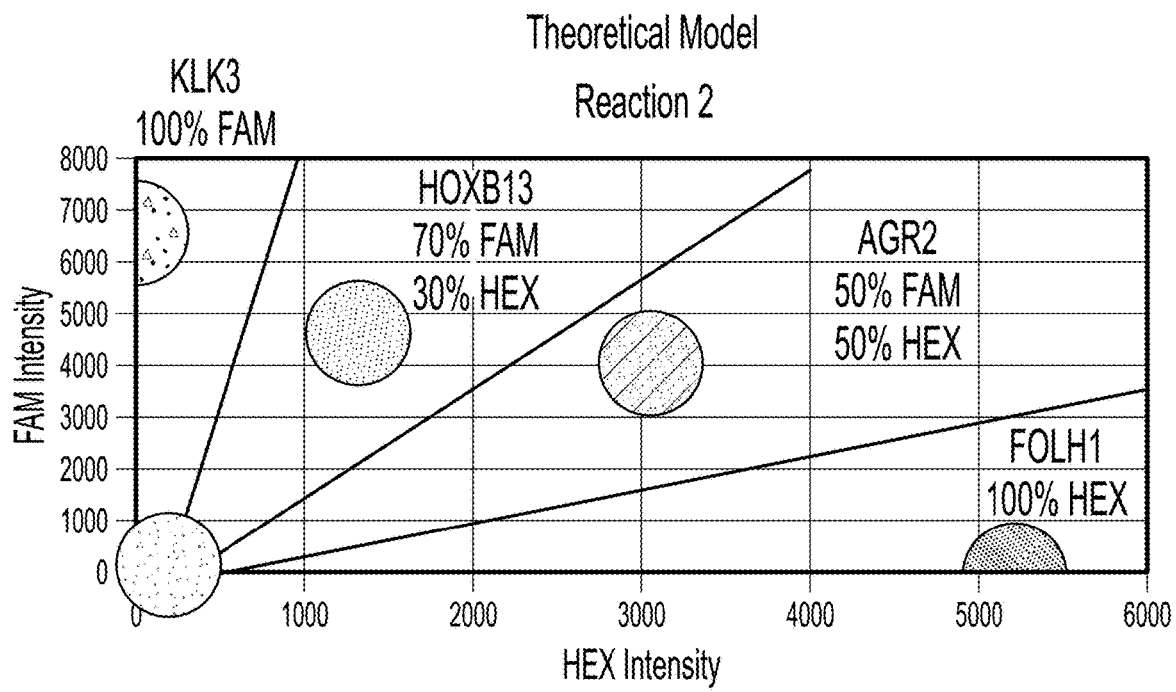
Figure 7B:
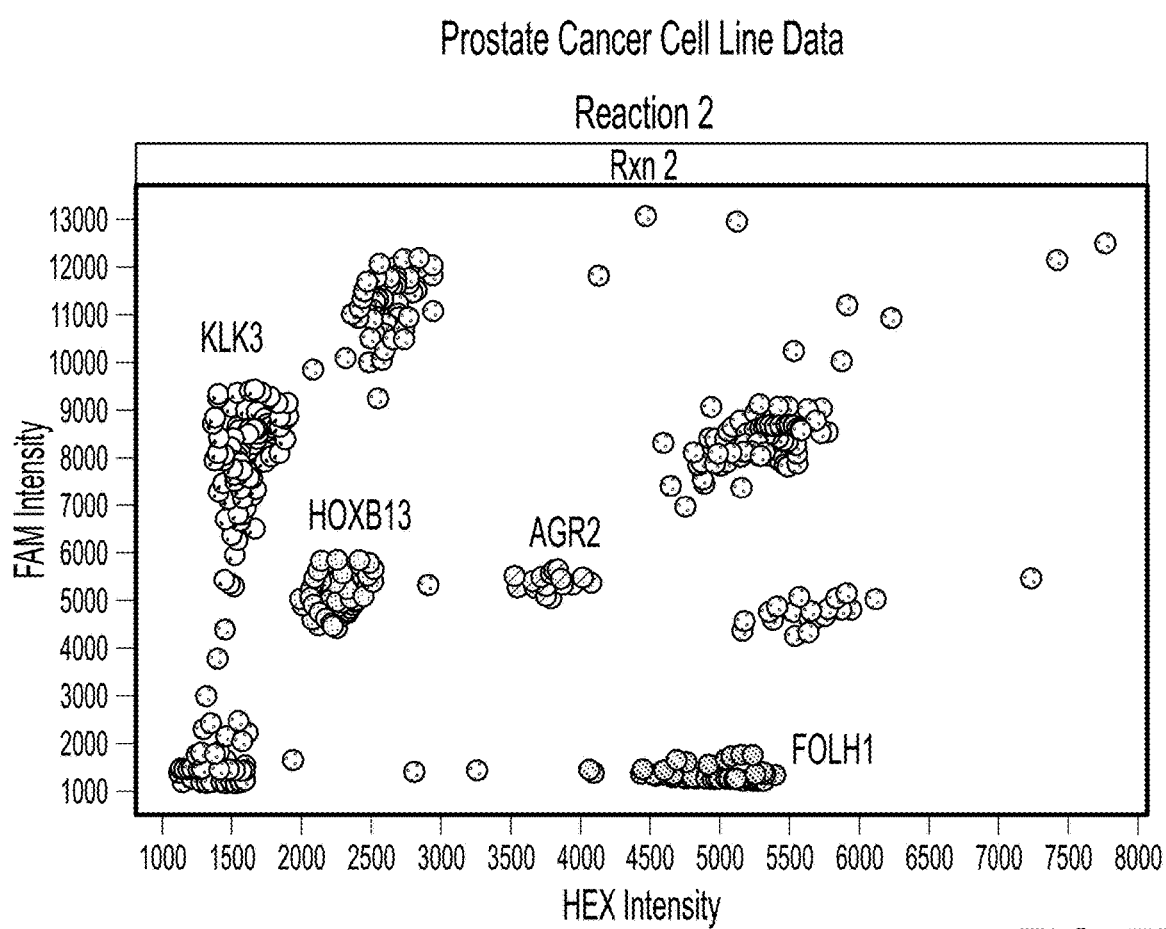

Furthermore, FIGS. 6A-6B and FIGS. 7A-7B show that when assembled together, our analytic program integrated all positive signals within quadrants, just as predicted from modeling, and allowing us to develop methods to score the specific gene signals. Multi-dimensional space analysis of signal allowed for automated analysis and scoring with high level accuracy. FIGS. 6A and 6B show the theoretical model and actual results, respectively, for a prostate cancer cell line for Reaction 1, and FIGS. 7A and 7B show the theoretical model and actual results, respectively, for the same prostate cancer cell line for Reaction 2.

Figure 8A:
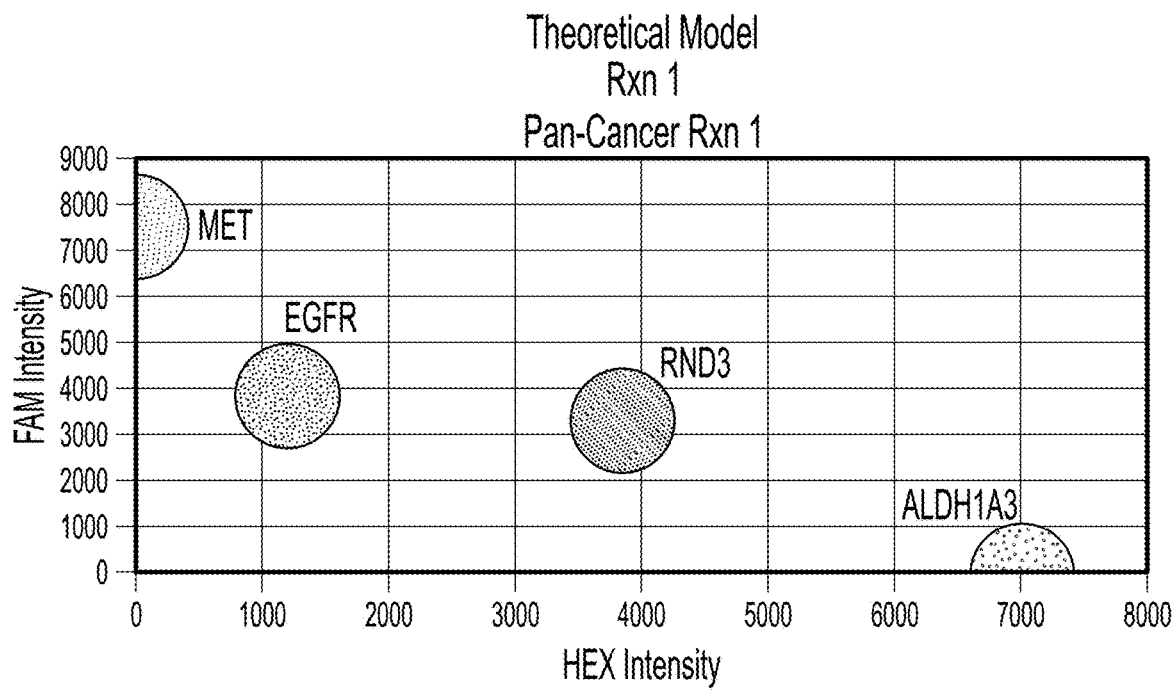
FIGS. 8A to 8B are signal intensity plots showing d-CTC assays multiplexed for four different breast and lung cancer specific transcripts per reaction. Both the theoretical models (FIGS. 8A, 9A, 10A, 11A, 12A, and 13A) and cancer cell line data (FIGS. 8B, 9B, 10B, 11B, 12B, and 13B) shown for six such reactions, Reactions 1 through 6, each with different combinations of markers, demonstrate that the theoretic model accurately predicts the experimental data.
Figure 8B:
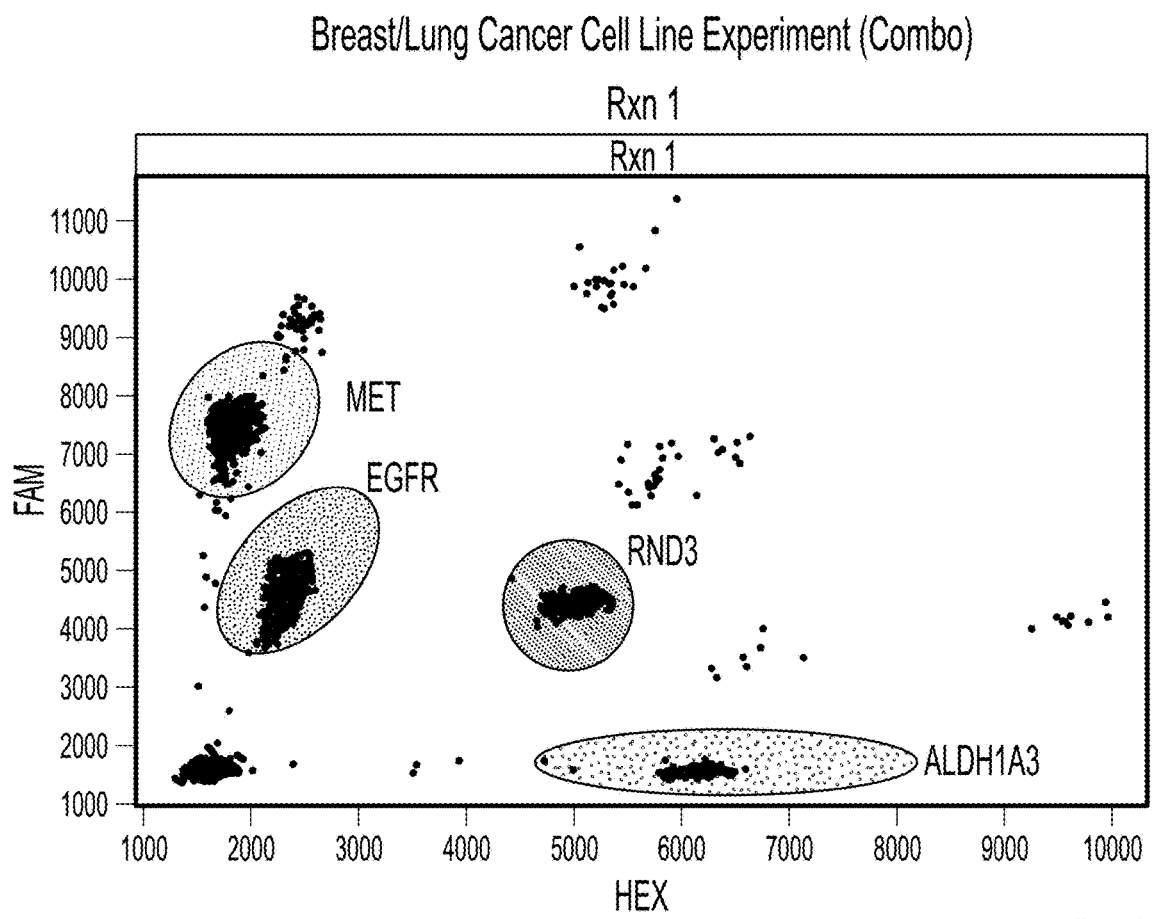
Figure 9A:
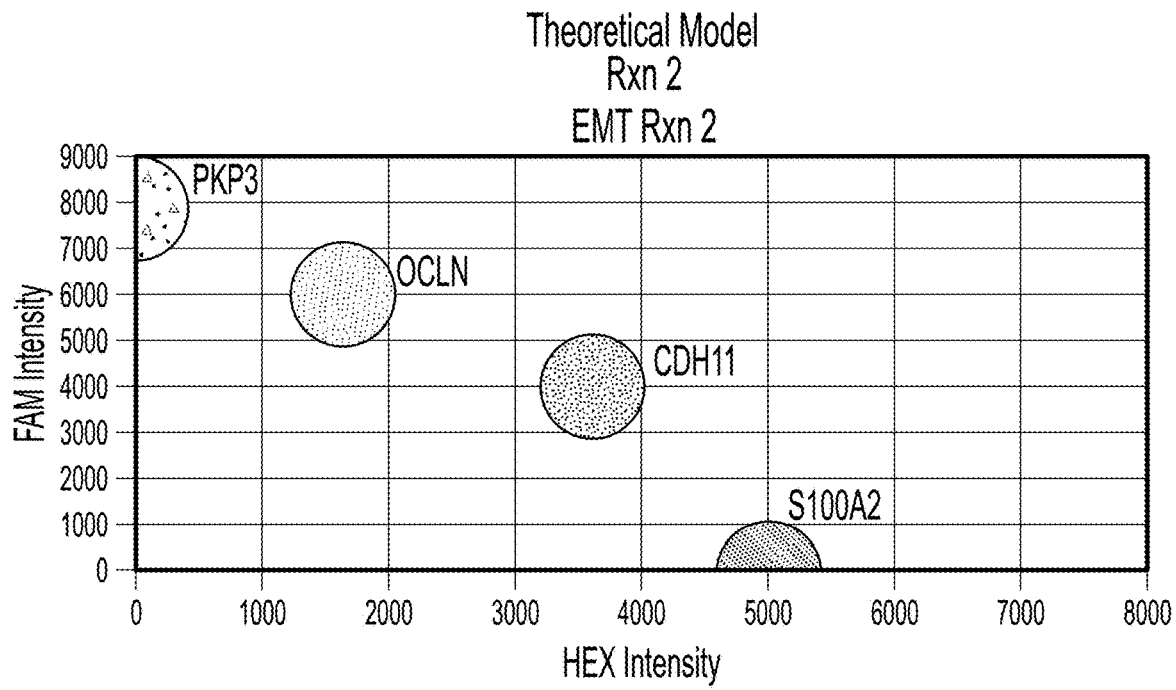
Figure 9B:
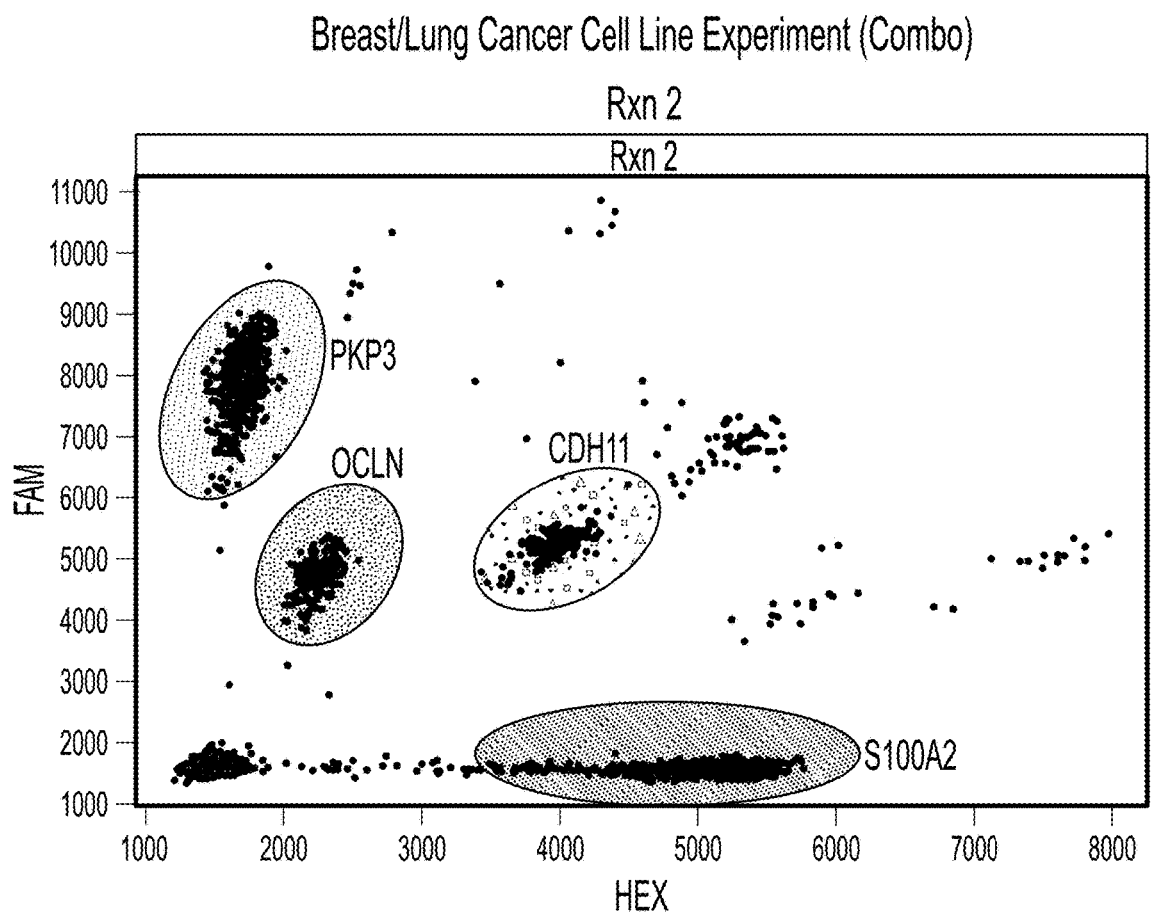
Figure 10A:
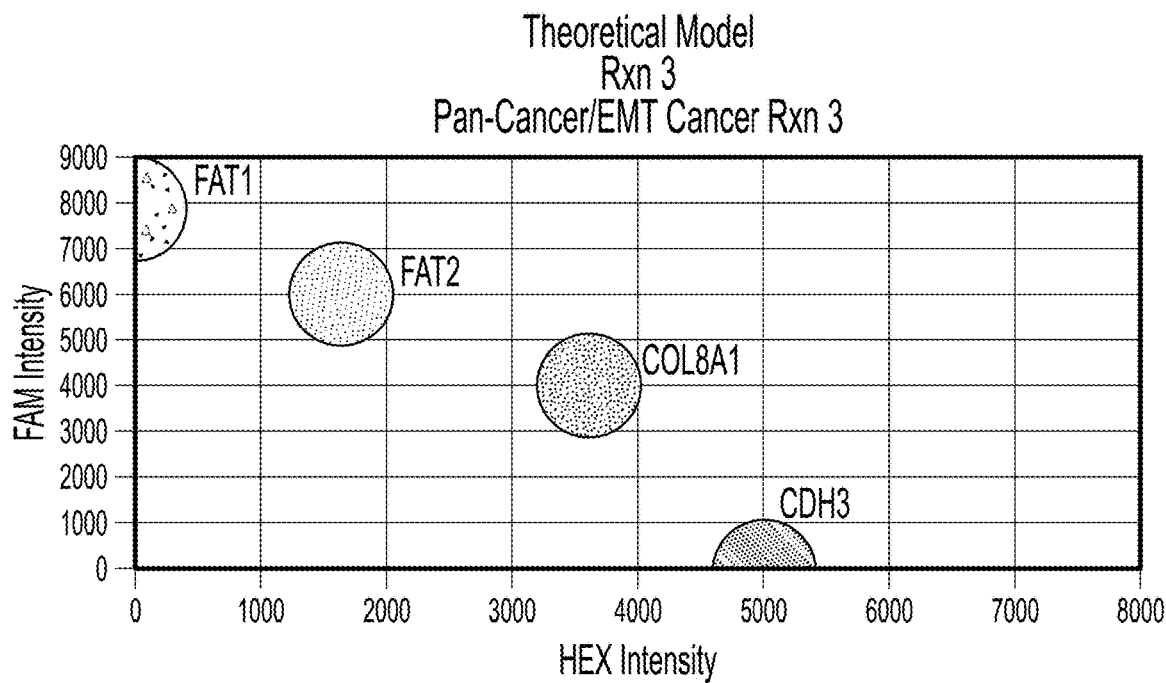
Figure 10B:
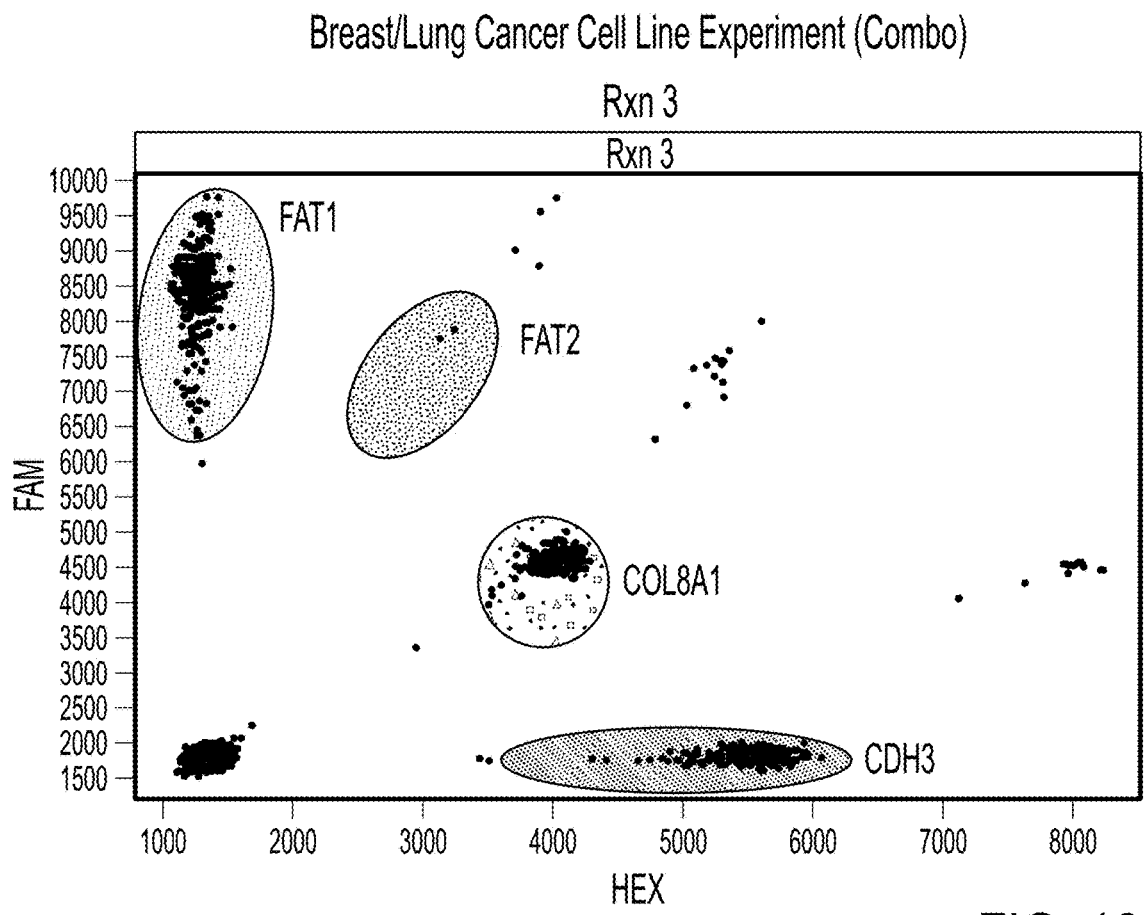
Figure 11A:
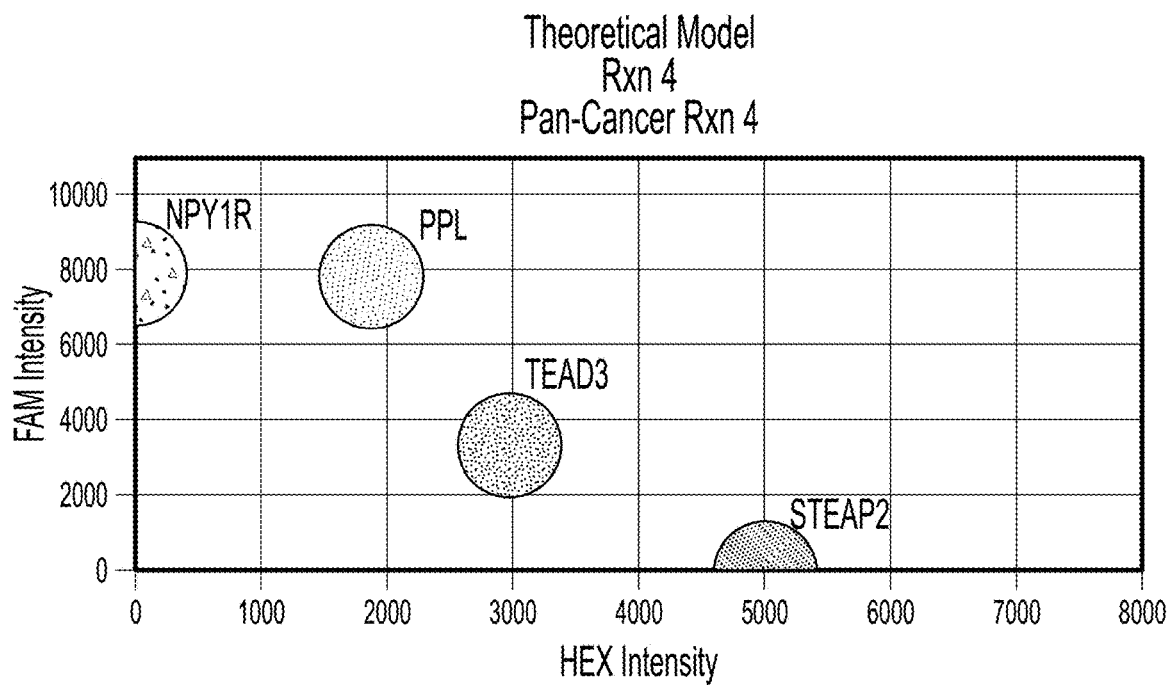
Figure 11B:
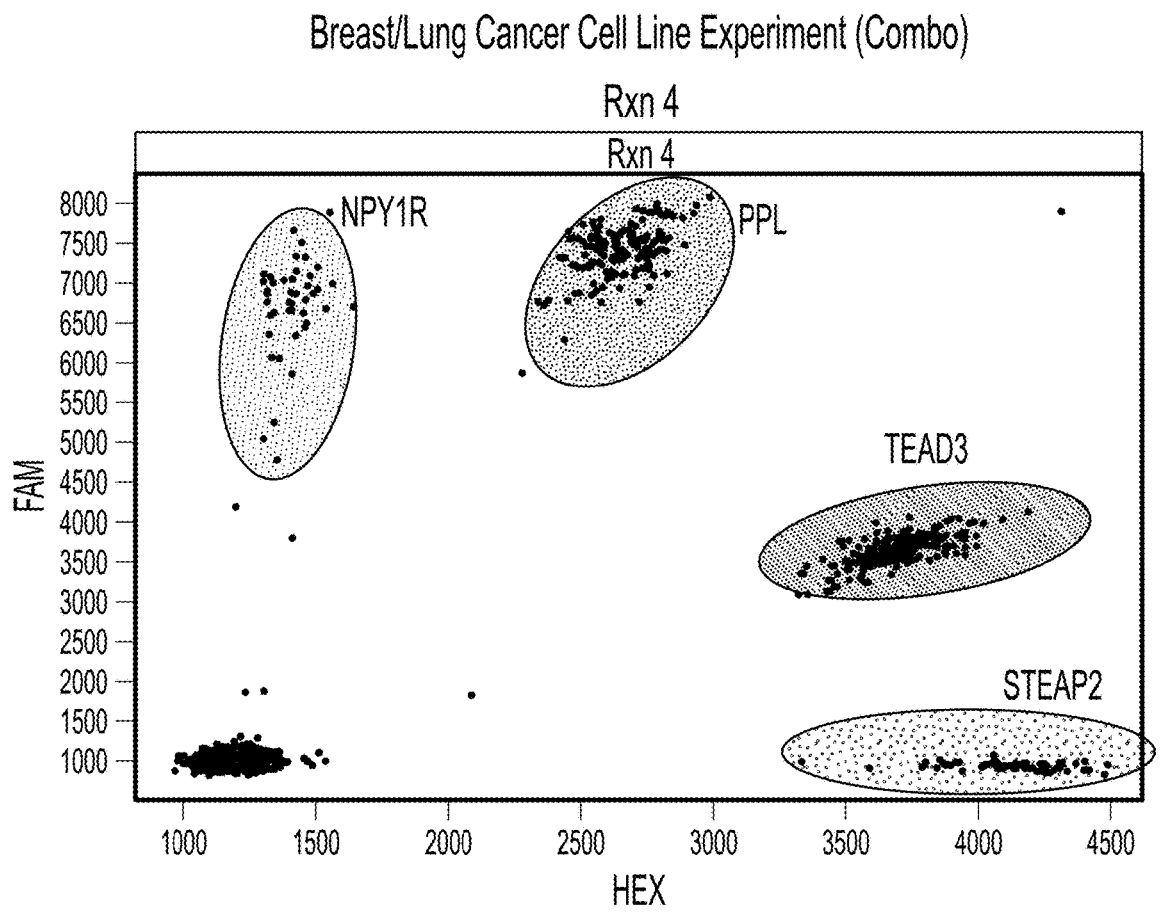
Figure 12A:
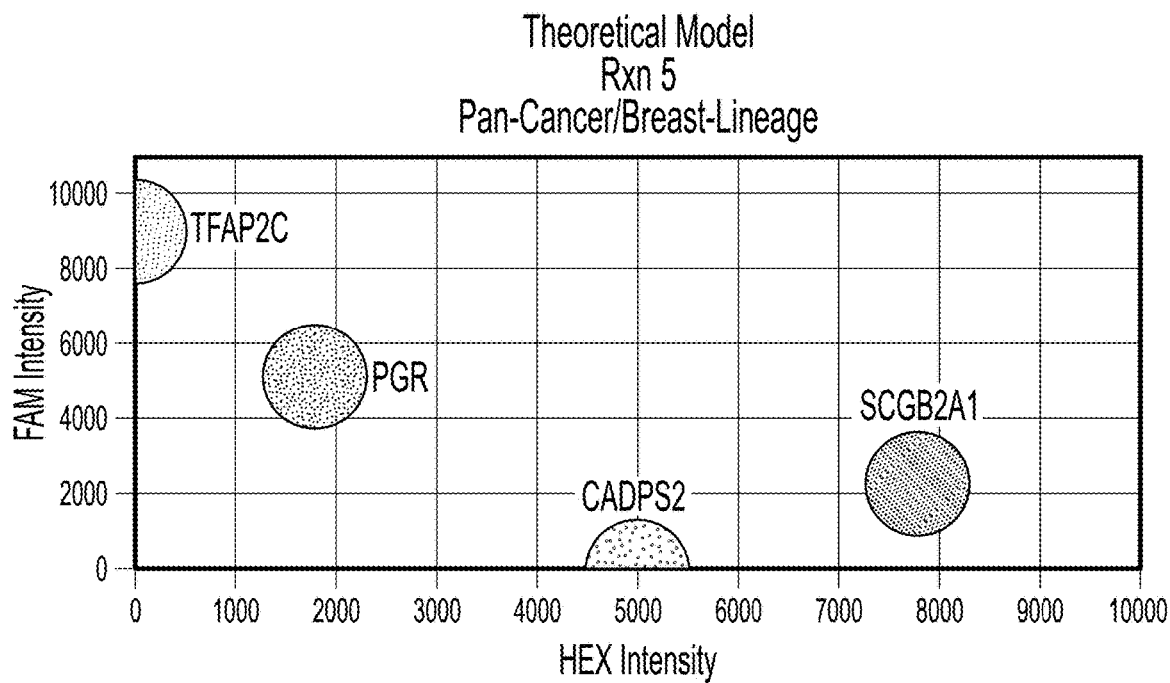
Figure 12B:
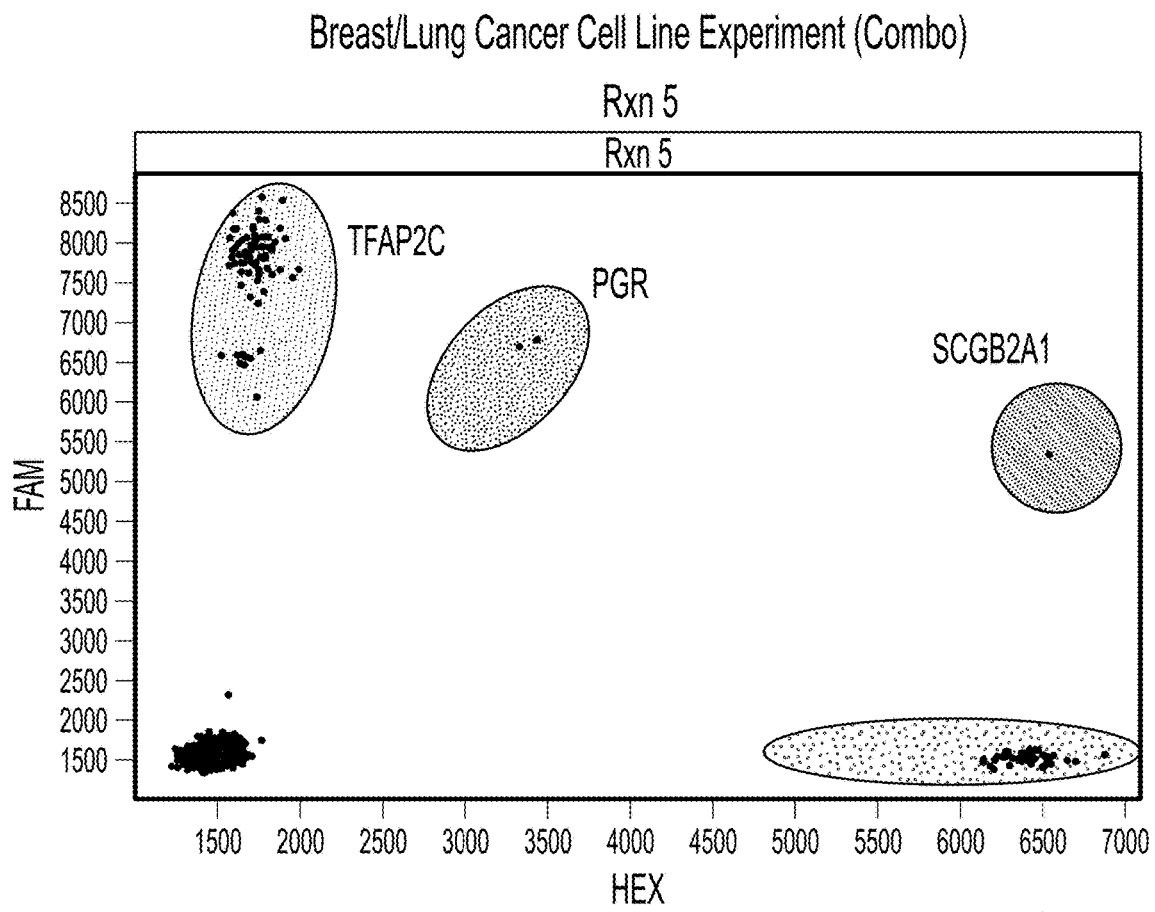
Figure 13A:
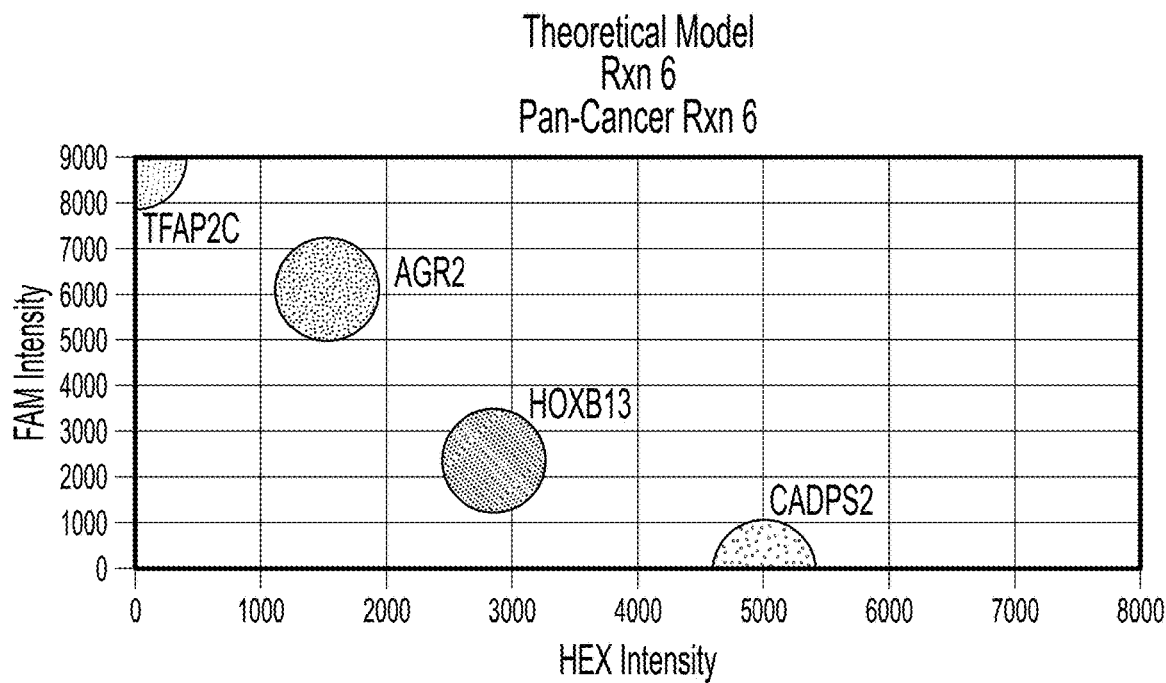
Figure 13B:
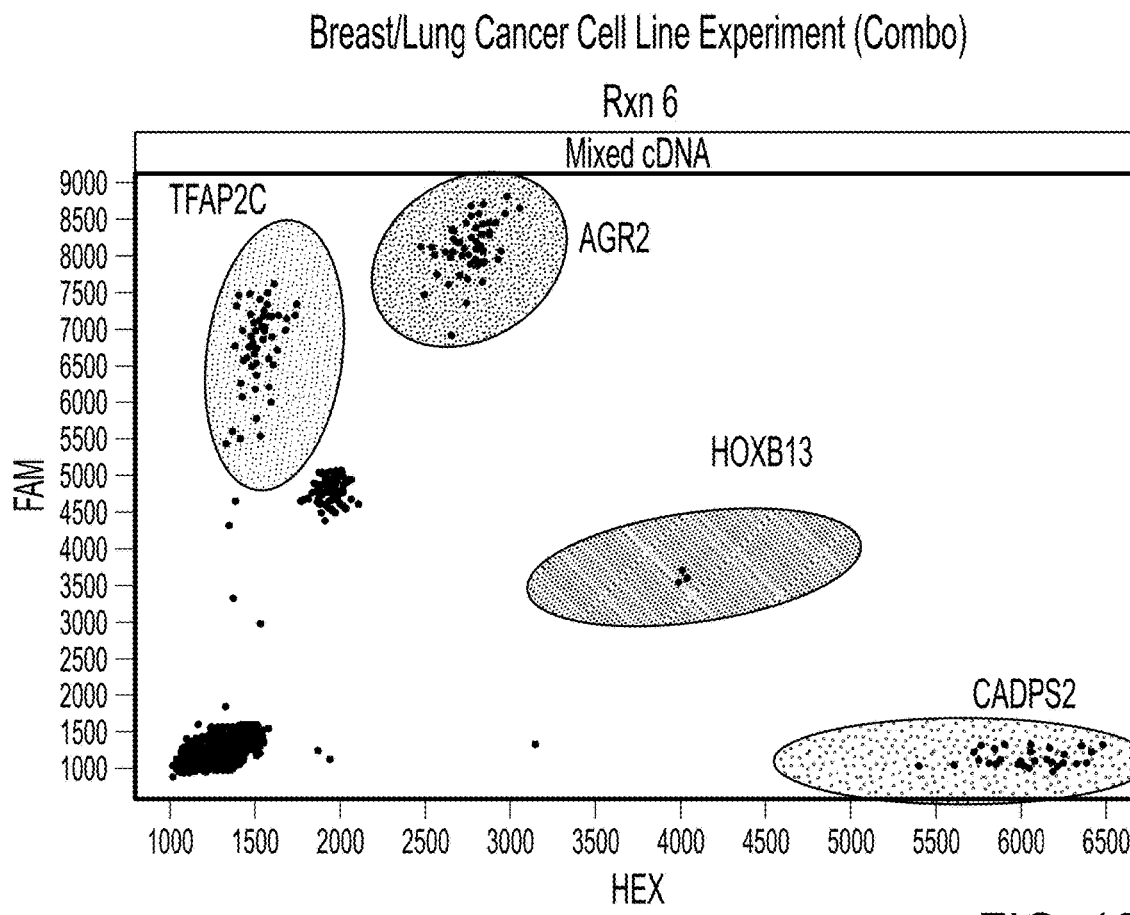

FIGS. 8A-8B (breast and lung cancer theoretical and actual results, Reaction 1), 9A-9B (breast and lung cancer theoretical and actual results, Reaction 2), 10A-10B (same, Reaction 3), 11A-11B (same Reaction 4), 12A-12B (same, Reaction 5), and 13A-13B (same, Reaction 6) illustrate the results when the same approach was use with breast cancer and lung cancer. We can establish a multi-cancer panel that is effective in identifying markers shared by most adenocarcinomas (i.e., grouping breast and lung cancer together), as 6 reactions (4 gene markers within each reaction for a total of 24 markers), as shown below (theoretical vs validation using spiked cell experiments with both breast and lung cancer cells).

These figures show the results when the same approach of testing multiple gene transcripts in multiplex fashion (4 genes per reaction) was applied to breast cancer. Six different reactions were performed of the same CTC chip product (enabling a total of 24 gene transcripts to be tested independently), with each one having a designated signal position (predicted in upper panel) and observed in spiked cell validation experiments (observed in lower panel).

Example 5

Target-Specific Pre-Amplification to Improve Detection of Tumor-Specific mRNA

To improve the detection of tumor specific RNAs, a nested PCR strategy was optimized for each of the gene-specific amplifications. To achieve this, cDNA derived from the CTCs was first amplified with gene-specific primers which are situated a few base pairs external to the gene-specific primers used for d-CTC assay. For each gene, two to three primer sets were tested, and the primer set that is compatible with the gene-specific d-CTC assay primer and tests negative in HD blood was chosen for analysis of patient samples.

As described above, the target specific amplification protocol was first tested in cell lines derived from the different cancers. The primer combinations that are specific for tumor cells (and absent in leukocytes) were then tested with a mixture of cancer cell lines mixed into blood and enriched through the CTC-iChip. HD blood processed through the CTC-iChip was used as control. Key to this strategy is the design of the nested PCR conditions to enhance the signal from minute amounts of CTC-derived cDNAs, without increasing the minimal baseline signal from normal blood cells. This selectivity was achieved by careful optimizing of PCR primer sequences and assay conditions, as well as balancing the cycle number for the external and internal PCRs. All conditions are validated first with purified nucleic acids, then with individual tumor cells that are spiked into control blood samples and processed through the CTC-iChip, then with large panels (>10) of different healthy blood donors, and ultimately with patient-derived blood samples from patients who have either metastatic or localized cancers of the prostate, breast, melanoma, liver, lung or pancreas.

Reagents
 DNA Suspension Buffer (10 mM Tris, pH 8.0, 0.1 mM EDTA) (TEKnova, PN T0221)
 0.5 EDTA, pH 8.0 (Invitrogen, PN Am9260G)
 TaqMan PreAmp Master Mix (Applied Biosystems, PN 4391128)
 Nuclease-free Water (TEKnova, PN W330)

Preparing 10× Specific Target Amplification (STA) Primer Mix
 1.) In a DNA-free hood, 0.5 µL of each of 200 µM primer pairs (0.5 µL Forward primer and 0.5 µL Reverse primer) were mixed.
 2.) Each primer was diluted in 1× DNA Suspension Buffer to a final concentration of 500 nM. (Ex: If pooled primer volume equals 8 mL, add 192 mL DNA Suspension Buffer)
 3.) The mix was vortexed for 20 seconds and spun down for 30 seconds.
 4.) 10× STA Primer Mix can be stored at 4° C. for repeated use for up to six months or stored frozen at −20° C. for long-term usage.

Preparing STA Reaction Mix
 1.) For each well of a 96-well PCR plate, prepare the following mix.

| Component | Per 9 µL Sample (µL) | 96 Samples with overage (µL) |
|---|---|---|
| TaqMan ® PreAmp Master Mix | 7.5 | 780.0 |
| 10X STA Primer Mix (500 nM) | 1.5 | 156.0 |
| 0.5M EDTA, pH 8.0 | 0.075 | 7.8 |
| Total Volume | 9.0 | 943.8 |

2.) 6 µL cDNA was added to 9 µL STA reaction mix
 3.) Thermocycling conditions listed below were used with 18 cycles of denaturation and annealing/extension steps rather than 20 cycles. (Note: 18 cycles were used to compare TSA Pre-Amplification protocol to Whole Transcriptome Amplification).

| | | 10 to 18 Cycles | | |
|---|---|---|---|---|
| Condition | Enzyme Activation | Denaturation | Annealing/ Extension | Hold |
| Temperature | 95° C. | 96° C. | 60° C. | 4° C. |
| Time | 10 minutes | 5 seconds | 4 minutes | Infinity |

1 µl of the pre-amplified product is loaded in each droplet PCR reaction.

Figure 14:
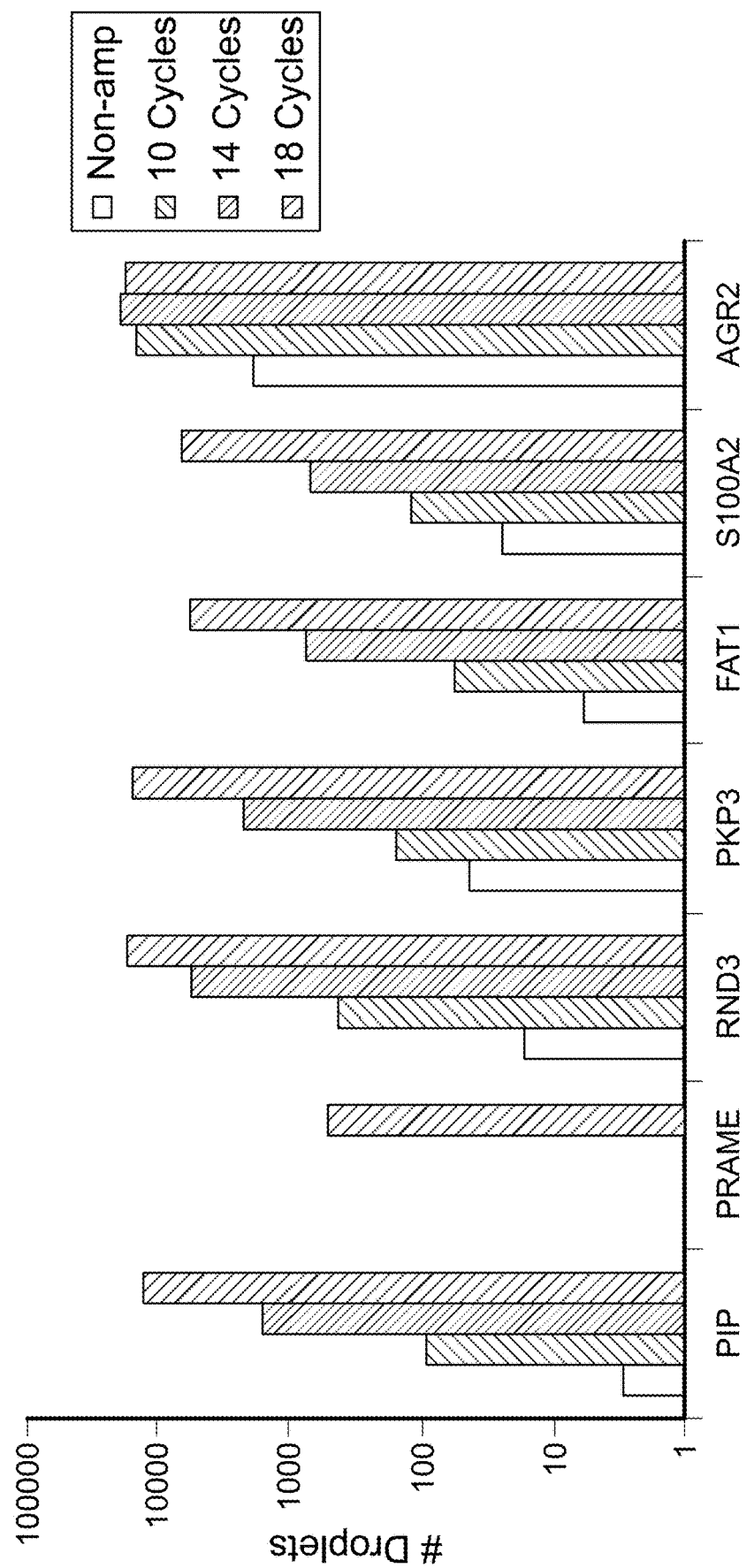
FIG. 14 is a bar graph showing droplet PCR signal for seven different biomarkers (PIP, PRAME, RND3, PKP3, FAT1, S100A2, and AGR2) from 1 ng of non-amplified cell-line cDNA and from 1 μl of pre-amplified product after 10, 14, and 18 cycles of Specific Target Amplification (STA) pre-amplification, demonstrating the significant enhancement of droplet PCR signal from STA pre-amplification.

FIG. 14 shows the droplet PCR signal for 7 markers (PIP, PRAME, RND3, PKP3, FAT1, S100A2, and AGR2) from 1 ng of non-amplified cell-line cDNA and from 1 µl of pre-amplified product after 10, 14, and 18 cycles of pre-amplification. Additional cycles of pre-amplification result in signal increase. Of note, PRAME, a marker expressed at very low levels in this cell line is detected only after 18 cycles of pre-amplification, demonstrating the utility of the technique.

Example 6

Clinical Data and Assay Validation

The assays described herein have been validated using actual patients samples from clinical studies. These include patients with metastatic cancer (lung, breast, prostate and melanoma), as well as patients with localized cancer (prostate). The assays are conducted as described in Examples 2 through 5.

Figures 15A, 15B, 15C:
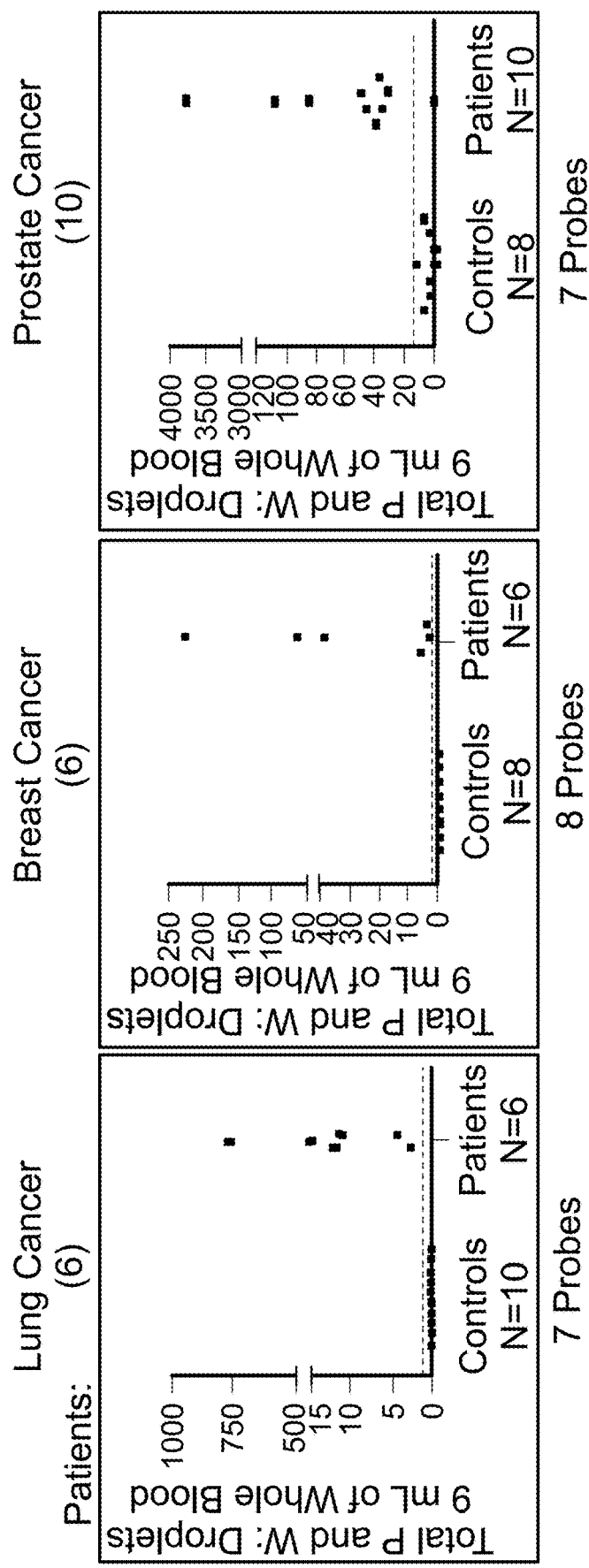
FIGS. 15A to 15C are graphs that show the results of CTC detection in patients using the new d-CTC assay methods for three different sets of patients with lung cancer (FIG. 15A), breast cancer (FIG. 15B), and prostate cancer (FIG. 15C). In each, the healthy patients had no CTCs.

FIGS. 15A, B, and C show a summary of clinical assays from patients with metastatic cancers of the lung (6 patients; FIG. 15A), breast (6 patients; FIG. 15B) and prostate (10 patients; FIG. 15C) showed that virtually all patients have positive signal, whereas healthy controls have none. In this assay, all positive scores were added (cumulative score). However, as described below, the scores can also be broken down by individual genes, as shown in FIG. 16.

Figure 16:
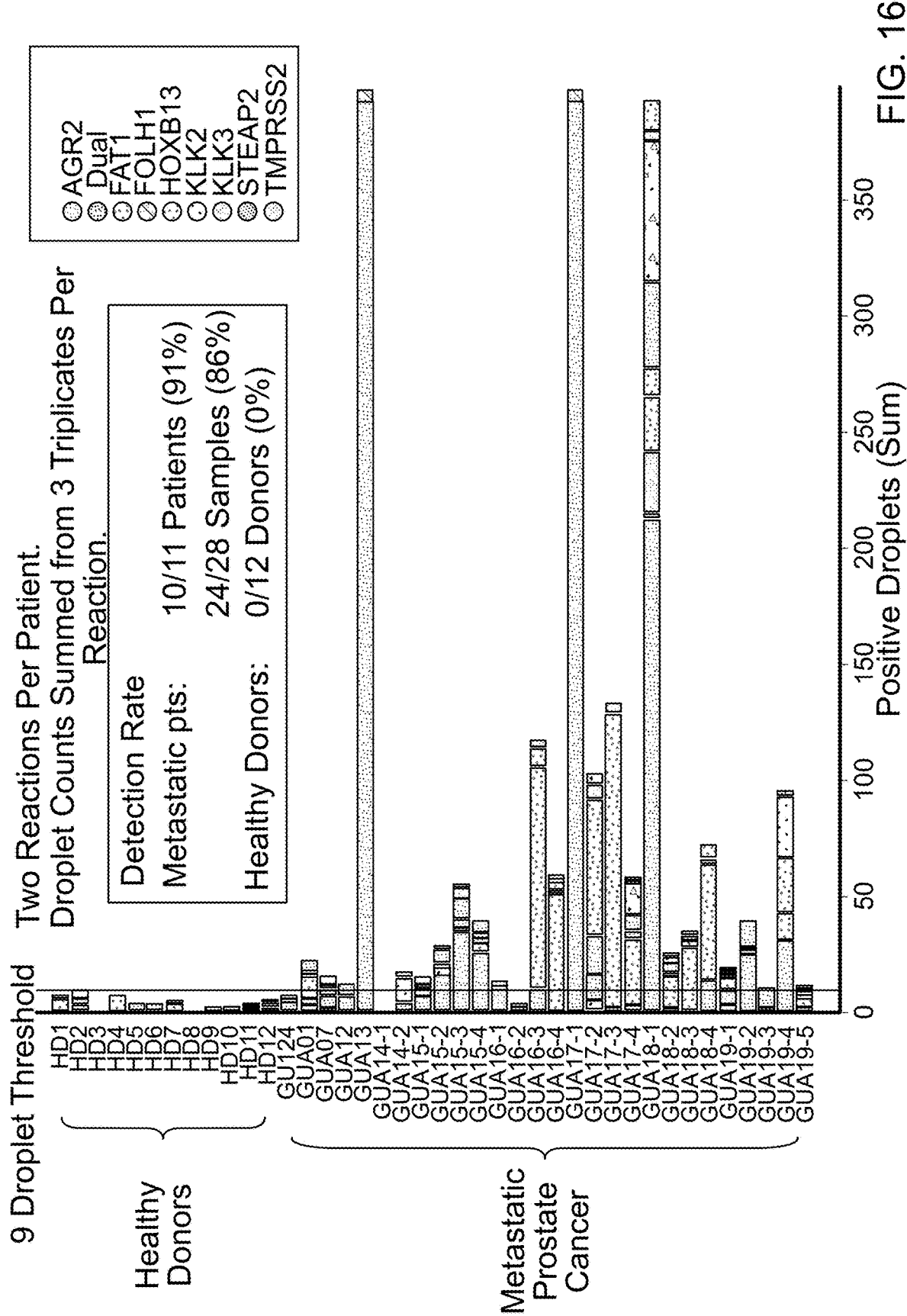
FIG. 16 is a horizontal bar graph that shows the results of patient prostate cancer data using a multiplexed d-CTC assay method described herein testing for the nine biomarkers recited in the figure (AGR2, Dual, FAT1, FOLH1, HOXB13, KLK2, KLK3, STEAP2, and TMPRSS2). 91 percent of cancer patients had detectable CTCs (10 of 11 patients), 24 of 28 samples contained detectable CTCs (86%), and 0 of 12 (0 percent) of healthy donor (HD) blood samples contained CTCs.

FIG. 16 illustrates the cumulative analysis of data from multiple probes, and shows a positive signal in $^{10}/_{11}$ metastatic prostate cancer patients (91% on a per patient basis) versus $^{0}/_{12}$ (0%) of healthy controls. On a per sample basis, 24 of 28 samples had a positive signal, indicating an 86% detection rate. In addition, some individual markers were also fairly effective, e.g., AGR2 ($^{9}/_{10}$ detection for metastatic cancer, and $^{0}/_{3}$ for localize cancer), TMPRSS2 ($^{5}/_{10}$ and $^{1}/_{3}$), KLK2 ($^{6}/_{10}$ and $^{0}/_{3}$), STEAP2 ($^{1}/_{10}$ and $^{1}/_{3}$), FAT1 ($^{2}/_{10}$ and $^{1}/_{3}$), and FOLH1 ($^{3}/_{10}$ and $^{1}/_{3}$)

As illustrated above, one can also break down the individual gene markers for independent validation and quantitation, using the multiplex fluorescence color scheme described above. In this example below, a patient with metastatic prostate cancer had multiple positive markers, a patient with localized prostate cancer has a smaller number of positive scores within fewer markers, and a healthy control is negative for all markers.

Figure 17:
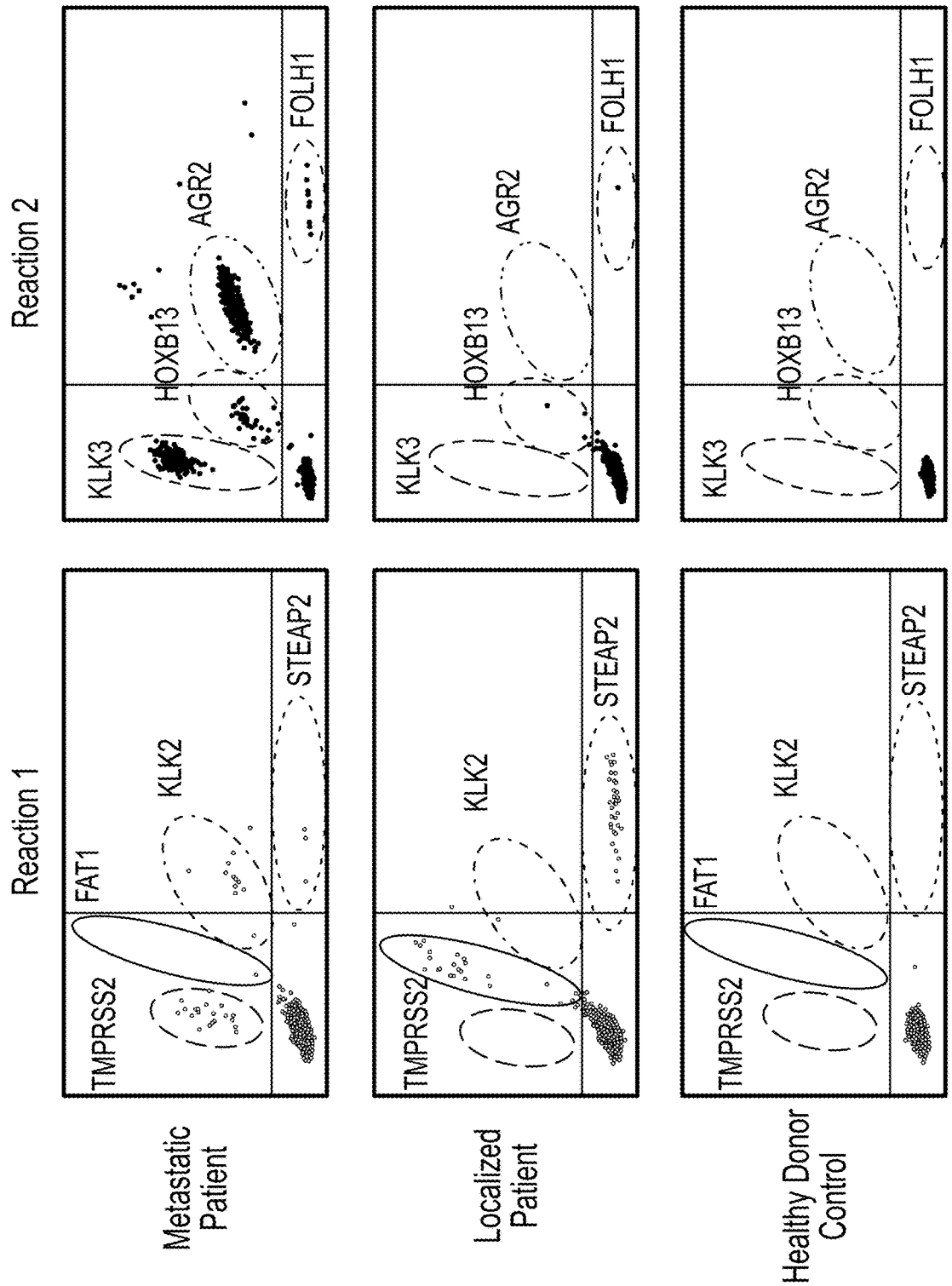
FIG. 17 is a series of signal intensity plots showing d-CTC assays multiplexed for for two different reactions (Reaction 1 (TMPRSS2, FAT1, KLK2, and STEAP2), left column, and Reaction 2 (KLK3, HOXB13, AGR2, and FOLH1), right column) for blood samples from a metastatic prostate cancer patient (top row), a localized prostate cancer patient (middle row), and from a healthy donor control sample (bottom row). In each case there were no CTCs in the healthy donor (HD) samples, but clear evidence of CTCs in the cancer samples.

FIG. 17 shows clinical data from three representative patient samples. In two separate reactions with four gene transcripts each (8 probes total), a blood sample from a patient with metastatic prostate cancer showed multiple signals (all probes are positive to various degrees). In contrast, a blood sample from a patient with localized (curable) prostate cancer showed weaker (but clearly detectable) signal. Whereas probes 1 (TMPRSS2), 5 (KLK3), 6 (HOXB13), 7 (AGR2) had the strongest signal in the metastatic cancer patient, probes 2 (FAT1) and 4 (STEAP2) were most positive in the localized cancer patient. This result clearly illustrates the heterogeneity in signal among cancer cells in the blood and the importance of dissecting the differential signals within the assay. Blood from a HD control (processed identically to the cancer patient samples) had a complete absence of signal.

Example 7

Measurement of Signaling Pathways within CTCs

In addition to providing a digital (quantitative) measure of CTCs present within a blood sample, our d-CTC assay also allowed analysis of specific signaling pathways that are unique to the tumor cells in the blood. For instance, a subset of prostate lineage-specific genes were driven by androgen signaling (such as PSA), while another subset was repressed by androgen signaling (such as PSMA). By analyzing these genes together, we can ascertain the status of androgen signaling within CTCs. Defining the total number of CTC signal in the blood, simultaneously with information about the effectiveness of the therapeutic agent in targeting and shutting off the critical pathway is important for therapeutic monitoring.

We have illustrated this concept in prostate cancer, where the anti-androgenic agent abiratorone is effective in suppressing cancer progression, particularly in tumors that are still dependent on the androgen pathway. Below, we showed the results of a patient with "Castrate Resistant Prostate Cancer (CRPC)" who is no longer responding to first line leuprolide and was treated with abiratorone. The androgen response markers (green) were initially suppressed by the therapy as it shows initial efficacy, but subsequently returned as the tumor becomes resistant and the patient experiences disease progression on this drug.

Figure 18:
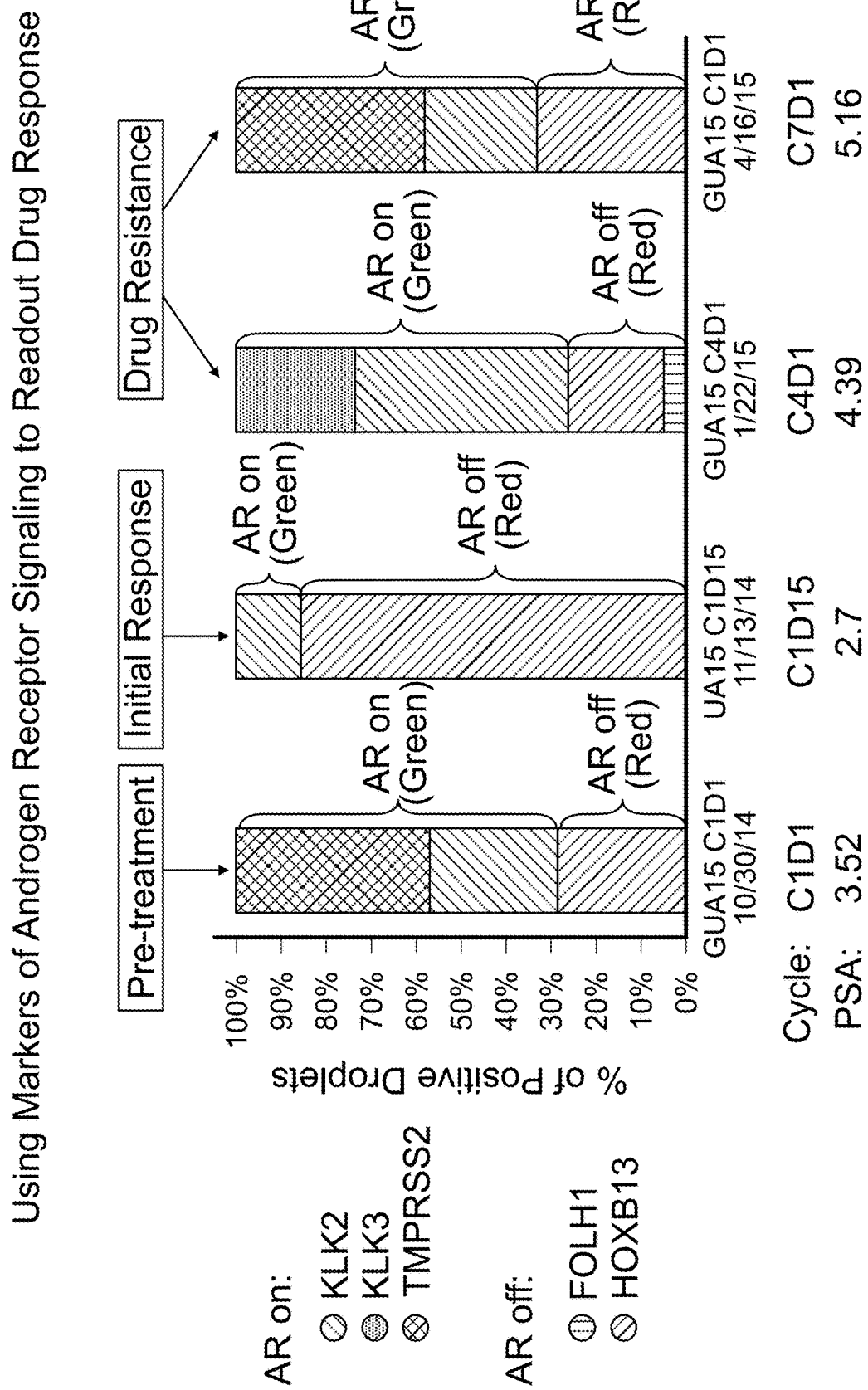
FIG. 18 is a multiple bar graph illustrating the relative proportion of androgen receptor signaling genes in CTCs measured over time to provide a readout of drug response in a prostate cancer patient treated with Abiraterone®.

FIG. 18 provides the results of a clinical study of a patient with metastatic prostate cancer. The subset of signals from "androgen receptor-induced genes (AR-On)" is shown in green at the top of the bars in this bar graph, while the subset of signals from "androgen-repressed genes (AR-Off) is shown in red at the bottom of each bar. As the patient is treated with the androgen pathway inhibitor abiratorone (e.g., ZYTIGA® (abiraterone acetate), the AR-On signal is greatly reduced, indicating effective suppression of the androgen pathway within cancer cells in the blood. By cycle 4 of drug treatment, however, the androgen pathway appears to be reactivated in c1ancer cells (increasing green signal), indicative of drug resistance. Serum PSA measurements taken at these time points are consistent with failure of drug treatment.

Example 8

Non-Specific Pre-Amplification to Improve Detection of Tumor-Specific mRNA

Similar to Example 5, non-specific whole transcriptome amplification (WTA) can be used to increase the detection rate of CTC-specific transcripts. This method relies on the use of random primers that amplify not only the targets of interest but all messages found in the product. In this example, the SMARTer™ Ultra Low RNA kit protocol (Clontech) was used as described below:

Transfer RNA to PCR Tubes or Plate
1) Add 1 uL of 1:50,000 diluted ERCC Spike-In Mix 1 to each sample
2) Bring the volume of each sample up to 10 uL
3) Add 1 uL of 3' SMART CDS Primer IIA to each sample
4) Run "72C." thermocycler program:
72° C. 3 min
4° C. forever First Strand cDNA Master Mix (FSM):
1×4 uL 5× First-Strand Buffer
0.5 uL DTT
1 uL dNTP Mix
1 uL SMARTer IIA Oligonucleotide
0.5 uL RNase Inhibitor
2 uL SMARTScribe RT
9 uL per sample
5) Prepare the 10% excess FSM for your sample number, then add 9 uL of FSM to each sample and pipet to mix 6) Run "cDNA" thermocycler program:
42° C. 90 min
70° C. 10 min
4° C. forever Second Strand Synthesis and Amplification (SSM):
1×25 uL 2× SeqAmp PCR Buffer
1 uL Primer IIA—v3
1 uL SeqAmp DNA Polymerase
3 uL Nuclease-free water 30 uL per sample
7) Prepare the 10% excess SSM for your sample number, then add 30 uL of SSM to each sample and pipet to mix
8) Run "PCR" thermocycler program:
95° C. 1 min
X cycles
98° C. 10 sec
65° C. 30 sec
68° C. 3 min
72° C. 10 min
4° C. forever The number of cycles can be adjusted depending on RNA input (e.g., 18 cycles for single cells or 9 cycles for 10 ng of RNA input). In addition, the 4 degree stopping point is overnight.

Solid Phase Reversible Immobilization (SPRI) Purification:
Transfer PCR product to lo-bind 1.5 mL Eppendorfs and label a second set of tubes with sample IDs; run the SPRI protocol at RT until the final elution
9) Incubate AMPure™ XP beads [4 deg] at RT for at least 30 minutes
10) Ensure that a sufficient amount of Elution Buffer is thawed and at RT
11) Make 80% ethanol (at least 400 uL per sample)
12) Vortex beads well before adding 50 uL of beads to each sample, pipetting up and down 5-10 times to mix well. Note: When pipetting beads, it's advisable to use RPT tips for better control of the volumes added and less residual bead binding in the tips
13) Incubate samples at RT for 5 minutes
14) Place samples on the magnet and let sit for 5 minutes
15) Pipet out the supernatant (~95 uL) without disturbing the beads (check for brown color in the pipet tip and put back in tube if there's a significant amount of bead loss)
16) Wash twice with 200 uL of 80% ethanol—do not mix or disturb the bead pellet. Simply submerge the bead pellet in the ethanol for 30 seconds and then remove the ethanol. Try not to let the bead pellet dry between ethanol washes.
17) Air-dry the samples on the magnetic rack until the bead pellets are no longer shiny but before they crack. Pipet off any residual ethanol that pools at the bottom while drying (Note: The drying time can vary greatly depending on the DNA concentration after amplification). Single-cell level RNA inputs generally take 3-5 minutes to dry, while other IFD product samples have taken up to an hour.
18) Elute pellets in 17 uL of Elution Buffer as they begin to crack. Remove a sample from the magnet and pipet the buffer over the pellet repeatedly until all of the beads are in solution; then pipet mix to fully resuspend the beads (this will work to varying degrees for each sample). Try not to mix too vigorously as this creates many bubbles, which tends to decrease the attainable elution volume.
19) Let the resuspended samples incubate at RT for at least 2 minutes, then quick spin all of the samples.
20) Put the samples back on the magnetic rack for 5 minutes.

21) Pipet off ~15 uL of your eluted amplified cDNA and check for beads in the pipette tip. If beads are present, pipet the solution back over the bead pellet and let sit for ~1 minute before attempting another elution. Otherwise, store in a new lo-bind 1.5-mL Eppendorf, PCR tube, or 96-well PCR plate. Note: If you are repeatedly getting beads in the elution product, the only solution may be to decrease your aspiration volume to 14 uL or lower.

Figures 19A, 19B:
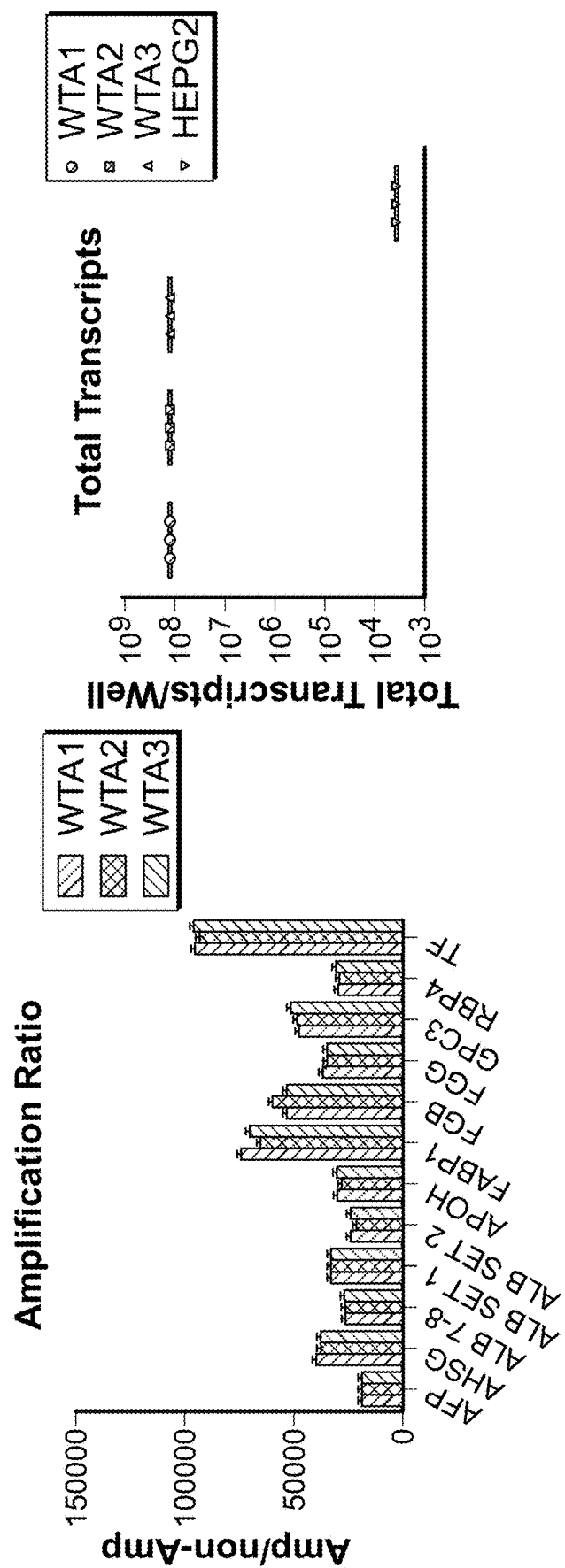
FIGS. 19A and 19B are graphs showing non-amplification versus 18 cycles of SMARTer pre-amplication.

This whole transcriptome amplification (WTA) approach was first tested in cell lines derived from different cancers. FIGS. 19A and 19B show three different replicates of SMARTer-preamplified cDNA (18 cycles) from a liver cancer cell line (HEPG2) analyzed with 12 probes from the liver cancer panel. As shown in FIG. 19A, while the amplification efficiency for each target region is different, it is consistent among the three replicates (WTA1, WTA2, WTA3), demonstrating the reproducibility of this approach. As shown in FIG. 19B, these methods using 18 cycles of SMARTer pre-amplification provide an increase in signal of approximately four orders of magnitude ($10^8$ vs $10^4$), providing a great boost in detection.

Example 9

Multiplexed vs. Individual Marker Assays for Liver Cancer

For each sample, 10-20 mL of blood was collected from each patient. Blood was processed within 3 hours of arrival on a CTC-iCHIP running in negative depletion mode. RNA was extracted from the product using a Qiagen RNeasy™ plus Micro kit, and 5 uL of the available 17 uL amplified using ClonTech's v3 SMARTer™ whole-transcriptome amplification (WTA) strategy. 1% of the WTA product was then loaded into each well of a digital PCR plate, and 500 nM Taqman™ primer/probe combinations used to determine the transcript concentration for each gene of interest. Transcript counts were normalized to blood volume and compared between HCC, HD, and CLD patients. HCC patients are defined as biopsy-confirmed non-resected hepatocellular carcinoma, CLD patients are patients with liver disease of varying etiologies (alcohol-mediated, HBV, HCV) who have negative ultrasound/MRI. HD are healthy donors external to the lab who donate 10-20 mL of blood.

Figure 20A:
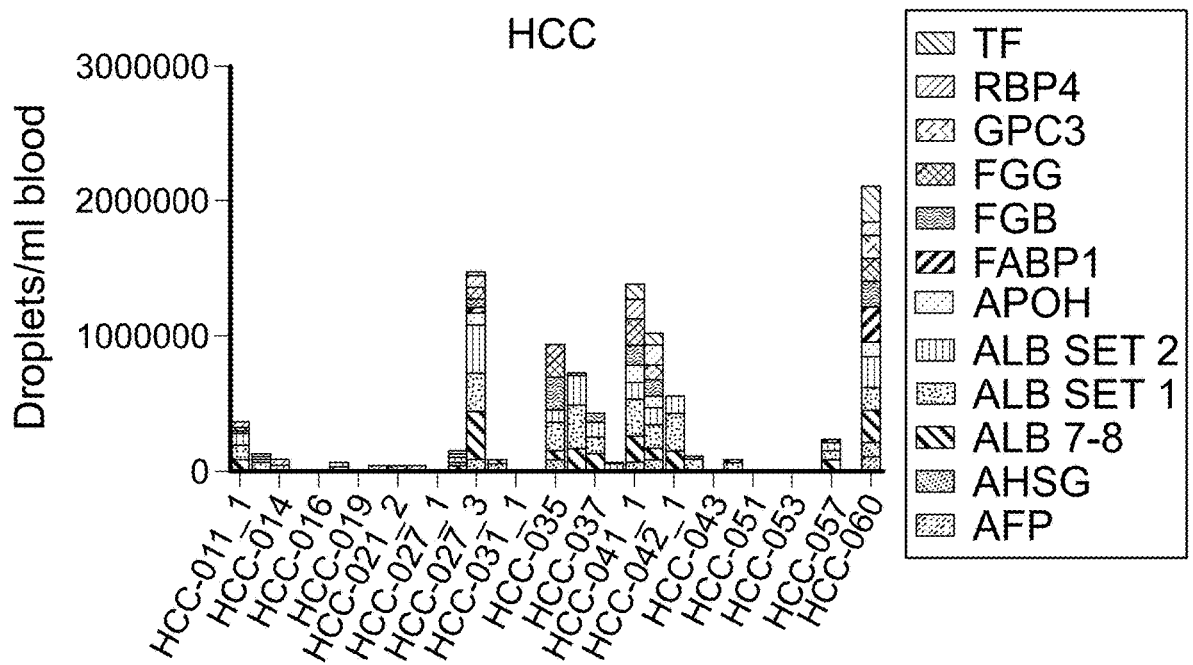
FIGS. 20A to 20C are graphs that show the results of testing of 11 markers in a multiplexed liver cancer assay.
Figure 20B:
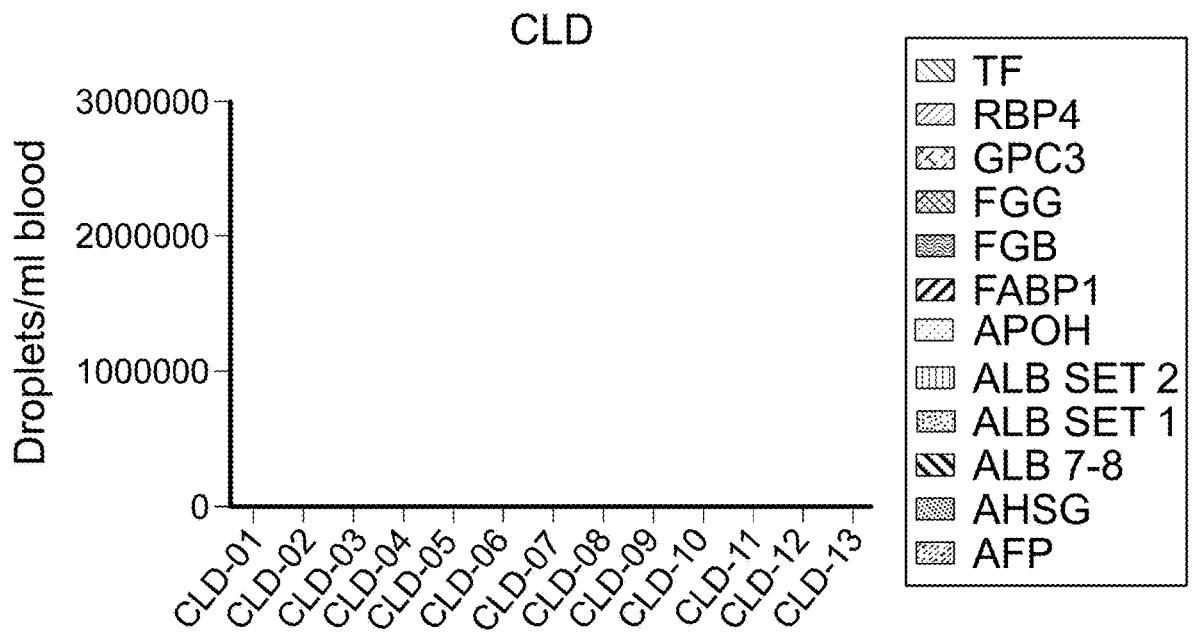
Figure 20C:
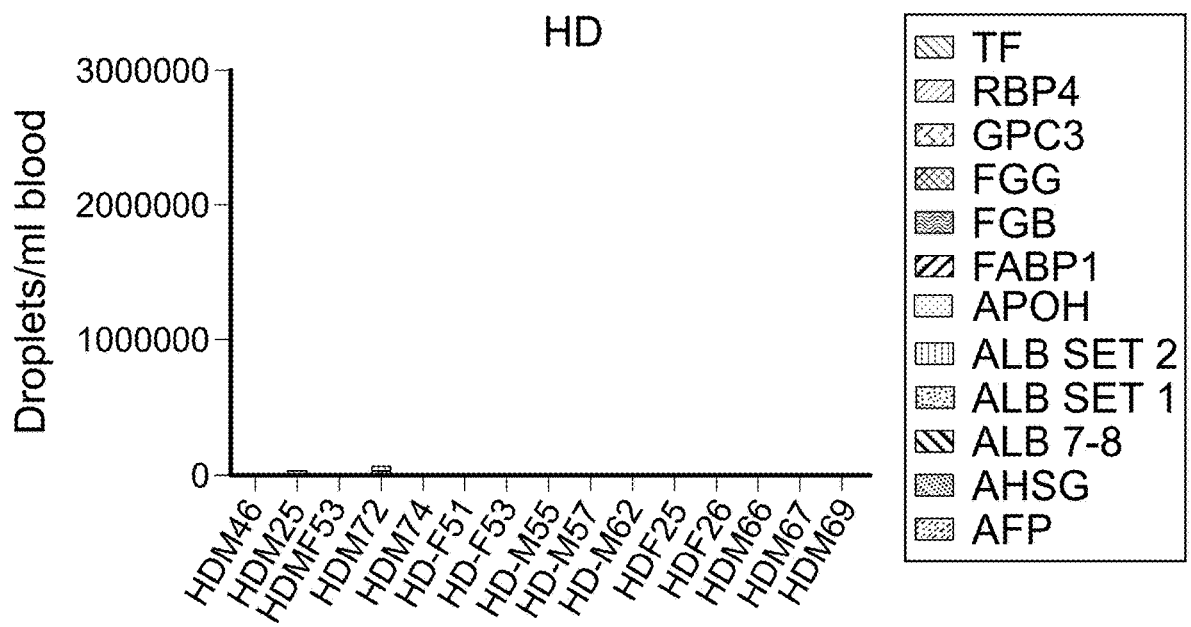

FIGS. 20A to 20C show the total droplet numbers in 21 hepatocellular carcinoma (HCC) patients (FIG. 20A), 13 chronic liver disease (CLD) patients (FIG. 20B) and 15 healthy donors (HDs)(FIG. 20C). HCC patients show higher number of droplets compared to both CLDs and HDs, suggesting that the panel is very clean in the high risk CLD group and can be used to screen those patient for the development of liver cancer. This is an important result given the low specificity of screening methods c=for liver cancer currently available in the clinic. Among CLD patients the American Association of Liver Disease recommends ultrasound (US) every 6 months, with a detailed algorithm dependent on the size of liver lesion detected. A prospective combined AFP gene marker-ultrasound screening in China demonstrated a 37% mortality benefit for those who were screened compared to those who were not, even when the screened population only maintained a compliance rate of 60%.

The sensitivity and specificity of each assay are dependent on the threshold values chosen to define "diseased" vs. "non-diseased," but using 20 ug/L, the AFP gene marker has a sensitivity between 50-80% and a specificity between 80-90%. In a study using 20 ng/ml as the cut-off point, the sensitivity rose to 78.9%, although the specificity declined to 78.1% (Taketa, Alpha-fetoprotein, J. Med. Technol., 1989; 33:1380). On the other hand, the overall detection rate of the present assay was 76% when taking into account the clinical history of the patients and correcting for the ones that received curative resection or liver transplant with 100% specificity.

In addition, while all 11 markers of the liver cancer assay used herein contributed to the 76% sensitivity, the top 5 markers (AHSG, ALB, APOH, FGB and FGG) by themselves have 70% sensitivity, while the top 3 markers alone (ALB, FGB, FGG) result in 67% sensitivity. ALB alone detected 56% of the cases.

Example 10

Multiplexed vs. Individual Marker Assays for Lung Cancer

Blood samples from 8 metastatic lung patients and 8 healthy donors were processed through the CTC-chip as previously described. Samples were spun down, treated with RNAlater™ and stored at −80C. RNA was purified and cDNA was synthesized as described. STA was performed on each sample using 6 μl cDNA and the nested primers corresponding to the probes listed in the figure. 1 μl of STA product was loaded per each droplet PCR reaction.

Figure 21A:
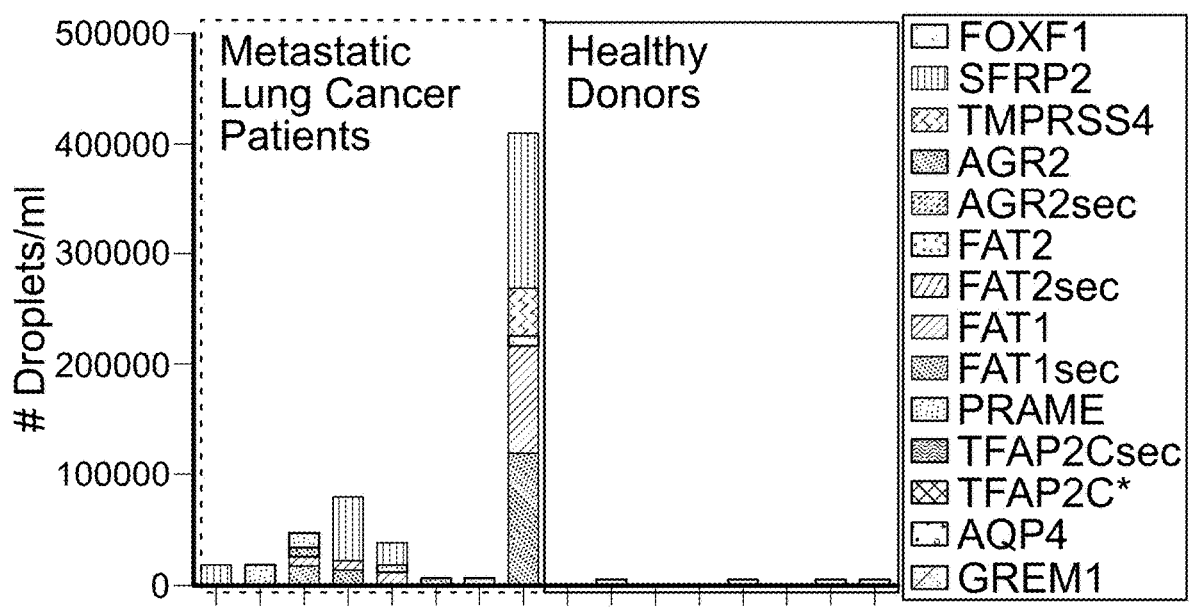
FIGS. 21A and 21B are graphs that show the results of a 14 marker multiplexed lung cancer assay.
Figure 21B:
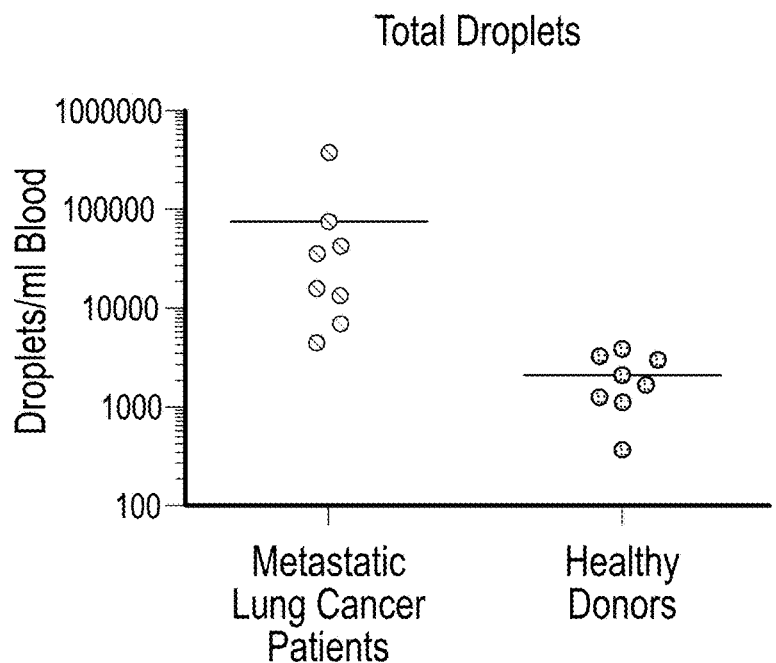

Droplet numbers were normalized to blood volume. As shown in FIGS. 21A and 21B, the multiplexed lung gene marker panel was able to detect 100% (8/8) metastatic lung cancer patient samples above the background of the 8 healthy donors. The sensitivity of each marker of the lung panel was also determined and the results show that SFRP had a detection rate of 8/8, FAT1 Probe 2 had a detection rate of 7/8, TMPRSS4 had a detection rate of 6/8, FOXF1 and ARG2, Probe 2 had a detection rate of 5/8, FAT1 had a detection rate of 4/8, FAT2 and AGR2 had a detection rate of 3/8, and FAT2, Probe 2 had a detection rate of 2/8.

Assays for SERPINA3 and SFRP2 indicated that SFRP2 is effective for both lung and breast cancer detection, whereas the former seems more specific for breast cancer detection, but also detects some lung cancer samples.

Example 11

Multiplexed vs. Individual Marker Assays for Breast Cancer

Blood samples from 9 metastatic breast cancer patient, 5 localized breast cancer patients, and 15 healthy donors were processed though the CTC-Chip. Products were pelleted, treated with RNAlater™ and stored at −80C. RNA and cDNA from each sample were prepared as previously described. 6 μl cDNA from each sample was STA amplified using nested primers corresponding to the probes listed in FIG. 22 (FAT2, SCGB2A1, PGR, PRAME, TFAP2C, S100A2, FAT1, AGR2, PKP3, RND3, and PIP). Droplet numbers were normalized to blood volumes and the highest healthy donor value for each marker was subtracted from the patient sample values.

Figure 22:
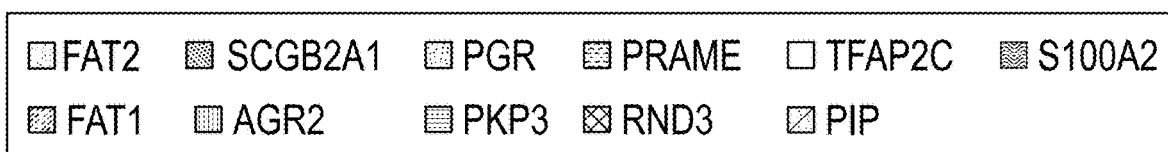
FIG. 22 is a graph that shows the results of a breast cancer assay for a multiplexed eleven marker assay used in a field of 9 metastatic breast cancer patient, 5 localized breast cancer patients, and 15 healthy donors. The results show that the assay detects cancer in 7 of 9 metastatic breast cancer patients, 2 of 5 localized breast cancer patients, and none of the healthy donor samples.
Figure 22:
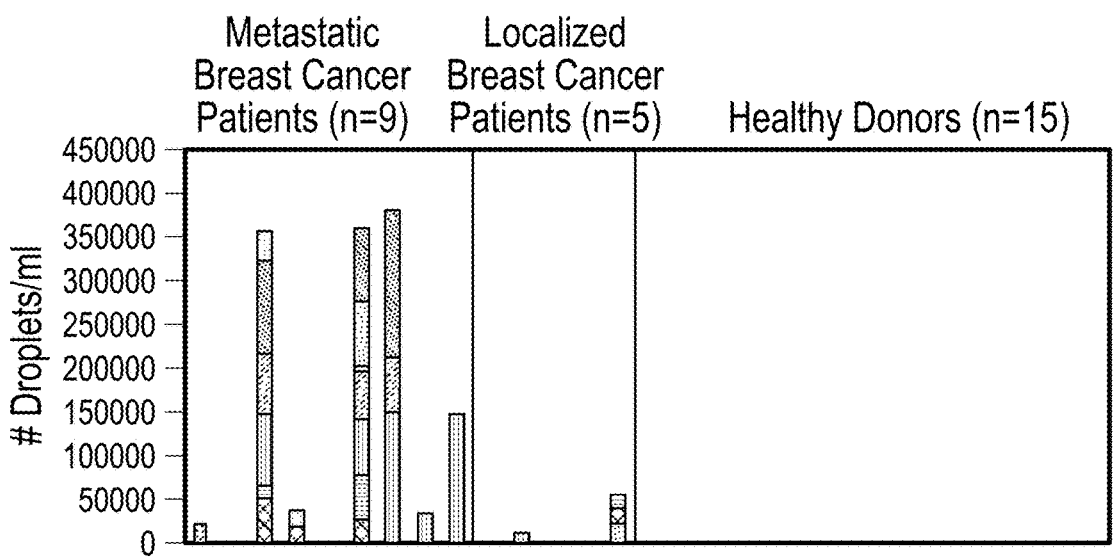

FIG. 22 shows the above-background signal for each patient. These methods detected 7/9 (78%) of metastatic samples and 2/5 (40%) of localized samples. The sensitivity of each marker alone varied from 1/14 to 6/14, with the two most relevant markers being AGR2 (6/14) and FAT1 (5/14), and the next four most relevant markers being RND3, PKP3, PRAME, and SCGB2A1 (3/14 each).

Example 12

AVR7 Detection in Metastatic Breast Cancer

Blood samples from 10 metastatic breast cancer patient and 7 healthy donors were processed though the CTC-Chip. Products were pelleted, treated with RNAlater™ and stored at −80C. RNA and cDNA from each sample were prepared as previously described. 6 µl of non-amplified cDNA were loaded into each droplet PCR reaction. The samples were analyzed with probes against the v7 isoform of the androgen receptor (ARv7, sequence in Table 1). Droplet number was normalized to blood volume.

Figure 23A:
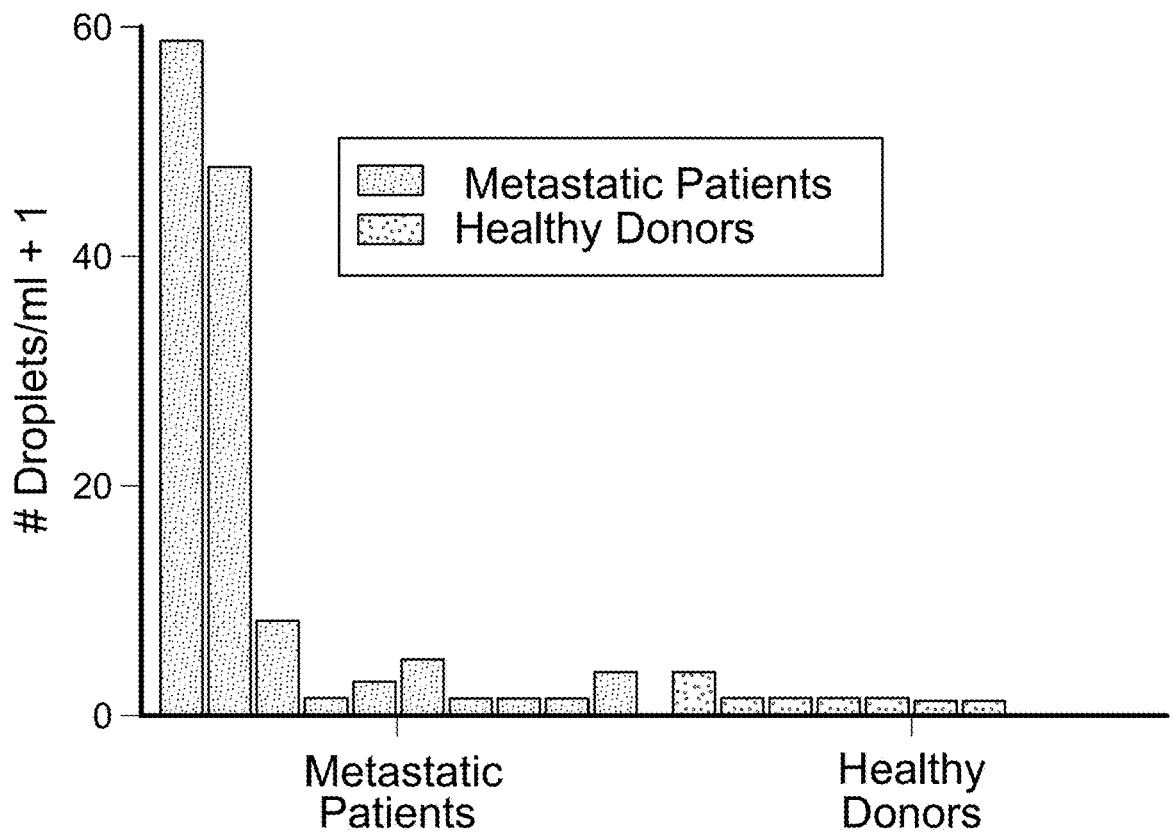
FIGS. 23A and 23B are graphs that show the results of ARv7 detection in metastatic breast cancer patients.
Figure 23B:
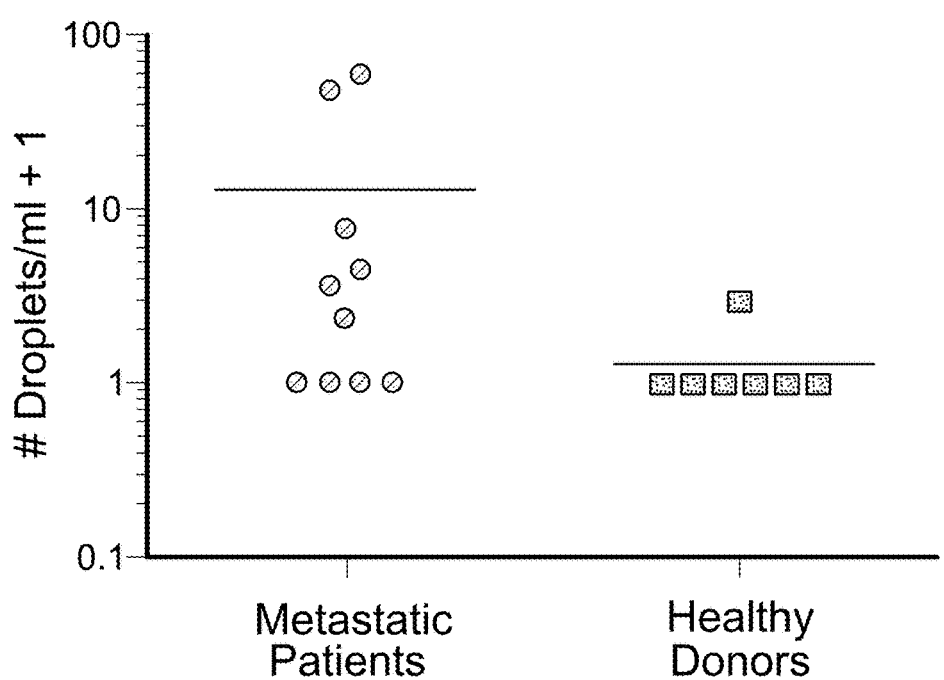

As shown in FIG. 23A, ARv7 was detected in 5/10 patients (50%) at above background (HD) levels, demonstrating that the assay is successful at detecting ARv7 from liquid biopsy. One of the patients had a triple negative breast cancer, suggesting utility of ARv7 as a marker even in the triple negative breast cancer (TNBC) context (e.g., patients who do not express genes for any of the three most common breast cancer markers, the estrogen receptor (ER), HER2/neu, and the progesterone receptor (PR) marker).

Example 13

Multiplexed vs. Individual Marker Assays for Melanoma

Figure 24A:
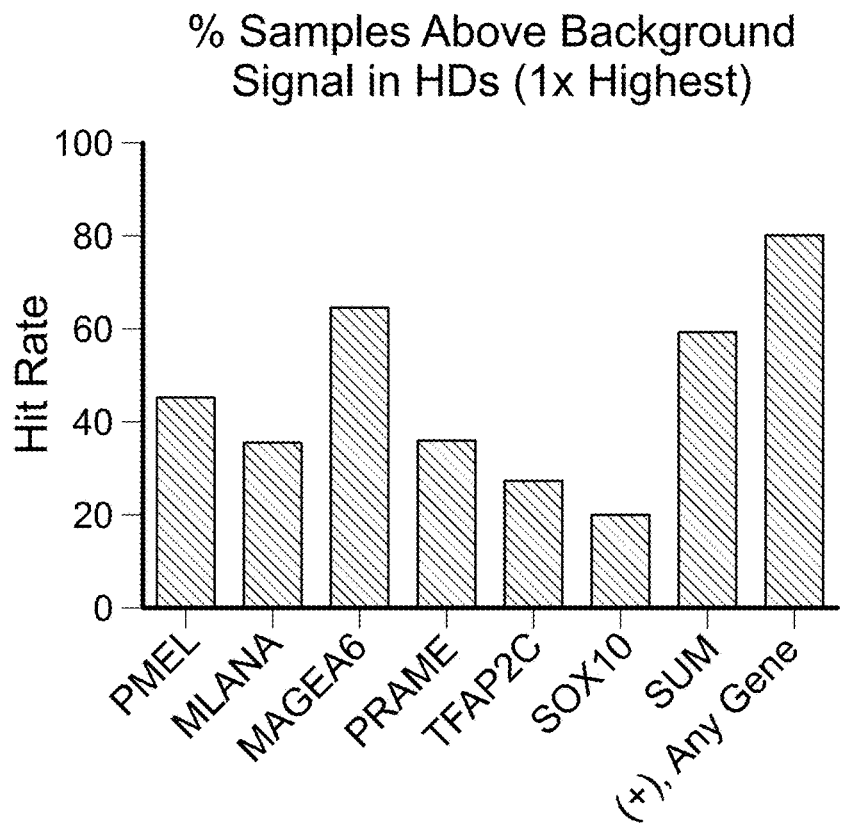
FIG. 24A is a bar graph showing the detection rate of individual markers (PMEL, MLANA, MAGEA6, PRAME, TFAP2C, and SOX10) and a combined marker cocktail (SUM) in 34 melanoma patients.
Figure 24B:
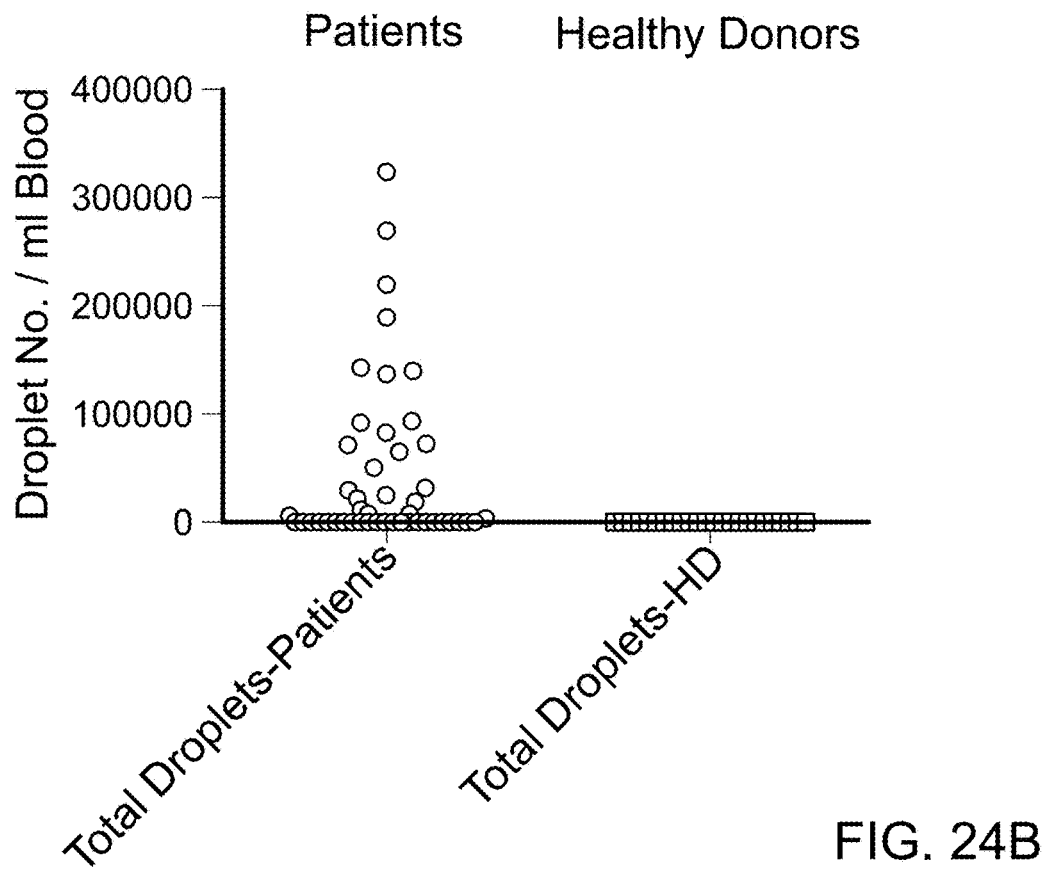
FIG. 24B is a dot plot distribution of droplet signals detected in 34 melanoma patients for 182 draw points as compared to 15 healthy donors demonstrating an overall detection sensitivity above healthy donor background signal of 81% (based on draw points) and a specificity of 100% (by draw points).

Blood samples from 34 metastatic or unresectable melanoma patients, each with multiple draw points (total draw points: 182), and 15 healthy donors were processed though the CTC-Chip. Products were pelleted, treated with RNAlater™ and flash frozen at −80C. RNA and cDNA from each sample were prepared as previously described. 12 µl cDNA from each sample was amplified by specific target amplification (10 cycles) using nested primers corresponding to the probes listed along the bottom of the graph in FIG. 24A (individual markers PMEL, MLANA, MAGEA6, PRAME, TFAP2C, and SOX10)). Droplet numbers were normalized to blood volumes. FIG. 24B shows a dot plot distribution of droplet signals detected in melanoma patients as compared to healthy donors. The detection sensitivity was 81% for all patient draw points (a patient draw is scored positive if any 1 of 6 markers shows droplet signals above the highest background signal in HD for that particular marker). Of the individual markers, PMEL and MLANA showed the highest detection rate.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for analyzing circulating tumor cells (CTCs) in a blood sample from a subject, the method comprising:
   isolating circulating tumor cells (CTCs) from the blood sample;
   isolating ribonucleic acid (RNA) from the CTC;
   generating cDNA molecules in solution from the isolated RNA;
   encapsulating cDNA molecules into individual droplets;
   amplifying cDNA within each of the individual droplets in the presence of one or more reporter groups configured to bind specifically to cDNA corresponding to tumor lineage-specific RNA from a specific type of tissue that is the source of the CTCs and not to bind to cDNA from normal cells in the blood;
   detecting droplets that contain the reporter groups as an indicator of the presence of amplified cDNA molecules from CTCs in the droplets; and
   analyzing cDNA molecules from CTCs in the detected droplet;
   wherein amplifying cDNA molecules within each of the individual droplets comprises conducting PCR in each droplet,
   wherein at least one primer set for each type of cancer is used for amplifying the cDNA molecules within each of the droplets, wherein each primer set corresponds to a selected cancer gene,
   wherein the selected cancer genes include prostate cancer-selective genes or breast cancer-selective genes,
   wherein the prostate cancer-selective genes are FAT1, TMPRSS2, AGR2, FOLH1, HOXDB13, KLK2, KLK3, and STEAP2,
   wherein the primer sets corresponding to the prostate cancer-selective genes are:
   FAT1 (primer 1 SEQ ID NO:23, primer 2 SEQ ID NO:22),
   TMPRSS2 (primer 1 SEQ ID NO:134, primer 2 SEQ ID NO:133),
   AGR2 (primer 1 SEQ ID NO:2, primer 2 SEQ ID NO:1),
   FOLH1 (primer 1 SEQ ID NO:29, primer 2 SEQ ID NO:28),
   HOXDB13 (primer 1 SEQ ID NO:32, primer 2 SEQ ID NO:31),
   KLK2 (primer 1 SEQ ID NO:35, primer 2 SEQ ID NO:34),
   KLK3 (primer 1 SEQ ID NO:38, primer 2 SEQ ID NO:37), and
   STEAP2 (primer 1 SEQ ID NO:125, primer 2 SEQ ID NO:124); and/or
   wherein the breast cancer-selective genes are TFAP2C, S100A2, PGR, PIP, FAT2, AGR2, FAT1, RND3, PKP3, PRAME, and SCGB2A1, wherein the primer sets corresponding to the breast cancer-selective genes are:
TFAP2C (primer 1 SEQ ID NO:131, primer 2 SEQ ID NO:130),
S100A2 (primer 1 SEQ ID NO:80, primer 79 SEQ ID NO:103),
PGR (primer 1 SEQ ID NO:62, primer 2 SEQ ID NO:61),
PIP (primer 1 SEQ ID NO:164, primer 2 SEQ ID NO:163),
FAT2 (primer 1 SEQ ID NO:26, primer 2 SEQ ID NO:25),
AGR2 (primer 1 SEQ ID NO:2, primer 2 SEQ ID NO:1),
FAT1 (primer 1 SEQ ID NO:23, primer 2 SEQ ID NO:22),
RND3 (primer 1 SEQ ID NO:77, primer 2 SEQ ID NO:76),
PKP3 (primer 1 SEQ ID NO:65, primer 2 SEQ ID NO:64),
PRAME (primer 1 SEQ ID NO:149, primer 2 SEQ ID NO:148), and
SCGB2A1 (primer 1 SEQ ID NO:83, primer 2 SEQ ID NO:82).

2. The method of claim 1, further comprising reducing a volume of the product before isolating RNA.

3. The method of claim 1, further comprising removing contaminants from the solution containing the cDNA molecules before encapsulating the cDNA molecules.

4. The method of claim 1, wherein generating the cDNA molecules from the isolated RNA comprises conducting reverse transcription (RT) polymerase chain reaction (PCR) of the isolated RNA.

5. The method of claim 1, wherein amplifying cDNA within droplets comprises conducting PCR in a plurality of the droplets.

6. The method of claim 1, wherein encapsulating individual cDNA further comprises encapsulating PCR reagents in individual droplets with the cDNA and forming at least 1000 droplets of a non-aqueous liquid.

7. The method of claim 1, wherein the one or more reporter groups comprise a fluorescent label.

8. The method of claim 3, wherein removing contaminants from the solution containing the cDNA molecules comprises the use of Solid Phase Reversible Immobilization (SPRI).

9. The method of claim 8, wherein the SPRI comprises
immobilizing cDNA in the solution with magnetic beads that are configured to specifically bind to the cDNA;
removing contaminants from the solution; and
eluting purified cDNA.

10. The method of claim 6, wherein the non-aqueous liquid comprises one or more fluorocarbons, hydrofluorocarbons, mineral oils, silicone oils, and hydrocarbon oils.

11. The method of claim 1, wherein the CTCs arise from metastatic or primary/localized cancers.

12. The method of claim 1, wherein analyzing the CTCs in the detected droplets comprises monitoring CTCs from blood samples taken over time from a patient with a known cancer, and testing, imaging, or both testing and imaging the CTCs to provide a prognosis for the patient.

13. The method of claim 1, wherein analyzing the CTCs in the detected droplets comprises testing, imaging, or testing and imaging the CTCs to provide an indication of a response by the CTCs to a therapeutic intervention.

14. The method of claim 1, wherein analyzing the CTCs in the detected droplets comprises determining a number or level of CTCs per unit volume of a blood sample from a patient to provide a measure of tumor burden in the patient.

15. The method of claim 14, further comprising using the measure of tumor burden in the patient to select a therapy.

16. The method of claim 14, further comprising determining the measure of tumor burden in the patient at a second time point to monitor the tumor burden over time.

17. The method of claim 1, wherein the cDNA is pre-amplified prior to amplifying the cDNA within each of the droplet.

18. The method of claim 17, wherein the cDNA is pre-amplified using nested primers corresponding to one or more primers that relate to one or more prostate cancer and/or breast cancer-selective genes.

19. The method of claim 17, wherein the cDNA is pre-amplified using non-specific whole transcriptome amplification (WTA).

* * * * *

UNITED STATES PATENT AND TRADEMARK OFFICE
CERTIFICATE OF CORRECTION

| | |
|---|---|
| PATENT NO. | : 11,898,209 B2 |
| APPLICATION NO. | : 17/065889 |
| DATED | : February 13, 2024 |
| INVENTOR(S) | : Daniel A. Haber et al. |

It is certified that error appears in the above-identified patent and that said Letters Patent is hereby corrected as shown below:

In the Claims

Column 160, Line 33-34:
In Claim 17, delete "each of the droplet." and insert -- the droplets. --

Signed and Sealed this
Sixteenth Day of April, 2024

Katherine Kelly Vidal
*Director of the United States Patent and Trademark Office*

SEQUENCE LISTING

<160> NUMBER OF SEQ ID NOS: 330

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgacagtta gagccgatat cac                                              23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caattcagtc ttcagcaact tgag                                             24

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aacctgcaga tacagctc                                                18

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtggcttta aaatgtcagg aa                                           22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtcgccaag tttgatggt                                               19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctgtgtattc ggccaaagc                                               19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctgcattt ttggacatag gag                                          23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccttgcact tccattatga c                                            21

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 9
gtactgtcat tcacct                                                       16

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggcctaca ttctgaacgc                                                   20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggttcttt cttttgcctt ctc                                               23

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ctgcatcgtc attct                                                        15

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtttcatcct ccctgtgctg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctccttgat cttccgcttc                                                   20

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 15
ctgcttttgt tggt                                                      14

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatgccccac ttgcagta                                                  18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctcgtaaac tggctaatgg t                                              21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
acctacccca atatatgaag gaaa                                           24

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgctgccac aaccagt                                                   17

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcacatcca tctggtacgt g                                              21

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 21
ctgccgcaaa ttc                                                          13

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gatccttatg ccatcaccgt                                                   20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atcagcagag tcaatcagtg ag                                                22

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cagcgttccc gg                                                           12

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctggatgct gacatttctg a                                                 21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcctccactc atctccaact                                                   20

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 27
atcacagagg gagacc                                              16

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caatgtgata ggtactctca gagg                                     24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgttccaaag ctcctcacaa                                          20

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
agctgctcca ctctga                                              16

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagccagatg tgttgcca                                            18

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgtacggaa tgcgtttctt g                                        21

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 33
cagactccag cgg                                                          13

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgtgtaca gtcatggatg g                                                 21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtcttcaggc tcaaacaggt                                                   20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ttctttaggc aatgggca                                                     18

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgtgctgga cgctgga                                                      17

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgatacctt gaagcacacc attac                                             25

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 39
gctcgggtga ttct                                                    14

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cacatttgag tgaagcttgt cg                                           22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcggatgtca aacaagtcaa g                                            21

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
aatgaagcca ccaca                                                   15

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaaggagaag atctgccagt g                                            21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gctgactcct ctgctcaag                                               19

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 45
ccagagtcat catgc                                                        15

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccagtagcct gattgtgcat                                                   20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtcagtgat tctgttcaag ga                                                22

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
aagagggcat tttggttgt                                                    19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actcttacac cacggctga                                                    19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccatcaaggc tctgtatcca t                                                 21

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 51
aggatcactg tcagga                                                      16

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggatctgagc aggagaaata cc                                               22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaattcttca ttcccttgaa ctga                                             24

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gaaaaagaca aattccaaag                                                  20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aagatggaca ggtatgacaa gtc                                              23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
actctttcca catagtcaga tgg                                              23

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 57
atttttaacc cactcctcg                                                19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgtcctggct gttcattctg                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggatcccta tctcttgcca                                               20

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
ctgtccatct cct                                                      13

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggcaattggt ttgaggcaa                                                19

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggactggata aatgtattca agca                                          24

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
tgcaagttat caagaagttt tgtaagtt                                            28

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctggtggagg agaacgg                                                        17

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggtcgctgga tgaaaggtt                                                      19

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
agcagctcga a                                                              11

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caggcatcgt cagtttcct                                                      19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acacaatgga tctggtgcta a                                                   21

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 69
gataggtgct ttgctg                                                    16

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gaggagagaa tcaacaaact gc                                             22

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aggttcaggt actccttcca g                                              21

<210> SEQ ID NO 72
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
attgaggcgc acat                                                      14

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atacttctgc ttggtgtagg c                                              21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agccattgta ctctttaacc ca                                             22

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 75
ggagactctg cgaga                                                       15

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccgagaatta cgttcctaca gtg                                              23

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcggacattg tcatagtaag ga                                               22

<210> SEQ ID NO 78
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
tttgaaatcg acacac                                                      16

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctgccttgct ctccttcc                                                    18

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttactcagc ttgaacttgt cg                                               22

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 81
gccacagatc catg                                                        14

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acttccttga tccctgcca                                                   19

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtcttttcaa ccatgtcctc ca                                               22

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tgctgatggt cctca                                                       15

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
caatgccacc gaagcct                                                     17

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cttttatttt catcctcagt gcaaac                                           26

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
gagttgaaat ctgaggcc                                                18

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cttgtcactt tcgttcagca g                                            21

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cttcatggtg tgggctca                                                18

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
tgcgggtact gg                                                      12

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tccttggatg actctcccta c                                            21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agataccacc tccctgaaga a                                            21

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 93
aggagcggga tggag                                                    15

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agaggtttaa tgggctcaca g                                             21

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctctggtctg tcgtcatgta ag                                            22

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
tcaccttctc cacca                                                    15

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cacaccacca tacctggata at                                            22

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tcacttgagg ccaagagttc                                               20

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 99
ggtccagcca agttc                                                    15

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctttcttcag ggtctggtca tt                                            22

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cttgtcgtct tcggaaatgt tatg                                          24

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tgactctggg agaaa                                                    15

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaggcaagtc agcctttct                                                19

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tgtccatctt gtcgtcttcg                                               20

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gatgactctg ggaga                                                    15

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gctcaccatg tgtgacttga                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tgggagagag acagcttgta                                               20

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gagagctgca tcagt                                                    15

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaagtccac gctcaccat                                                19

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcagccttgc tctctagc                                                 18

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 111
gagagctgca tcagt                                                    15

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctctgcacaa actcttccat ttc                                           23

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tttcctcgcc cattcttacc                                               20

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ttacagtgaa gtcctcc                                                  17

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggaaggaggg aacagaaatc c                                             21

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtgagctact ggctgaacta tt                                            22

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 117
atttgagaag aatggtgga                                            19

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aggagatgtg ctggattgtc                                           20

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tctgcatgaa ttatacattg accac                                     25

<210> SEQ ID NO 120
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
aactgaccac gctg                                                 14

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
actgcagaga taagtttagc tgac                                      24

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tcaccatttt gcttacttcc ttg                                       23

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ttgttcaaga agccac                                                            16

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
catgttgcct acagcctct                                                         19

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tctccaaact tcttcctcat tcc                                                    23

<210> SEQ ID NO 126
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
atcagcaggt tcatgca                                                           17

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaagatcatc ctgtcagacg ag                                                     22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cttccgagct agaacctgta tg                                                     22

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
tcaactcatt tcggc                                                15

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gatcagacag tcattcgcaa ag                                        22

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gacaatcttc cagggactga g                                         21

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
gttcagaggg ttctt                                                15

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cccaacccag gcatgatg                                             18

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tcaatgagaa gcaccttggc                                           20

<210> SEQ ID NO 135
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 135
tccagcagag ct                                                         12

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgctggaatg gacaagaact c                                               21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gctcatggag attgaactgg t                                               21

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138 cctttggct gtatct                                                      16

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cttactggcg ttttctcatg c                                               21

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ccaactcttg tagaggtctc aag                                             23

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 141
gcccactttt cctaggt                                                    17

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggaccaggga aagataaagc c                                               21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcaaggtaga ttcgtgacag a                                               21

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
aatcccaacc acaaa                                                      15

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cattttgtgg ttgggattct gg                                              22

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gatgctgtgg atgtggct                                                   18

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 147
atctaccttg ctgctca                                                    17

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gccttgcact tccattatga c                                               21

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ctctgcattt ttggacatag gag                                             23

<210> SEQ ID NO 150
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
gaggtcctga ggc                                                        13

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
atgtggagtt tacagtgtct gg                                              22

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
agcttctcac tgagtgttgc                                                 20

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 153
cagccaagtg taacc                                                    15

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acggctccca tcctcct                                                  17

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ccactatgtc accatgtacc tg                                            22

<210> SEQ ID NO 156
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
agaaccagca gc                                                       12

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgctctgaca acccttatgc                                               20

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ggctgaggat cactttgtag a                                             21

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 159
gtctttgctg acatt                                                      15

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
catcagcagg accagtagc                                                  19

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tgtctgtgct ccctgatct                                                  19

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
agtaccagga ctgct                                                      15

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tcatttggac gtactgactt gg                                              22

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cttgctccag ctcctgttc                                                  19

<210> SEQ ID NO 165
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 165
ggttctctgc ctg                                                          13

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ggtgtttggt ctaggatgga g                                                 21

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
actgggtttg acttcgtagc                                                   20

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
atgctgtatt ttgcac                                                       16

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gtgactctcc tgacatcctt ag                                                22

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ccatctcatt tcgtcctcca a                                                 21

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
acagacatag gcaaagt                                                    17

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
actctgaaaa actttggact gatg                                            24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tctagcaatc aacagatgag ttct                                            24

<210> SEQ ID NO 174
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gagccaaacg cc                                                         12

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
agctccttcc agtccgaat                                                  19

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtctgctcat caatcacctc a                                               21

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 177
atacccattg tcatcgc                                                   17

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ggacagagag aacaaggatg aac                                            23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tgtgggagaa tataggtgga ttg                                            23

<210> SEQ ID NO 180
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ctgtgctgga caatg                                                     15

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gctttgacat cagtagacca gag                                            23

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ctgtccgcag atcagacttg                                                20

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 183
tcaaaaagtg gaaaggtga                                                    19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cctggaaaat ggcctcctt                                                    19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cattgcctac aggaagtctg g                                                 21

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
tatgccaaga gtgtgag                                                      17

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ccagaggtaa aggtgccaac                                                   20

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tcccagataa ctgtcatgaa gc                                                22

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
gcagagtaac tacaaaggc                                                19

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cctcaaatac atcaagcaca gc                                            22

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ggaagccttc accagcaa                                                 18

<210> SEQ ID NO 192
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
cccaggtggt cca                                                      13

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ttgcaggctt cacataccott                                              20

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gcccgacatg cttgagt                                                  17

<210> SEQ ID NO 195
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ggacaacgac cttt                                                         14

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
ctcttgcagc cattcctctt                                                   20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cccttacccc agtcacttct                                                   20

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
cctcttctct cctcccct                                                     18

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tggacagaag acatactcat aaagg                                             25

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ggtgccagca tgaatccc                                                     18

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 201
tggacctgca gttatca                                                17

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
atcttccctc cattctgctt c                                           21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
cagttcccac tcactttctc ag                                          22

<210> SEQ ID NO 204
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
gccaccccac tc                                                     12

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ttttgcacca gtctcgctt                                              19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gccgcactga cagtatgag                                              19

<210> SEQ ID NO 207
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 207
tgggagccct g                                                        11

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cgactgcgag tgataccg                                                 18

<210> SEQ ID NO 209
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ctctccacgc actccct                                                  17

<210> SEQ ID NO 210
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
aacagccaca acg                                                      13

<210> SEQ ID NO 211
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgccgctcat gttcatgc                                                 18

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
caggacacca tgaggaacag                                               20

<210> SEQ ID NO 213
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 213
tcccgcttca                                                          10

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aagatgtcag acactgagaa cg                                            22

<210> SEQ ID NO 215
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cgaagcccga tgtggtc                                                  17

<210> SEQ ID NO 216
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
agtccaaagc acacga                                                   16

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
aggagatgtg ctggattgtc                                               20

<210> SEQ ID NO 218
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tctgcatgaa ttatacattg accac                                         25

<210> SEQ ID NO 219
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 219
aactgaccac gctg					14

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
atgtggagtt tacagtgtct gg					22

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
agcttctcac tgagtgttgc					20

<210> SEQ ID NO 222
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
cagccaagtg taacc					15

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gagatctgct tgaatgtgct g					21

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
caacagaggt ttttcacagc at					22

<210> SEQ ID NO 225
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
tggcaaggtc cgccc                                                     15

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
catggtaggc tgagatgctt t                                              21

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gacgataagg agacctgctt tg                                             22

<210> SEQ ID NO 228
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
tgcaagtcaa gctgc                                                     15

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gcgcattctg gaatttgtac tc                                             22

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gctatgccaa agtgttcgat g                                              21

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
ggaagagcct cagaa                                                      15

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tgatggatat tctctggatg gc                                              22

<210> SEQ ID NO 233
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cctgaatctt tactctctct ccttg                                           25

<210> SEQ ID NO 234
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
cagtttggta cattctattt cttcc                                           25

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gcacttcaag ttcaccatca c                                               21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
accagtttat tgtcaccttc ca                                              22

<210> SEQ ID NO 237
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 237
cttgactttc tcccctg                                                    17

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acatctatta ttgctactat tgtgtgtt                                        28

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tgggagcctc ttctctcttc                                                 20

<210> SEQ ID NO 240
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
attgtcgttg acacc                                                      15

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ttcatttgat aagcacacag tctg                                            24

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
accttgaaca tggcatagtc tg                                              22

<210> SEQ ID NO 243
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 243
agtcttccag ttccac                                                    16

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
aatcagctcc gcttccttg                                                 19

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
tgcttatctc gttgtccttc g                                              21

<210> SEQ ID NO 246
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
catcatccac atcc                                                      14

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagaagcgca gaagattgta ag                                             22

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
tctttctgat ctgccatcgc                                                20

<210> SEQ ID NO 249
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
gtccacaacg gtt                                                              13

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
agaagcgagt ccgactgt                                                         18

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
cactgcacac catctcaca                                                        19

<210> SEQ ID NO 252
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
gccccaggac g                                                                11

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cagatggagg aggaagattc tg                                                    22

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gtatactgcc tggagttctc tg                                                    22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 255
ctggttcagg tctccattac ag                                              22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gctgtgactc tgagcaagta                                                 20

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tgtcctcctc aatctggttt atg                                             23

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gacagaaggg cttggagatt t                                               21

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cggtggcgtt gtagaagat                                                  19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
agaagatctc tgcctccga                                                  19

<210> SEQ ID NO 261
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 261
caagatagtt gtggtgggag ac                                           22

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
agggtctctg gtctactgat g                                            21

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
tttggattta ccgcttggg                                               19

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
gactccagtg tgggagag                                                18

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
gggcccacat ataaatcctc ac                                           22

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ctgctggtca ctgttctcat c                                            21

<210> SEQ ID NO 267
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 267
cttcgcggtg tggtgaa                                                    17

<210> SEQ ID NO 268
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gctgtgtctc ccgtcaaa                                                   18

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ctgggacaca ttgccttct                                                  19

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
ccaccatgca ttctttcaat tct                                             23

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
aaacccagtt tgaggagatg ag                                              22

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccctgccaat atcttgggta at                                              22

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 273
acagcaactt ccttgatccc                                          20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
gcggcatcac tgtctatgaa                                          20

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ccttgccttc tcttaggctt t                                        21

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
agcagtggtt tcagcatca                                           19

<210> SEQ ID NO 277
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
cagataactc tcattcagta ttcttgg                                  27

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ctctaatgta gcttgacctc atct                                     24

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gagaagttgg acaagattgg g					21

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gctgagaagt tctgtgaatt cttta					25

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gtttcctcaa ccagtcacat aga					23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
agttgtctag cagtttccac ata					23

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gggaaagcct gtctgaagtg					20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
tcgtagcctc cagggtaata g					21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gttacaggtc tcctatctac agc                                           23

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gctcagcctc tctggaag                                                 18

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ctctcttacc ctgattcgga tg                                            22

<210> SEQ ID NO 288
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ggcgtctgcc tgtgatt                                                  17

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cctgagttct ggtgccaaag                                               20

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gggcatgagc agcttcaa                                                 18

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
ccactggctt ggtggattt                                              19

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
tcaacagaaa tgcccagagt t                                           21

<210> SEQ ID NO 293
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
cttctccagc tgggcatt                                               18

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tgctgtggca gcagatg                                                17

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
cggtcatgtc cgccttc                                                17

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
gcgtttccat tatgtcgttg tc                                          22

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 297
ccctccttct aggatagcg                                                19

<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
aacccggaat gggtgat                                                  17

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
aaacggactg atgtcactgg                                               20

<210> SEQ ID NO 300
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tggacagaag acatactcat aaagg                                         25

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cccactgctt caggaaacat a                                             21

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gtcagacatc ttccctccat tc                                            22

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 303
gccgcactga cagtatga                                                 18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cagaaggagc aggactgaaa                                               20

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
agcggcgcct cttatatc                                                 18

<210> SEQ ID NO 306
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gcgttgaaag agaagacaaa ct                                            22

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
ctactgcaac ggcaacct                                                 18

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gggccatgtt cttgctca                                                 18

<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 309
cagactcgct cgctcattt                                                    19

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
cctccatgcc cactttctt                                                    19

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cccaagtcag tacgtccaaa t                                                 21

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gcctaattcc cgaataacat caac                                              24

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
gctttaaaga aagtgtttgc tg                                                22

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
ctgtatctgc aggttcgtaa g                                                 21

<210> SEQ ID NO 315
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 315
aagttccccg tgtgcatc                                            18

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
ctcagcctcc tcgatgaa                                            18

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gtgaggaggc aaggttctg                                           19

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ggctccagag agggtagtt                                           19

<210> SEQ ID NO 319
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
tttggattta ccgcttggg                                           19

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
gactccagtg tgggagag                                            18

<210> SEQ ID NO 321
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 321
cttcgcggtg tggtgaa                                                    17

<210> SEQ ID NO 322
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
gctgtgtctc ccgtcaaa                                                   18

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
atcctgctgt atcacatcat g                                               21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
ctgacaggtt tcaaagaacc t                                               21

<210> SEQ ID NO 325
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ccagtgcctt tggttgct                                                   18

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
caagagccag atgggcaag                                                  19

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 327
tgccaagaga agatgctcac                                          20

<210> SEQ ID NO 328
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
cattgagtgc caacatgaag ac                                       22

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
aagaagctgc caatagggat                                          20

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
tgtccagaga ggtggatg                                            18
```